United States Patent
Feng et al.

Patent Number: 5,969,105
Date of Patent: Oct. 19, 1999

[54] STEM CELL FACTOR RECEPTOR AGONISTS

[76] Inventors: Yiqing Feng, 423 Mission Ct., St. Louis, Mo. 63130; Charles A. McWherter, 16564 Thunderhead Canyon Ct., Wildwood, Mo. 63011

[21] Appl. No.: 08/955,848

[22] Filed: Oct. 21, 1997

Related U.S. Application Data

[60] Provisional application No. 60/029,165, Oct. 25, 1996.

[51] Int. Cl.[6] ............... C12P 21/00; A61K 38/16; C07H 21/04; C07K 1/00
[52] U.S. Cl. ............... 530/351; 530/350; 435/69.1; 435/325; 514/2; 514/8; 536/23.4; 536/23.5
[58] Field of Search ............... 530/350, 351; 435/69.1, 325; 514/2, 8; 536/23.4, 23.5

[56] References Cited

U.S. PATENT DOCUMENTS 5,635,599  6/1997  Pastan et al. .

FOREIGN PATENT DOCUMENTS

| | | |
|---|---|---|
| 0 676 470 A1 | 10/1995 | European Pat. Off. . |
| 0 423 980 A1 | 4/1991 | WIPO . |
| WO 91/05795 | 5/1991 | WIPO . |
| WO 95/27732 | 10/1995 | WIPO . |
| WO 96/14410 | 5/1996 | WIPO . |
| WO 97/12985 | 4/1997 | WIPO . |
| WO 97/38101 | 10/1997 | WIPO . |

OTHER PUBLICATIONS

Reeke et al, "Three-Dimensional Structure of Favin: Saccharide Binding-Cyclic Permutation in Leguminous Lectins", Science, Nov. 28, 1986, vol. 234 pp. 1108-1111.

Luger et al, "An 8-fold Ba Barrel Protein with Redundant Folding Possibilities", Protein Engineering, vol. 3 pp. 249-258.

Cunningham et al, "Favion versus concanavalin A: Circularly permuted amino acid sequences", Proc. Natl. Acad. Sci. USA, Jul. 1979, vol. 76, No. 7, pp. 3218-3222.

(List continued on next page.)

*Primary Examiner*—David Saunders
*Assistant Examiner*—F. Pierre VanderVegt

[57] ABSTRACT

The present invention is drawn to human stem cell factor receptor agonist polypeptides, nucleic acid molecules encoding same, methods of producing the agonist polypeptides from the nucleic acid sequences and therapeutic compositions comprising the agonist polypeptides. The polypeptides of the instant invention are derived from the sequnce of SEQ ID NO:1, wherein 1-23 amino acids are optionally deleted from the C-terminus and the N-terminus is joined to the C-terminus, either directly or through a linker and C- and N-termini are created between an amino acid pair chosen from 23-24 through 110-111 of SEQ ID NO:1, generating said human stem cell factor receptor agonist polypeptide. The human stem cell factor receptor agonist polypeptide may additionally be immediately be preceded by a (methionine$^{-1}$), (alanine$^{-1}$) or (methionine$^{-2}$, alanine$^{-1}$).

12 Claims, 9 Drawing Sheets

OTHER PUBLICATIONS

Protasova et al, Circularly permuted dihydrofolate reductase of *E. coli* has functional activity and a destabilzed tertiary structure:, Protein Engineering, 1994, vol. 7, No. 11, pp. 1373–1777.

Zhang et al, "Circular Permutation of T4 Lysozyme", Biochemistry, vol. 32, No. 46, 1993.

Luger et al, "Correct Folding of Circularly Permuted Variants of a Ba Barrel Enzyme in Vivo", Science, vol. 243.

Hahn et al, "Native–like in vivo folding of a circularly permuted jellyroll protein shown by crystal structure analysis", Proc. Natl. Acad. Sci. USA, 1994, vol. 91, pp. 10417–10421.

Lin et al, "Rearranging the domains of pepsinogen", Protein Science, 1995, vol. 4, pp. 159–166.

Yang et al, "Aspartate transcarbamoylase containing circularly permuted catalytic polypeptide chains", Proc. Natl. Acad. Sci. USA, 1993, vol. 90, pp. 11980–11984.

Vignai et al, "Circular permutation within the coenzyme binding domain of the tetrameric glyceraldehyde–3–phosphate dehydrogenase from Bacillus stearothermophilus", Protein Science, 1995, vol. 4., pp. 994–1000.

Goldenberg et al, "Circular and Circularly Permuted Forms of Bovine Pancreatic Trypsin Inhibitor", J. Mol. Biol.1983 vol. 165, pp. 407–413.

Hemperly et al, "Circular permutation of amino acid sequences among legume lectins", TIBS, 1983, pp. 100–102.

Kreitman et al, "Circularly permuted interelukin 4 retains proliferative and binding activity", Cytokine, 1995, vol. 7, No. 4, pp. 311–318.

Li et al, "Degradation of Ornithine Decarboxylase", Mol. and Cel. Biol. 1993, vol. 13, No. 4, pp. 2377–2383.

Ritco et al, "Is the Continuity of the Domains Required for the Correct Folding of a Two–Domain Protein?", Biochemistry, 1995, vol. 34, pp. 16543–16551.

Garrett et al, "Are turns required for the folding of ribonuclease T1?", Protein Science, 1996, vol. 5., pp. 204–211.

Komar et al, "Kinetics of translation" FEBS Letters, 1995 vol. 376, pp. 195–198.

MacGregor et al, "A cicularly permuted a–amylase–type", FEBS Letters, 1996, vol. 378, pp. 263–266.

Koebnik et al, "Membrane Assembly of Circulary Permuted Variants", JMB, 1995, vol. 250, pp. 617–626.

Buchwalder et al, "A fully active variant of Dihydrofolate Reductase with a circularly permuted sequence", Biochemistry, 1992, vol. 31, pp. 1621–1630.

Viguera et al, "The order of secondary structure elements", J. Mol. Biol., 1995, vol. 247, pp. 670–681.

Mullins et al. "Transposition of Protein Sequences: Circular Permutation of Ribonuclease T1", J. Am. Chem. Soc., 1994, vol. 116, pp. 5529–5533.

Horlick et al, "Permuteins of interleukin 1B—a simplified approach for the construction of permutated proteins having new termini", Protein Engineering, USA, 1992, vol. 5, pp. 427–431.

Kreitman et al, "A circularly permuted recombinant interleukin 4 toxin with increase activity", Proc. Natl. Acad. Sci. USA, 1993, vol. 91, pp. 6889–3893.

Martin et al, "Primary Structure and Funtional Expression of Rat and Human Stem Cell Factor DNAs", Cell, vol. 63, 1990, pp. 203–211.

I. Construct tandemly-duplicated template

II. PCR-amplify tandemly-duplicated template

FIG. 5A

```
1   GAAGGGATCTGCAGGAATCGTGTGACTAATAATGTAAAAGACGTCACTAAATTGGTGGCA    60
    ----+----+----+----+----+----+----+----+----+----+----+----+
    CTTCCCTAGACGTCCTTAGCACACTGATTATTACATTTTCTGCAGTGATTTAACCACCGT

GluGlyIleCysArgAsnArgValThrAsnAsnValLysAspValThrLysLeuValAla

61  AATCTTCCAAAGACTACATGATAACCCTCAAATATGTCCCCGGGATGGATGTTTTGCCA    120
    ----+----+----+----+----+----+----+----+----+----+----+----+
    TTAGAAGGTTTCTGATGTACTATTGGGAGTTTATACAGGGGCCCTACCTACAAAACGGT

AsnLeuProLysAspTyrMetIleThrLeuLysTyrValProGlyMetAspValLeuPro

121 AGTCATTGTTGGGATAAGGCGAGATGGTAGTACAATTGTCAGACAGCTTGACTGATCTTCTG    180
    ----+----+----+----+----+----+----+----+----+----+----+----+
    TCAGTAACAACCTATTCGCTCTACCATCATGTTAACAGTCTGTCGAACTGACTAGAAGAC

SerHisCysTrpIleSerGluMetValValGlnLeuSerAspSerLeuThrAspLeuLeu

181 GACAAGTTTCAAATATTTCTGAAGGCTTGAGTAATTATTCCATCATAGACAAACTTGTG    240
    ----+----+----+----+----+----+----+----+----+----+----+----+
    CTGTTCAAAGTTTATAAAGACTTCCGAACTCATTAATAAGGTAGTATCTGTTTGAACAC

AspLysPheSerAsnIleSerGluGlyLeuSerAsnTyrSerIleIleAspLysLeuVal
```

FIG. 5B

```
     AATATAGTCGATGACTTGTGGAGTGCCTCAAAGAAAAACTCATCTAAGGATCTAAAAAAA
241  ------+---------+---------+---------+---------+---------+   300
     TTATATCAGCTACTGGAACACCTCACGGAGTTTCTTTTTGAGTAGATTCCTAGATTTTTT
     AsnIleValAspAspLeuValGluCysValLysGluAsnSerSerLysAspLeuLysLys

TCATTCAAGAGCCCAGAACCCAGGCTCTTTACTCCTGAAGAATTCTTTAGAATTTTTAAT
301  ------+---------+---------+---------+---------+---------+   360
     AGTAAGTTCTCGGGTCTTGGGTCCGAGAAATGAGGACTTCTTAAGAAATCTTAAAAATTA
     SerPheLysSerProGluProArgLeuPheThrProGluGluPhePheArgIlePheAsn

AGATCCATTGATGCCTTCAAGGACTTTGTAGTGGCATCTGAAACTAGTGATTGTGTGGTT
361  ------+---------+---------+---------+---------+---------+   420
     TCTAGGTAACTACGGAAGTTCCTGAAACATCACCGTAGACTTTGATCACTAACACACCAA
     ArgSerIleAspAlaPheLysAspPheValValAlaSerGluThrSerAspCysValVal

TCTTCAACATTAAGTCCTGAGAAAGATTCCAGTCAGTCACAAAACCATTTATGTTA
421  ------+---------+---------+---------+---------+---------+   480
     AGAAGTTGTAATTCAGGACTCTTTCTAAGGTCTCAGTCAGTCAGTGTTTTGGTAAATACAAT
     SerSerThrLeuSerProGluLysAspSerArgValSerValThrLysProPheMetLeu
```

FIG.5C

```
481  CCCCCTGTTGCAGCCAGTCCCTTAGGAATGACAGCAGTAGCAGTAATAGGAAGGCCAAA
     ----+---------+---------+---------+---------+---------+----  540
     GGGGGACAACGTCGGTCGAGGGAATCCTTACTGTCGTCATCGTCATTATCCTTCCGGTTT
     ProProValAlaAlaSerSerLeuArgAsnAspSerSerSerAsnArgLysAlaLys

541  AATCCCCTGGAGACTCCAGCCTACACTGGGCAGCCATGGCCAGCATTGCCAGCATTGTTTCT
     ----+---------+---------+---------+---------+---------+----  600
     TTAGGGGACCTCTGAGGTCGGATGTGACCCGTCGGTAACCGGTAACGGTCGTAACAAAGA
     AsnProProGlyAspSerSerLeuHisTrpAlaAlaMetAlaLeuProAlaLeuPheSer

601  CTTATATAATTGGCTTTGCTTTTGGAGCCTTATACTGAAGAGAGACAGCCAAGTCTTACA
     ----+---------+---------+---------+---------+---------+----  660
     GAATATATTAACCGAAACGAAAACCTCGGAATATGACCTTCTTCTCTGTCGGTTCAGAATGT
     LeuIleIleGlyPheAlaPheGlyAlaLeuTyrTrpLysLysArgGlnProSerLeuThr

661  AGGGCAGTTGAAAATATACAAATTAATGAAGAGGATAAGAGATAAGTATGTTGCAAGAG
     ----+---------+---------+---------+---------+---------+----  720
     TCCCGTCAACTTTTATATGTTTAATTACTTCTCCTATTACTCTTATTCATACAACGTTCTC
     ArgAlaValGluAsnIleGlnIleAsnGluGluAspAsnGluIleSerMetLeuGlnGlu

721  AAAGAGAGAGTTTCAAGAAGTGTAA
     ----+---------+-------    747
     TTTCTCTCTCAAAGTTCTTCACATT
     LysGluArgGluPheGlnGluValEnd
```

FIG.6A

```
    GAAGGGATCTGCAGGAATCGTGTGACTAATAATGTAAAAGACGTCACTAAATTGGTGGCA
1   ------+---------+---------+---------+---------+---------+   60
    CTTCCCTAGACGTCCTTAGCACACTGATTATTACATTTTCTGCAGTGATTTAACCACCGT

.GluGlyIleCysArgAsnArgValThrAsnAsnValLysAspValThrLysLeuValAla

AATCTTCCAAAAGACTACATGATAAACCCTCAAATATGTCCCCGGGATGGATGTTTTGCCA
61  ------+---------+---------+---------+---------+---------+   120
    TTAGAAGGTTTTCTGATGTACTATTGGGAGTTTATACAGGGCCCTACCTACAAAACGGT

AsnLeuProLysAspTyrMetIleThrLeuLysTyrValProGlyMetAspValLeuPro

AGTCATTGTTGGATAAGCGAGATGGTAGTACAATTGTCAGACAGCTTGACTGATCTTCTG
121 ------+---------+---------+---------+---------+---------+   180
    TCAGTAACAACCTATTCGCTCTACCATCATGTTAACAGTCTGTCGAACTGACTAGAAGAC

SerHisCysTrpIleSerGluMetValValGlnLeuSerAspSerLeuThrAspLeuLeu

GACAAGTTTTCAAATATTTCTGAAGGCTTGAGTAATTATTCCATCATAGACAAACTGTG
181 ------+---------+---------+---------+---------+---------+   240
    CTGTTCAAAAGTTTATAAAGACTTCCGAACTCATTAATAAGGTAGTATCTGTTTGAACAC

AspLysPheSerAsnIleSerGluGlyLeuSerAsnTyrSerIleIleAspLysLeuVal

AATATAGTCGATGACCTTGTGGAGTGCGTCAAAGAAACTCATCTAAGGATCTAAAAAA
241 ------+---------+---------+---------+---------+---------+   300
    TTATATCAGCTACTGGAACACCTCACGCAGTTTCTTTTGAGTAGATTCCTAGATTTTTT

AsnIleValAspAspLeuValGluCysValLysGluAsnSerSerLysAspLeuLysLys
```

FIG.6B

```
    TCATTCAAGAGCCCAGAACCCAGGCTCTCTTACTCCTGAAGAATTCTTTAGAATTTTAAT
301 ------+---------+---------+---------+---------+---------+ 360
    AGTAAGTTCTCGGGTCTTGGGTCCGAGAGAATGAGGACTTCTTAAGAAATCTTAAAAATTA

SerPheLysSerProGluProArgLeuPheThrProGluPhePheArgIlePheAsn

AGATCCATTGATGCCTTCAAGGACTTTGTAGTGGCATCTGAAACTAGTGATTGTGTGGTT
361 ------+---------+---------+---------+---------+---------+ 420
    TCTAGGTAACTACGGAAGTTCCTGAAACATCACCGTAGACTTTGATCACTAACACACCAA

ArgSerIleAspAlaPheLysAspPheValValAlaSerGluThrSerAspCysValVal

TCTTCAACATTAAGTCCTGAGAAAGATTCCAGAGTCAGTGTCACAAAACCATTTATGTTA
421 ------+---------+---------+---------+---------+---------+ 480
    AGAAGTTGTAATTCAGGACTCTTTCTAAGGTCTCAGTCACAGTGTTTGGTAAATACAAT

SerSerThrLeuSerProGluLysAspSerArgValSerValThrLysProPheMetLeu

CCCCCTGTTGCAGCC
481 ------+----- 495
    GGGGGACAACGTCGG

ProProValAlaAla
```

STEM CELL FACTOR RECEPTOR AGONISTS

The present application claims priority under Title 35, United States Code, §119 of U.S. Provisional application Ser. No. 60/029,165, filed Oct. 25, 1996.

FIELD OF THE INVENTION

The present invention relates to human stem cell factor (SCF) receptor agonists. These stem cell factor receptor agonists retain one or more activities of native stem cell factor and may also show improved hematopoietic cell-stimulating activity and/or an improved activity profile which may include reduction of undesirable biological activities associated with native stem cell factor and/or have improved physical properties which may include increased solubility, stability and refold efficiency.

BACKGROUND OF THE INVENTION

Colony stimulating factors which stimulate the differentiation and/or proliferation of bone marrow cells have generated much interest because of their therapeutic potential for restoring depressed levels of hematopoietic stem cell-derived cells. Colony stimulating factors in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. Certain factors such as stem cell factor are able to predominately affect stem cells.

Small amounts of certain hematopoietic growth factors account for the differentiation of a small number of stem cells into a variety of blood cell progenitors for the proliferation of those cells, and for the ultimate differentiation of mature blood cells from those lines. However, when stressed by chemotherapy, radiation or natural myelodysplastic disorders, a resulting period which patients are seriously leukopenic, anemic, neutropenic, or thrombocytopenic occurs. The use hematopoietic factors accelerates hematopoietic regeneration during this compromised period.

Stem cell factor has the ability to stimulate growth of early hematopoietic progenitors which are capable of maturing to erythroid, megakaryocyte, granulocyte, lymphocyte and macrophage cells. Stem cell factor treatment of mammals results in absolute increases in hematopoietic cells of both the myeloid and lymphoid cells.

EP 0 423 980 discloses novel stem cell factor (SCF) polypeptides including $SCF^{1-148}$, $SCF^{1-157}$, $SCF^{1-160}$, $SCF^{1-161}$, $SCF^{1-162}$, $SCF^{1-164}$, $SCF^{1-165}$, $SCF^{1-183}$, $SCF^{1-185}$, $SCF^{1-188}$, $SCF^{1-189}$, $SCF^{1-220}$, $SCF^{1-248}$, Rearrangement of Protein Sequences In evolution, rearrangements of DNA sequences serve an important role in generating a diversity of protein structure and function. Gene duplication and exon shuffling provide an important mechanism to rapidly generate diversity and thereby provide organisms with a competitive advantage, especially since the basal mutation rate is low (Doolittle, *Protein Science* 1:191–200, 1992).

The development of recombinant DNA methods has made it possible to study the effects of sequence transposition on protein folding, structure and function. The approach used in creating new sequences resembles that of naturally occurring pairs of proteins that are related by linear reorganization of their amino acid sequences (Cunningham, et al., *Proc. Natl. Acad. Sci. U.S.A.* 76:3218–3222, 1979; Teather & Erfle, *J. Bacteriol.* 172: 3837–3841, 1990; Schimming et al., *Eur. J. Biochem.* 204: 13–19, 1992; Yamiuchi and Minamikawa, *FEBS Lett.* 260:127–130, 1991: MacGregor et al., *FEBS Lett.* 378:263–266, 1996). The first in vitro application of this type of rearrangement to proteins was described by Goldenberg and Creighton (*J. Mol. Biol.* 165:407–413, 1983). A new N-terminus is selected at an internal site (breakpoint) of the original sequence, the new sequence having the same order of amino acids as the original from the breakpoint until it reaches an amino acid that is at or near the original C-terminus. At this point the new sequence is joined, either directly or through an additional portion of sequence (linker), to an amino acid that is at or near the original N-terminus, and the new sequence continues with the same sequence as the original until it reaches a point that is at or near the amino acid that was N-terminal to the breakpoint site of the original sequence, this residue forming the new C-terminus of the chain.

This approach has been applied to proteins which range in size from 58 to 462 amino acids (Goldenberg & Creighton, *J. Mol. Biol.* 165:407–413, 1983; Li & Coffino, *Mol. Cell. Biol.* 13:2377–2383, 1993). The proteins examined have represented a broad range of structural classes, including proteins that contain predominantly a -helix (interleukin-4; Kreitman et al., *Cytokine* 7:311–318, 1995), b -sheet (interleukin-1; Horlick et al., *Protein Eng.* 5:427–431, 1992), or mixtures of the two (yeast phosphoribosyl anthranilate isomerase; Luger et al., *Science* 243:206–210, 1989). Broad categories of protein function are represented in these sequence reorganization studies:

Enzymes

| | |
|---|---|
| T4 lysozyme | Zhang et al., Biochemistry 32:12311–12318 (1993); Zhang et al., Nature Struct. Biol. 1:434–438 (1995) |
| dihydrofolate reductase | Buchwalder et al., Biochemistry 31:1621–1630 (1994); Protasova et al., Prot. Eng. 7:1373–1377 (1995) |
| ribonuclease T1 | Mullins et al., J. Am. Chem. Soc. 116:5529–5533 (1994); Garrett et al., Protein Science 5:204–211 (1996) |
| Bacillus b-glucanse | Hahn et al., Proc. Natl. Acad. Sci. U.S.A. 91:10417–10421 (1994) |
| aspartate transcarbamoylase | Yang & Schachman, Proc. Natl. Acad. Sci. U.S.A. 90:11980–11984 (1993) |
| phosphoribosyl anthranilate isomerase | Luger et al., Science 243:206–210 (1989); Luger et al., Prot. Eng. 3:249–258 (1990) |
| pepsin/pepsinogen | Lin et al., Protein Science 4:159–166 (1995) |
| glyceraldehyde-3-phosphate dehydrogenase | Vignais et al., Protein Science 4:994–1000 (1995) |
| ornithine decarboxylase | Li & Coffino, Mol. Cell. Biol. 13:2377–2383 (1993) |
| yeast phosphoglycerate dehydrogenase | Ritco-Vonsovici et al., Biochemistry 34:16543–16551 (1995) |
| Enzyme Inhibitor | |
| basic pancreatic trypsin inhibitor | Goldenberg & Creighton, J. Mol. Biol. 165:407–413 (1983) |
| Cytokines | |
| interleukin-1b | Horlick et al., Protein Eng. 5:427–431 (1992) |
| interleukin-4 | Kreitman et al., Cytokine 7:311–318 (1995) |

-continued

| Tyrosine Kinase Recognition Domain | |
|---|---|
| a-spectrin SH3 domain | Viguera, et al., J. Mol. Biol. 247:670–681 (1995) |
| Transmembrane Protein | |
| omp A | Koebnik & Krämer, J. Mol. Biol. 250:617–626 (1995) |
| Chimeric Protein | |
| interleukin-4-Pseudomonas exotoxin fusion molecule | Kreitman et al., Proc. Natl. Acad. Sci. U.S.A. 91:6889–6893 (1994). |

The results of these studies have been highly variable. In many cases substantially lower activity, solubility or thermodynamic stability were observed (*E. coli* dihydrofolate reductase, aspartate transcarbamoylase, phosphoribosyl anthranilate isomerase, glyceraldehyde-3-phosphate dehydrogenase, ornithine decarboxylase, omp A, yeast phosphoglycerate dehydrogenase). In other cases, the sequence rearranged protein appeared to have many nearly identical properties as its natural counterpart (basic pancreatic trypsin inhibitor, T4 lysozyme, ribonuclease T1, Bacillus b-glucanase, interleukin-1b, a -spectrin SH3 domain, pepsinogen, interleukin-4). In exceptional cases, an unexpected improvement over some properties of the natural sequence was observed, e.g., the solubility and refolding rate for rearranged a -spectrin SH3 domain sequences, and the receptor affinity and anti-tumor activity of transposed interleukin-4-Pseudomonas exotoxin fusion molecule (Kreitman et al., *Proc. Natl. Acad. Sci. U.S.A.* 91:6889–6893, 1994; Kreitman et al., *Cancer Res.* 55:3357–3363, 1995).

The primary motivation for these types of studies has been to study the role of short-range and long-range interactions in protein folding and stability. Sequence rearrangements of this type convert a subset of interactions that are long-range in the original sequence into short-range interactions in the new sequence, and vice versa. The fact that many of these sequence rearrangements are able to attain a conformation with at least some activity is persuasive evidence that protein folding occurs by multiple folding pathways (Viguera, et al., *J. Mol. Biol.* 247:670–681, 1995). In the case of the SH3 domain of a -spectrin, choosing new termini at locations that corresponded to b-hairpin turns resulted in proteins with slightly less stability, but which were nevertheless able to fold.

The positions of the internal breakpoints used in the studies cited here are found exclusively on the surface of proteins, and are distributed throughout the linear sequence without any obvious bias towards the ends or the middle (the variation in the relative distance from the original N-terminus to the breakpoint is ca. 10 to 80% of the total sequence length). The linkers connecting the original N- and C-termini in these studies have ranged from 0 to 9 residues. In one case (Yang & Schachman, *Proc. Natl. Acad. Sci. U.S.A.* 90:11980–11984, 1993), a portion of sequence has been deleted from the original C-terminal segment, and the connection made from the truncated C-terminus to the original N-terminus. Flexible hydrophilic residues such as Gly and Ser are frequently used in the linkers. Viguera, et al. (*J. Mol. Biol.* 247:670–681, 1995) compared joining the original N- and C-termini with 3- or 4-residue linkers; the 3-residue linker was less thermodynamically stable. Protasova et al. (*Protein Eng.* 7:1373–1377, 1994) used 3- or 5-residue linkers in connecting the original N-termini of *E. coli* dihydrofolate reductase; only the 3-residue linker produced protein in good yield.

SUMMARY OF THE INVENTION

The modified human stem cell factor receptor agonists of the present invention can be represented by the Formula:

$$X^1-(L)_a-X^2$$

wherein;

a is 0 or 1;

$X^1$ is a peptide comprising an amino acid sequence corresponding to the sequence of residues n+1 through J;

$X^2$ is a peptide comprising an amino acid sequence corresponding to the sequence of residues 1 through n;

n is an integer ranging from 1 to J–1; and

L is a linker.

In the formula above the constituent amino acids residues of human stem cell factor are numbered sequentially 1 through J from the amino to the carboxyl terminus. A pair of adjacent amino acids within this protein may be numbered n and n+1 respectively where n is an integer ranging from 1 to J–1. The residue n+1 becomes the new N-terminus of the new stem cell factor receptor agonist and the residue n becomes the new C-terminus of the new stem cell factor receptor agonist.

The present invention relates to novel stem cell factor receptor agonists of the following formula:

```
GluGlyIleCysArgAsnArgValThrAsn         SEQ ID NO:82
                          10
AsnValLysAspValThrLysLeuValAla
                          20
AsnLeuProLysAspTyrMetIleThrLeu
                          30
LysTyrValProGlyMetAspValLeuPro
                          40
SerHisCysTrpIleSerGluMetValVal
                          50
GlnLeuSerAspSerLeuThrAspLeuLeu
                          60
AspLysPheSerAsnIleSerGluGlyLeu
                          70
SerAsnTyrSerIleIleAspLysLeuVal
                          80
AsnIleValAspAspLeuValGluCysVal
                          90
LysGluAsnSerSerLysAspLeuLysLys
                         100
SerPheLysSerProGluProArgLeuPhe
                         110
ThrProGluGluPhePheArgIlePheAsn
                         120
ArgSerIleAspAlaPheLysAspPheVal
                         130
ValAlaSerGluThrSerAspCysValVal
                         140
```

SerSerThrLeuSerProGluLysAspSer
150

ArgValSerValThrLysProPheMetLeu
160

ProProValAlaAlaSerSerLeuArgAsn
170

AspSerSerSerAsnArgLysAlaLys
180

AsnProProGlyAspSerSerLeuHisTrp
190

AlaAlaMetAlaLeuProAlaLeuPheSer
200

LeuIleIleGlyPheAlaPheGlyAlaLeu
210

TyrTrpLysLysArgGlnProSerLeuThr
220

ArgAlaValGluAsnIleGlnIleAsnGlu
230

GluAspAsnGluIleSerMetLeuGlnGlu
240

LysGluArgGluPheGlnGluVal
248 wherein optionally 1–106 amino acids can be deleted from the C-terminus of said stem cell factor receptor agonists;

wherein the N-terminus is joined to the C-terminus directly or through a linker capable of joining the N-terminus to the C-terminus and having new C- and N-termini at amino acids;

| | | |
|---|---|---|
| 23–24 | 39–40 | 96–97 |
| 24–25 | 40–41 | 97–98 |
| 25–26 | 64–65 | 98–99 |
| 26–27 | 65–66 | 99–100 |
| 27–28 | 66–67 | 100–101 |
| 28–29 | 67–68 | 101–102 |
| 29–30 | 68–69 | 102–103 |
| 30–31 | 69–70 | 103–104 |
| 31–32 | 70–71 | 104–105 |
| 32–33 | 89–90 | 105–106 |
| 33–34 | 90–91 | 106–107 |
| 34–35 | 91–92 | 107–108 |
| 35–36 | 92–93 | 108–109 |
| 36–37 | 93–94 | 109–110 |
| 37–38 | 94–95 | 110–111 |
| 38–39 | 95–96 | respectively; and | said stem cell factor receptor agonist polypeptide may optionally be immediately preceded by (methionine$^{-1}$), (alanine$^{-1}$) or (methionine $^{-2}$, alanine$^{-1}$).

A preferred embodiment of the invention relates to novel stem cell factor receptor agonists of the following formula:

GluGlyIleCysArpAsnArgValThrAsn     SEQ ID NO:1
10

AsnValLysAspValThrLysLeuValAla
20

AsnLeuProLysAspTyrMetIleThrLeu
30

LysTyrValProGlyMetAspValLeuPro
40

SerHisCysTrpIleSerGluMetValVal
50

GlnLeuSerAspSerLeuThrAspLeuLeu
60

AspLysPheSerAsnIleSerGluGlyLeu
70

SerAsnTyrSerIleIleAspLysLeuVal
80

AsnIleValAspAspLeuValGluCysVal
90

LysGluAsnSerSerLysAspLeuLysLys
100

SerPheLysSerProGluProArgLeuPhe
110

ThrProGluGluPhePheArgIlePheAsn
120

ArgSerIleAspAlaPheLysAspPheVal
130

ValAlaSerGluThrSerAspCysValVal
140

SerSerThrLeuSerProGluLysAspSer
150

ArgValSerValThrLysProPheMetLeu
160

ProProValAlaAla
165 wherein optionally 1–23 amino acids can be deleted from the C-terminus of said stem cell factor receptor agonists;

wherein the N-terminus is joined to the C-terminus directly or through a linker capable of joining the N-terminus to the C-terminus and having new C- and N-termini at amino acids;

| | | |
|---|---|---|
| 23–24 | 39–40 | 96–97 |
| 24–25 | 40–41 | 97–98 |
| 25–26 | 64–65 | 98–99 |
| 26–27 | 65–66 | 99–100 |
| 27–28 | 66–67 | 100–101 |
| 28–29 | 67–68 | 101–102 |
| 29–30 | 68–69 | 102–103 |
| 30–31 | 69–70 | 103–104 |
| 31–32 | 70–71 | 104–105 |
| 32–33 | 89–90 | 105–106 |
| 33–34 | 90–91 | 106–107 |
| 34–35 | 91–92 | 107–108 |
| 35–36 | 92–93 | 108–109 |
| 36–37 | 93–94 | 109–110 |
| 37–38 | 94–95 | 110–111 |
| 38–39 | 95–96 | respectively; and | said stem cell factor receptor agonist polypeptide may optionally be immediately preceded by (methionine$^{-1}$), (alanine$^{-1}$) or (methionine$^{-2}$, alanine$^{-1}$).

The more preferred breakpoints at which new C-terminus and N-terminus can be made are; 23-24, 24-25, 25-26, 33-34, 34-35, 35-36, 36-37, 38-39, 39-40, 40-41, 64-65, 65-66, 66-67, 67-68, 68-69, 69-70, 70-71, 89-90, 90-91, 91-92, 92-93, 93-94, 94-95, 95-96, 96-97, 97-98, 98-99, 99-100, 100-101, 101-102, 102-103, 103-104, 104-105 and 105-106 respectively.

The most preferred breakpoints at which new C-terminus and N-terminus can be made are; 64-65, 65-66, 92-93 and 93-94 respectively.

The stem cell factor receptor agonists of the present invention may contain amino acid substitutions, deletions and/or insertions. It is also intended that the stem cell factor receptor agonists of the present invention may also have amino acid deletions at either/or both the N- and C-termini of the original protein and or deletions from the new N- and/or C-termini of the sequence rearranged proteins in the formulas shown above.

The stem cell factor receptor agonists of the present invention may contain amino acid substitutions, deletions and/or insertions.

A preferred embodiment of the present invention the linker (L) joining the N-terminus to the C-terminus is a polypeptide selected from the group consisting of:

Ser;

Asn;

Gly;

Thr;

GlySer;

AlaAla;

GlySerGly;

GlyGlyGly;

GlyAsnGly;

GlyAlaGly;

GlyThrGly;

AlaSerAla;

AlaAlaAla;

GlyGlyGlySer SEQ ID NQ:37;

GlyGlyGlySerGlyGlyGlySer SEQ ID NQ:38;

GlyGlyGlySerGlyGlyGlySerGlyGlyGlySer SEQ ID NO:39;

SerGlyGlySerGlyGlySer SEQ ID NO:40;

GluPheGlyAsnMet SEQ ID NO:41;

GluPheGlyGlyAsnMet SEQ ID NO:42;

GluPheGlyGlyAsnGlyGlyAsnet SEQ ID NO:43;

GlyGlySerAspMetAlaGly SEQ ID NO:44; and

GlyGlyGlySerGlyGlylyThrGlyGlyGlySerGlyGlyGly SEQ ID NO:45.

The present invention also encompasses recombinant human stem cell factor receptor agonists co-administered or sequentially with one or more additional colony stimulating factors (CSF) including, cytokines, lymphokines, interleukins, hematopoietic growth factors which include but are not limited to GM-CSF, G-CSF, c-mpl ligand (also known as TPO or MGDF), M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, human growth hormone, B-cell growth factor, B-cell differentiation factor, and eosinophil differentiation factor (herein collectively referred to as "factors"). These co-administered mixtures may be characterized by having the usual activity of the factors or the mixture may be further characterized by having a biological or physiological activity greater than simply the additive function of the presence of the stem cell factor receptor agonists or the second factor alone. The co-administration may also provide an enhanced effect on the activity or an activity different from that expected by the presence of stem cell factor (SCF) or the second factor. The co-administration may also have an improved activity profile which may include reduction of undesirable biological activities associated with native human stem cell factor. In addition to the list above, IL-3 variants taught in WO 94/12639 and WO 94/12638, fusion protein taught in W0 95/21197, and W0 95/21254, G-CSF receptor agonists disclosed in WO 97/12977, c-mpl receptor agonists disclosed in WO 97/12978, IL-3 receptor agonists disclosed in WO 97/12979 and multi-functional receptor agonists taught in WO 97/12985 can be co-administered with the stem cell factor receptor agonists of the present invention. As used herein "IL-3 variants" refer to IL-3 variants taught in WO 94/12639 and WO 94/12638. As used herein "fusion proteins" refer to fusion protein taught in WO 95/21197, and WO 95/21254. As used herein "G-CSF receptor agonists" refer to G-CSF receptor agonists disclosed in WO 97/12978. As used herein "c-mpl receptor agonists" refer to c-mpl receptor agonists disclosed in WO 97/12978. As used herein "IL-3 receptor agonists" refer to IL-3 receptor agonists disclosed in WO 97/12979. As used herein "multi-functional receptor agonists" refer to multi-functional receptor agonists taught in WO 97/12985.

In addition, it is envisioned that in vitro uses would include the ability to stimulate bone marrow and blood cell activation and growth before the expanded cells are infused into patients. Another intended use is for the expansion of dendritic cells both in vivo and ex vivo.

BRIEF DESCRIPTION OF THE FIGURES

FIG. 1 schematically illustrates the sequence rearrangement of a protein. The N-terminus (N) and the C-terminus (C) of the native protein are joined through a linker, or joined directly. The protein is opened at a breakpoint creating a new N-terminus (new N) and a new C-terminus (new-C) resulting in a protein with a new linear amino acid sequence. A rearranged molecule may be synthesized de novo as linear molecule and not go through the steps of joining the original N-terminus and the C-terminus and opening of the protein at the breakpoint.

FIG. 2 shows a schematic of Method I, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the amino acid 11 (a.a. 1–10 are deleted) through a linker region and a new C-terminus created at amino acid 96 of the original sequence.

FIG. 3 shows a schematic of Method II, for creating new proteins in which the original N-terminus and C-terminus of the native protein are joined without a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to the original N-terminus and a new C-terminus created at amino acid 96 of the original sequence.

FIG. 4 shows a schematic of Method III, for creating new proteins in which the original N-terminus and C-terminus of the native protein are joined with a linker and different N-terminus and C-terminus of the protein are created. In the example shown the sequence rearrangement results in a new gene encoding a protein with a new N-terminus created at amino acid 97 of the original protein, the original C-terminus (a.a. 174) joined to amino acid 1 through a linker region and a new C-terminus created at amino acid 96 of the original sequence.

FIGS. 5A–5C show a DNA sequence encoding native stem cell factor based on the sequence of Martin et al. (*Cell* 63:203–211, 1990).

FIGS. 6A–6B show a DNA sequence encoding soluble stem cell factor based on the sequence of Langley et al. (*Archives of Bichemistry and Biophysica* 311:55–61, 1994).

DETAILED DESCRIPTION OF THE INVENTION

Figure 1:
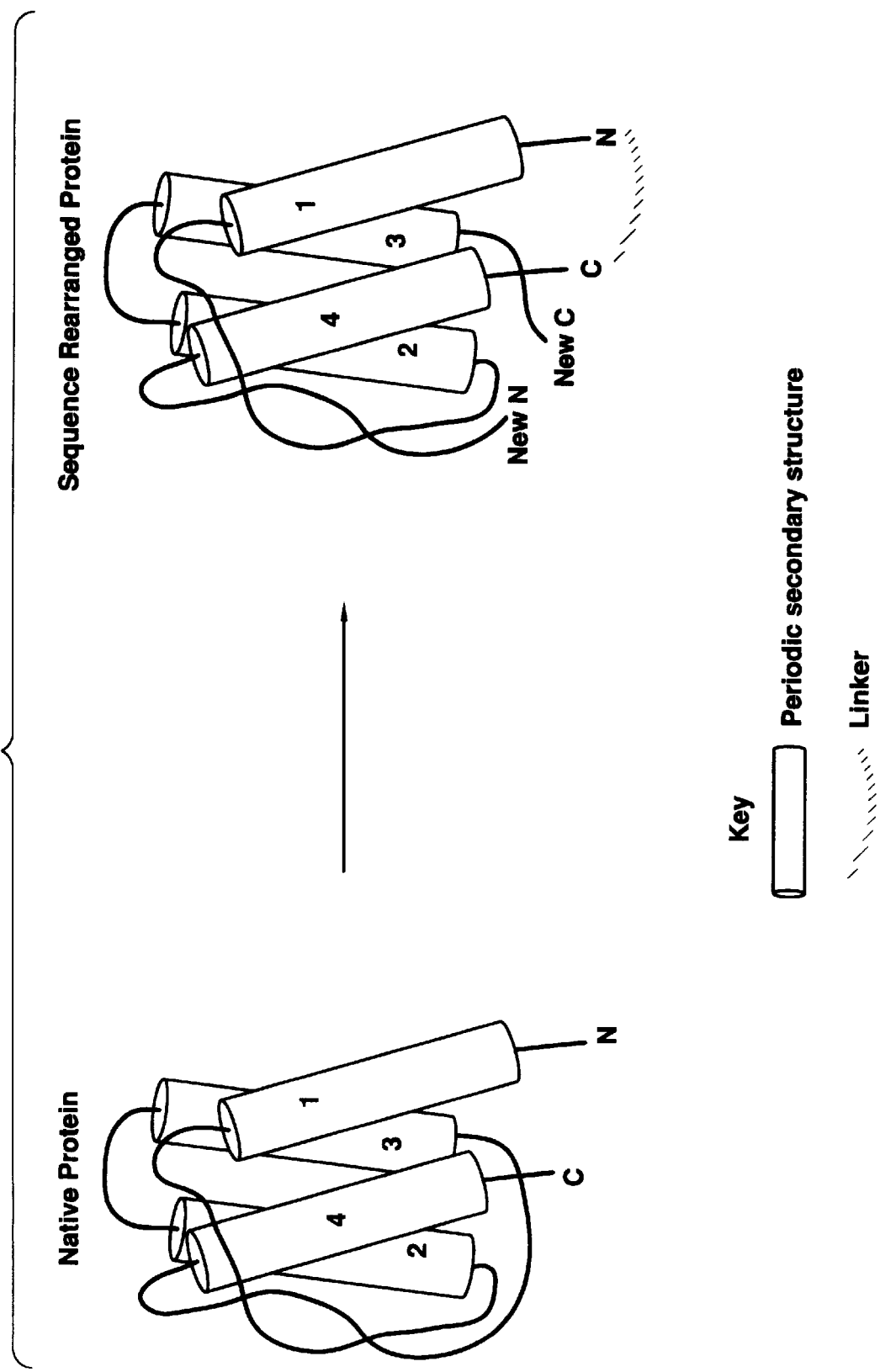

Stem cell factor receptor agonists of the present invention may be useful in the treatment of diseases characterized by decreased levels of hematopoietic cells.

A stem cell factor receptor agonist may be useful in the treatment or prevention of hematopoietic disorders. Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti-convulsants such as phenytoin or carbamazepine, antithyroids such as propylthiouracil and methimazole and diuretics. stem cell factor receptor agonists may be useful in preventing or treating the bone marrow suppression or hematopoietic deficiencies which often occur in patients treated with these drugs.

Hematopoietic deficiencies may also occur as a result of viral, microbial or parasitic infections, burns and as a result of treatment for renal disease or renal failure, e.g., dialysis. The present peptide may be useful in treating such hematopoietic deficiency.

Another aspect of the present invention provides plasmid DNA vectors for use in the method of expression of these novel stem cell factor receptor agonists. These vectors contain the novel DNA sequences described above which code for the novel polypeptides of the invention. Appropriate vectors which can transform host cells capable of expressing the stem cell factor receptor agonists include expression vectors comprising nucleotide sequences coding for the stem cell factor receptor agonists joined to transcriptional and translational regulatory sequences which are selected according to the host cells used. Vectors incorporating modified sequences as described above are included in the present invention and are useful in the production of the modified stem cell factor receptor agonist polypeptides. The vector employed in the method also contains selected regulatory sequences in operative association with the DNA coding sequences of the invention and capable of directing the replication and expression thereof in selected host cells.

As another aspect of the present invention, there is provided a novel method for producing the novel family of human stem cell factor receptor agonists. The method of the present invention involves culturing suitable cells or cell line, which has been transformed with a vector containing a DNA sequence coding for expression of the novel stem cell factor receptor agonist polypeptide. Suitable cells or cell lines may include various strains of bacteria such as *E. coli*, yeast, mammalian cells, or insect cells may be utilized as host cells in the method of the present invention.

Other aspects of the present invention are methods and therapeutic compositions for treating the conditions referred to above. Such compositions comprise a therapeutically effective amount of one or more of the stem cell factor receptor agonists of the present invention in a mixture with a pharmaceutically acceptable carrier. This composition can be administered either parenterally, intravenously or subcutaneously. When administered, the therapeutic composition for use in this invention is preferably in the form of a pyrogen-free, parenterally acceptable aqueous solution. The preparation of such a parenterally acceptable protein solution, having due regard to pH, isotonicity, stability and the like, is within the skill of the art.

The dosage regimen involved in a method for treating the above-described conditions will be determined by the attending physician considering various factors which modify the action of drugs, e.g. the condition, body weight, sex and diet of the patient, the severity of any infection, time of administration and other clinical factors. Generally, a daily regimen may be in the range of 0.5–150 µg/kg of non-glycosylated stem cell factor receptor agonists protein per kilogram of body weight. Dosages would be adjusted relative to the activity of a given receptor agonist and it would not be unreasonable to note that dosage regimens may include doses as low as 0.1 microgram and as high as 1 milligram per kilogram of body weight per day. In addition, there may exist specific circumstances where dosages of stem cell factor receptor agonist would be adjusted higher or lower than the range of 0.5–150 micrograms per kilogram of body weight. These include co-administration with other growth factors; co-administration with chemotherapeutic drugs and/or radiation; the use of glycosylated stem cell factor receptor agonists; and various patient-related issues mentioned earlier in this section. As indicated above, the therapeutic method and compositions may also include co-administration with other human factors. A non-exclusive list of other appropriate hematopoietins, colony stimulating factors and interleukins for simultaneous or serial co-administration with the polypeptides of the present invention includes GM-CSF, G-CSF, c-mpl ligand (also known as TPO or MGDF), M-CSF, erythropoietin (EPO), IL-1, IL-4, IL-2, IL-3, IL-5, IL 6, IL-7, IL-8, IL-9, IL-10, IL-11, IL-12, IL-13, IL-15, LIF, human growth hormone, B-cell growth factor, B-cell differentiation factor, and eosinophil differentiation factor (herein collectively referred to as "hematopoietic growth factors"), or combinations thereof. In addition to the list above, IL-3 variants taught in WO 94/12639 and WO 94/12638 fusion protein taught in WO 95/21197 and WO 95/21254, G-CSF receptor agonists disclosed in WO 97/12977, c-mpl receptor agonists disclosed in WO 97/12978, IL-3 receptor agonists disclosed in WO 97/12979 and multi-functional receptor agonists taught in 97/12985 can be co-administered with the polypeptides of the present invention.

The stem cell factor receptor agonists of the present invention may be useful in the mobilization of hematopoietic progenitors and stem cells in peripheral blood. Peripheral blood derived progenitors have been shown to be effective in reconstituting patients in the setting of autologous marrow transplantation. Hematopoietic growth factors, including G-CSF and GM-CSF, have been shown to enhance the number of circulating progenitors and stem cells in the peripheral blood. This has simplified the procedure for peripheral stem cell collection and dramatically decreased the cost of the procedure by decreasing the number of pheresis required. The stem cell factor receptor agonist of the present invention may be useful in mobilization of stem cells and further enhance the efficacy of peripheral stem cell transplantation.

The stem cell factor receptor agonists of the present invention may also be useful in the ex vivo expansion of hematopoietic progenitors. Colony stimulating factors (CSFs), such as G-CSF, have been administered alone, co-administered with other CSFs, or in combination with bone marrow transplants subsequent to high dose chemotherapy to treat the anemia, neutropenia and thrombocytopenia which are often the result of such treatment. However the period of severe anemia, neutropenia and thrombocytopenia may not be totally eliminated. The myeloid lineage, which is comprised of monocytes (macrophages), granulocytes (including neutrophils) and megakaryocytes, is critical in preventing infections and bleeding which can be life-threatening. anemia, neutropenia and thrombocytopenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow or other tissues, such as spleen or peripheral blood, is limited, 2) Graft Versus Host Disease, 3) graft rejection and 4) possible contamination with tumor cells. Stem cells and progenitor cells make up a very small percentage of the nucleated cells in the bone marrow, spleen and peripheral blood. It is clear that a dose response exists such that a greater number of multipotential hematopoietic progenitors will enhance hematopoietic recovery. Therefore, the in vitro expansion of stem cells should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogeneic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells. The limited number of multipotential hematopoietic progenitors may be overcome by ex-vivo expansion of the multipotential hematopoietic progenitors. In addition, stem cells can be specifically isolated based on the presence of specific surface antigens such as CD34+ in order to decrease tumor cell contamination of the marrow graft.

The following patents contain further details on separating stem cells, CD34+ cells, culturing the cells with hematopoietic factors, the use of the cells for the treatment of patients with hematopoietic disorders and the use of hematopoietic factors for cell expansion and gene therapy.

U.S. Pat. No. 5,061,620 relates to compositions comprising human hematopoietic stem cells provided by separating the stem cells from dedicated cells.

U.S. Pat. No. 5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM-CSF, IL-1, GM-CSF/IL-3 fusion protein and combinations thereof; (3) administering cellular preparation to a patient.

U.S. Pat No. 5,240,856 relates to a cell separator that includes an apparatus for automatically controlling the cell separation process.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from other cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1a, IL-3, IL-6 or GM-CSF is discussed in Brandt et al (*J. Clin. Invest.* 86:932–941, 1990).

One aspect of the present invention provides a method for selective ex-vivo expansion of stem cells. The term "stem cell" refers to the multipotential hematopoietic cells as well as early myeloid progenitor and precursors cells which can be isolated from bone marrow, spleen or peripheral blood. The term "expansion" refers to the proliferation and differentiation of the cells. The present invention provides a method for selective ex-vivo expansion of stem cells, comprising the steps of; (a) separating stem cells from other cells, (b) culturing the separated stem cells with a selective medium which contains a stem cell factor receptor agonist and optionally a second colony stimulating factor, and (c) harvesting the cultured stems cells. Stem cells, as well as committed progenitor cells destined to become neutrophils, erythrocytes, platelets, etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34+, Thy-1+ and lin-, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several subpopulations characterized by the presence or absence of co-expression of different lineage associated cell surface associated molecules. The most immature progenitor cells do not express any known lineage associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various colony stimulating factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt-3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various colony stimulating factors including c-kit ligand (Brandt et al., *Blood* 83:1507–1514, 1994; McKenna et al., *Blood* 86:3413–3420, 1995), IL-3 (Brandt et al., *Blood* 83:1507–1514, 1994; Sato et al., *Blood* 82:3600–3609, 1993), G-CSF (Sato et al., *Blood* 82:3600–3609, 1993), GM-CSF (Sato et al., *Blood* 82:3600–3609, 1993), IL-1 (Muench et al., *Blood* 81:3463–3473, 1993), IL-6 (Sato et al., *Blood* 82:3600–3609, 1993), IL-11 (Lemoli et al., *Exp. Hem.* 21:1668–1672, 1993; Sato et al., *Blood* 82:3600–3609, 1993), flt-3 ligand (McKenna et al., *Blood* 86:3413–3420, 1995) and/or combinations thereof (Brandt et al., *Blood* 83:1507 1514, 1994; Haylock et al., *Blood* 80:1405–1412, 1992, Koller et al., *Biotechnology* 11:358–363, 1993; Lemoli et al., *Exp. Hem.* 21:1668–1672, 1993), McKenna et al., *Blood* 86:3413–3420, 1995; Muench et al., *Blood* 81:3463–3473, 1993; Patchen et al., *Biotherapy* 7:13–26, 1994; Sato et al., *Blood* 82:3600–3609, 1993; Smith et al., *Exp. Hem.* 21:870–877, 1993; Steen et al., *Stem Cells* 12:214–224, 1994; Tsujino et al., *Exp. Hem.* 21:1379–1386, 1993). Among the individual colony stimulating factors, hIL-3 has been shown to be one of the most potent in expanding peripheral blood CD34+ cells (Sato et al., *Blood* 82:3600–3609, 1993; Kobayashi et al., *Blood* 73:1836–1841, 1989). However, no single factor has been shown to be as effective as the combination of multiple factors. The present invention provides methods for ex vivo expansion that utilize novel stem cell factor receptor agonists.

Another aspect of the invention provides methods of sustaining and/or expanding hematopoietic precursor cells which includes inoculating the cells into a culture vessel which contains a culture medium that has been conditioned by exposure to a stromal cell line such as HS-5 (WO 96/02662, Roecklein and Torok-Strob, *Blood* 85:997–1105, 1995) that has been supplemented with a stem cell factor receptor agonist of the present invention.

It is also envisioned that uses of stem cell factor receptor agonists of the present invention would include blood banking applications. In this setting the stem cell factor receptor agonists are given to a patent to increase the number of blood cells. Blood products are removed from the patient, prior to some medical procedure. The blood products are stored and transfused back into the patient after the medical procedure. Additionally, it is envisioned that uses of stem cell factor receptor agonists would include giving the stem cell factor receptor agonists to a blood donor prior to blood donation to increase the number of blood cells, thereby allowing the donor to safely give more blood.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270:404–410, 1995) include; 1) the treatment of many congenital metabolic disorders and immunodeficiencies (Kay and Woo, *Trends Genet.* 10:253–257, 1994), 2) neurological disorders (Friedmann, *Trends Genet.* 10:210–214, 1994), 3) cancer (Culver and Blaese, *Trends Genet.* 10:174–178, 1994) and 4) infectious diseases (Gilboa and Smith, *Trends Genet.* 10:139–144, 1994).

There are a variety of methods, known to those with skill in the art, for introducing genetic material into a host cell. A number of vectors, both viral and non-viral have been developed for transferring therapeutic genes into primary cells. Viral based vectors include; 1) replication deficient recombinant retrovirus (Boris-Lawrie and Temin, *Curr. Opin. Genet. Dev.* 3:102–109, 1993; Boris-Lawrie and Temin, *Annal. New York Acad. Sci.* 716:59–71, 1994; Miller, *Current Top. Microbiol. Immunol.* 158:1–24, 1992) and replication-deficient recombinant adenovirus (Berkner, *BioTechniques* 6:616–629, 1988; Berkner, *Current Top. Microbiol. Immunol.* 158:39–66, 1992; Brody and Crystal, *Annal. New York Acad. Sci.* 716:90–103, 1994). Non-viral based vectors include protein/DNA complexes (Cristiano et al., *PNAS USA*. 90:2122–2126, 1993; Curiel et al., *PNAS USA* 88:8850–8854, 1991; Curiel, *Annal. New York Acad. Sci.* 716:36–58, 1994), electroporation and liposome mediated delivery such as cationic liposomes (Farhood et al., *Annal. New York Acad. Sci.* 716:23–35, 1994).

The present invention provides an improvement to the existing methods of expanding hematopoietic cells, into which new genetic material has been introduced, in that it provides methods utilizing stem cell factor receptor agonists that may have improved biological activity and/or physical properties.

Another intended use of the stem cell factor receptor agonists of the present invention is for the generation of larger numbers of dendritic cells, from precursors, to be used as adjuvants for immunization. Dendritic cells play a crucial role in the immune system. They are the professional antigen-presenting cells most efficient in the activation of resting T cells and are the major antigen-presenting cells for activation of naive T cells in vivo and, thus, for initiation of primary immune responses. They efficiently internalize, process and present soluble tumor-specific antigens (Ag). Dendritic cells have the unique capacity to cluster naive T cells and to respond to Ag encounter by rapid up-regulation of the expression of major histocompatability complex (MHC) and costimulatory molecules, the production of cytokines and migration towards lymphatic organs. Since dendritic cells are of central importance for sensitizing the host against a neoantigen for CD4-dependent immune responses, they may also play a crucial role in the generation and regulation of tumor immunity.

Dendritic cells originate from a bone marrow CD34+ precursor common to granulocytes and macrophages, and the existence of a separate dendritic cell colony-forming unit (CFU-DC) that give rise to pure dendritic cell colonies has been established in humans. In addition, a post-CFU CD14+ intermediate has been described with the potential to differentiate along the dendritic cell or the macrophage pathway under distinct cytokine conditions. This bipotential precursor is present in the bone marrow, cord blood and peripheral blood. Dendritic cells can be isolated by the cell specific marker, CD83, which is expressed on mature dendritic cells, to delineate the maturation of cultured dendritic cells.

Dendritic cells based strategies provide a method for enhancing immune response against tumors and infectious agents. AIDS is another disease for which dendritic cell based therapies can be used, since dendritic cells can play a major role in promoting HIV-1 replication. An immunotherapy requires the generation of dendritic cells from cancer patients, their in vitro exposure to tumor Ag, derived from surgically removed tumor masses, and re-injection of these cells into the tumor patients. Relatively crude membrane preparations of tumor cells will suffice as sources of tumor antigen, avoiding the necessity for molecular identification of the tumor antigen. The tumor antigen may also be synthetic peptides, carbohydrates or nucleic acid sequences. In addition, concomitant administration of cytokines such as the stem cell factor receptor agonists of the present invention may further facilitate the induction of tumor immunity. It is foreseen that the immunotherapy can be in an in vivo setting, wherein the stem cell factor receptor agonist of the present invention is administered to a patient, having a tumor, alone or with other hematopoietic growth factors to increase the number of dendritic cells and endogenous tumor antigen is presented on the dendritic cells. It is also envisioned that in vivo immunotherapy can be with exogenous antigen. It is also envisioned that the immunotherapy treatment may include the mobilization of dendritic cell precursors or mature dendritic, by administering the stem cell factor receptor agonists of the present invention alone or with other hematopoietic growth factors to the patient, removing the dendritic cell precursors or mature dendritic cells from the patient, exposing the dendritic cells to antigen and returning the dendritic cells to the patient. Furthermore, the dendritic cells that have been removed can be cultured ex vivo with the stem cell factor receptor agonist of the present invention alone or with other hematopoietic growth factors to increase the number of dendritic cells prior to exposure to antigen. Dendritic cells based strategies also provide a method for reducing the immune response in auto-immune diseases.

Studies on dendritic cells have been greatly hampered by difficulties in preparing the cells in sufficient numbers and in a reasonably pure form. In an ex-vivo cell expansion setting, granulocyte-macrophage colony-stimulating factor (GM-CSF) and tumor necrosis factor-α (TNF-α) cooperate in the ex vivo generation of dendritic cells from hematopoietic progenitors (CD34+ cells) retrieved from bone marrow, cord blood, or peripheral blood and flk-2//flt-3 ligand and c-kit ligand (stem cell factor [SCF]) synergize to enhance the GM-CSF plus TNF-α induced generation of dendritic cells (Siena, S. et al. *Experimental Hematology* 23:1463–1471, 1995). Also provide is a method of ex vivo expansion of dendritic cell precursors or mature dendritic cells using the stem cell factor receptor agonists of the present invention to provide sufficient quantities of dendritic cells for immunotherapy.

Determination of the Linker

The length of the amino acid sequence of the linker can be selected empirically or with guidance from structural information, or by using a combination of the two approaches.

When no structural information is available, a small series of linkers can be prepared for testing using a design whose length is varied in order to span a range from 0 to 50 Å and whose sequence is chosen in order to be consistent with surface exposure (hydrophilicity, Hopp & Woods, *Mol. Immunol.* 20: 483–489, 1983; Kyte & Doolittle, *J. Mol. Biol.* 157:105–132, 1982; solvent exposed surface area, Lee & Richards, *J. Mol. Biol.* 55:379–400, 1971) and the ability to adopt the necessary conformation without deranging the configuration of the stem cell factor receptor agonist (conformationally flexible; Karplus & Schulz, *Naturwissenschaften* 72:212–213, (1985). Assuming an average of translation of 2.0 to 3.8 Å per residue, this would mean the length to test would be between 0 to 30 residues, with 0 to 15 residues being the preferred range. Exemplary of such an empirical series would be to construct linkers using a cassette sequence such as Gly-Gly-Gly-Ser repeated n times, where n is 1, 2, 3 or 4. Those skilled in the art will recognize that there are many such sequences that vary in length or composition that can serve as linkers with the primary consideration being that they be neither excessively long nor short (cf., Sandhu, *Critical Rev. Biotech.* 12: 437–462, 1992); if they are too long, entropy effects will likely destabilize the three-dimensional fold, and may also make folding kinetically impractical, and if they are too short, they will likely destabilize the molecule because of torsional or steric strain.

Those skilled in the analysis of protein structural information will recognize that using the distance between the chain ends, defined as the distance between the c-alpha carbons, can be used to define the length of the sequence to be used, or at least to limit the number of possibilities that must be tested in an empirical selection of linkers. They will also recognize that it is sometimes the case that the positions of the ends of the polypeptide chain are ill-defined in structural models derived from x-ray diffraction or nuclear magnetic resonance spectroscopy data, and that when true, this situation will therefore need to be taken into account in order to properly estimate the length of the linker required. From those residues whose positions are well defined are selected two residues that are close in sequence to the chain ends, and the distance between their c-alpha carbons is used to calculate an approximate length for a linker between them. Using the calculated length as a guide, linkers with a range of number of residues (calculated using 2 to 3.8 Å per residue) are then selected. These linkers may be composed of the original sequence, shortened or lengthened as necessary, and when lengthened the additional residues may be chosen to be flexible and hydrophilic as described above; or optionally the original sequence may be substituted for using a series of linkers, one example being the Gly-Gly-Gly-Ser cassette approach mentioned above; or optionally a combination of the original sequence and new sequence having the appropriate total length may be used.

Determination of the Amino and Carboxyl Termini of stem cell factor Receptor Agonists Sequences of stem cell factor receptor agonists capable of folding to biologically active states can be prepared by appropriate selection of the beginning (amino terminus) and ending (carboxyl terminus) positions from within the original polypeptide chain while using the linker sequence as described above. Amino and carboxyl termini are selected from within a common stretch of sequence, referred to as a breakpoint region, using the guidelines described below. A novel amino acid sequence is thus generated by selecting amino and carboxyl termini from within the same breakpoint region. In many cases the selection of the new termini will be such that the original position of the carboxyl terminus immediately preceded that of the amino terminus. However, those skilled in the art will recognize that selections of termini anywhere within the region may function, and that these will effectively lead to either deletions or additions to the amino or carboxyl portions of the new sequence.

It is a central tenet of molecular biology that the primary amino acid sequence of a protein dictates folding to the three-dimensional structure necessary for expression of its biological function. Methods are known to those skilled in the art to obtain and interpret three-dimensional structural information using x-ray diffraction of single protein crystals or nuclear magnetic resonance spectroscopy of protein solutions. Examples of structural information that are relevant to the identification of breakpoint regions include the location and type of protein secondary structure (alpha and 3–10 helices, parallel and anti-parallel beta sheets, chain reversals and turns, and loops; Kabsch & Sander, *Biopolymers* 22: 2577–2637, 1983; the degree of solvent exposure of amino acid residues, the extent and type of interactions of residues with one another (Chothia, *Ann. Rev. Biochem.* 53:537–572; 1984) and the static and dynamic distribution of conformations along the polypeptide chain (Alber & Mathews, *Methods Enzymol.* 154: 511–533, 1987). In some cases additional information is known about solvent exposure of residues; one example is a site of post-translational attachment of carbohydrate which is necessarily on the surface of the protein. When experimental structural information is not available, or is not feasible to obtain, methods are also available to analyze the primary amino acid sequence in order to make predictions of protein tertiary and secondary structure, solvent accessibility and the occurrence of turns and loops. Biochemical methods are also sometimes applicable for empirically determining surface exposure when direct structural methods are not feasible; for example, using the identification of sites of chain scission following limited proteolysis in order to infer surface exposure (Gentile & Salvatore, *Eur. J. Biochem.* 218:603–621, 1993). Thus using either the experimentally derived structural information or predictive methods (e.g., Srinivisan & Rose Proteins: Struct., *Funct. & Genetics*, 22: 81–99, 1995) the parental amino acid sequence is inspected to classify regions according to whether or not they are integral to the maintenance of secondary and tertiary structure. The occurrence of sequences within regions that are known to be involved in periodic secondary structure (alpha and 3–10 helices, parallel and anti-parallel beta sheets) are regions that should be avoided. Similarly, regions of amino acid sequence that are observed or predicted to have a low degree of solvent exposure are more likely to be part of the so-called hydrophobic core of the protein and should also be avoided for selection of amino and carboxyl termini. In contrast, those regions that are known or predicted to be in surface turns or loops, and especially those regions that are known not to be required for biological activity, are the preferred sites for location of the extremes of the polypeptide chain. Continuous stretches of amino acid sequence that are preferred based on the above criteria are referred to as a breakpoint region.

Materials and Methods

Recombinant DNA Methods

Unless noted otherwise, all specialty chemicals were obtained from Sigma Co., (St. Louis, Mo.). Restriction endonucleases and T4 DNA ligase were obtained from New England Biolabs (Beverly, Mass.) or Boehringer Mannheim (Indianapolis, Ind.).

Transformation of *E. coli* Strains

*E. coli* strains, such as DH5α™ (Life Technologies, Gaithersburg, Md.) and TG1 (Amersham Corp., Arlington Heights, Ill.) are used for transformation of ligation reactions and are the source of plasmid DNA for transfecting mammalian cells. *E. coli* strains, such as MON105 and JM101, can be used for expressing the stem cell factor receptor agonist of the present invention in the cytoplasm or periplasmic space.

MON105 ATCC#55204: F-, lamda-,IN(rrnD, rrE)1, rpoD+, rpoH358

DH5α™: F-, phi80dlacZdeltaM15, delta(lacZYA-argF) U169, deoR, recA1, enda1, hsdR17(rk-,mk+), phoA, supE44lamda-, thi-1, gyrA96, relA1

TG1: delta(lac-pro), supE, thi-1, hsdD5/F'(traD36, proA+B+, lacIq, lacZdeltaM15)

DH5a™ Subcloning efficiency cells are purchased as competent cells and are ready for transformation using the manufacturer's protocol, while both *E. coli* strains TG1 and MON105 are rendered competent to take up DNA using a $CaCl_2$ method. Typically, 20 to 50 mL of cells are grown in LB medium (1% Bacto-tryptone, 0.5% Bacto-yeast extract, 150 mM NaCl) to a density of approximately 1.0 optical density unit at 600 nanometers (OD600) as measured by a Baush & Lomb Spectronic spectrophotometer (Rochester, N.Y.). The cells are collected by centrifugation and resuspended in one-fifth culture volume of $CaCl_2$ solution (50 mM $CaCl_2$, 10 mM Tris-Cl, pH 7.4) and are held at 4° C. for 30 minutes. The cells are again collected by centrifugation and resuspended in one-tenth culture volume of $CaCl_2$ solution. Ligated DNA is added to 0.2 mL of these cells, and the samples are held at 4° C. for 1 hour. The samples are shifted to 42° C. for two minutes and 1 mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C. Single colonies are picked, grown in LB supplemented with appropriate antibiotic for 6–16 hours at 37° C. with shaking. Colonies are picked and inoculated into LB plus appropriate antibiotic (100 ug/mL ampicillin or 75 ug/mL spectinomycin) and are grown at 37° C. while shaking. Before harvesting the cultures, 1 ul of cells are analyzed by PCR for the presence of a stem cell factor gene. The PCR is carried out using a combination of primers that anneal to the stem cell factor gene and/or vector. After the PCR is complete, loading dye is added to the sample followed by electrophoresis as described earlier. A gene has been ligated to the vector when a PCR product of the expected size is observed.

Methods for Creation of Genes With New N-terminus/C-terminus

Method I. Creation of genes with new N-terminus/C-terminus which contain a linker region.

Figure 2:
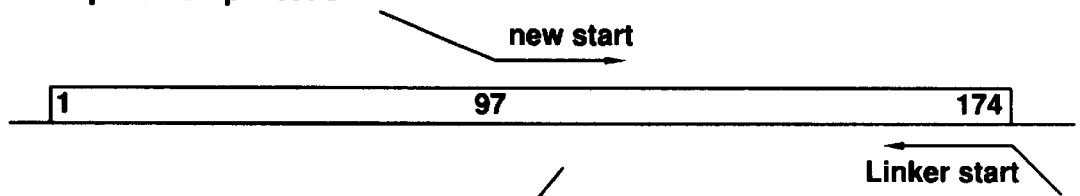
Figure 2:
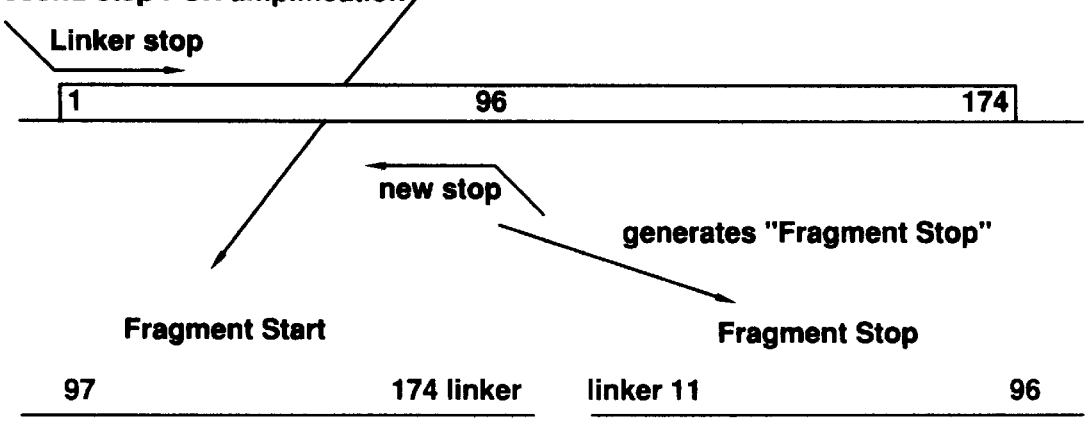
Figure 2:
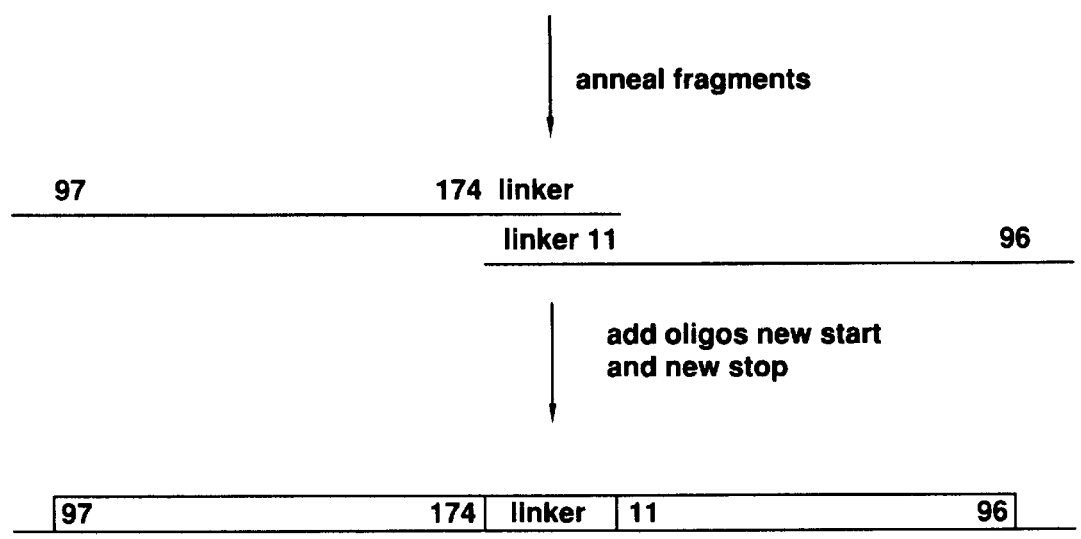

Genes with new N-terminus/C-terminus which contain a linker region separating the original C-terminus and N-terminus can be made essentially following the method described in L. S. Mullins, et al *J. Am. Chem. Soc.* 116, 5529–5533 (1994). Multiple steps of polymerase chain reaction (PCR) amplifications are used to rearrange the DNA sequence encoding the primary amino acid sequence of the protein. The steps are illustrated in FIG. 2.

In the first step, the primer set ("new start" and "linker start") is used to create and amplify, from the original gene sequence, the DNA fragment ("Fragment Start") that contains the sequence encoding the new N-terminal portion of the new protein followed by the linker that connects the C-terminal and N-terminal ends of the original protein. In the second step, the primer set ("new stop" and "linker stop") is used to create and amplify, from the original gene sequence, the DNA fragment ("Fragment Stop") that encodes the same linker as used above, followed by the new C-terminal portion of the new protein. The "new start" and "new stop" primers are designed to include the appropriate restriction enzyme recognition sites which allow cloning of the new gene into expression plasmids. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and one ug of template DNA; and 1× PCR buffer, 200 uM dGTP, 200 uM dATP, 200 uM dTTP, 200 uM dCTP, 2.5 units AmpliTaq DNA polymerase and 2 mM $MgCl_2$. PCR reactions are performed in a Model 480 DNA thermal cycler (Perkin Elmer Corporation, Norwalk, Conn.). "Fragment Start" and "Fragment Stop", which have complementary sequence in the linker region and the coding sequence for the two amino acids on both sides of the linker, are joined together in a third PCR step to make the full-length gene encoding the new protein. The DNA fragments "Fragment Start" and "Fragment Stop" are resolved on a 1% TAE gel, stained with ethidium bromide and isolated using a Qiaex Gel Extraction kit (Qiagen). These fragments are combined in equimolar quantities, heated at 70° C. for ten minutes and slow cooled to allow annealing through their shared sequence in "linker start" and "linker stop". In the third PCR step, primers "new start" and "new stop" are added to the annealed fragments to create and amplify the full-length new N-terminus/C-terminus gene. Typical PCR conditions are one cycle 95° C. melting for two minutes; 25 cycles 94° C. denaturation for one minute, 60° C. annealing for one minute and 72° C. extension for one minute; plus one cycle 72° C. extension for seven minutes. A Perkin Elmer GeneAmp PCR Core Reagents kit is used. A 100 ul reaction contains 100 pmole of each primer and approximately 0.5 ug of DNA; and 1× PCR buffer, 200 uM dGTP, 200 uM DATP, 200 uM dTTP, 200 uM dCTP, 2.5 units AmpliTaq DNA polymerase and 2 mM $MgCl_2$. PCR reactions are purified using a Wizard PCR Preps kit (Promega).

Method II. Creation of genes with new N-terminus/C-terminus without a linker region.

Figure 3:
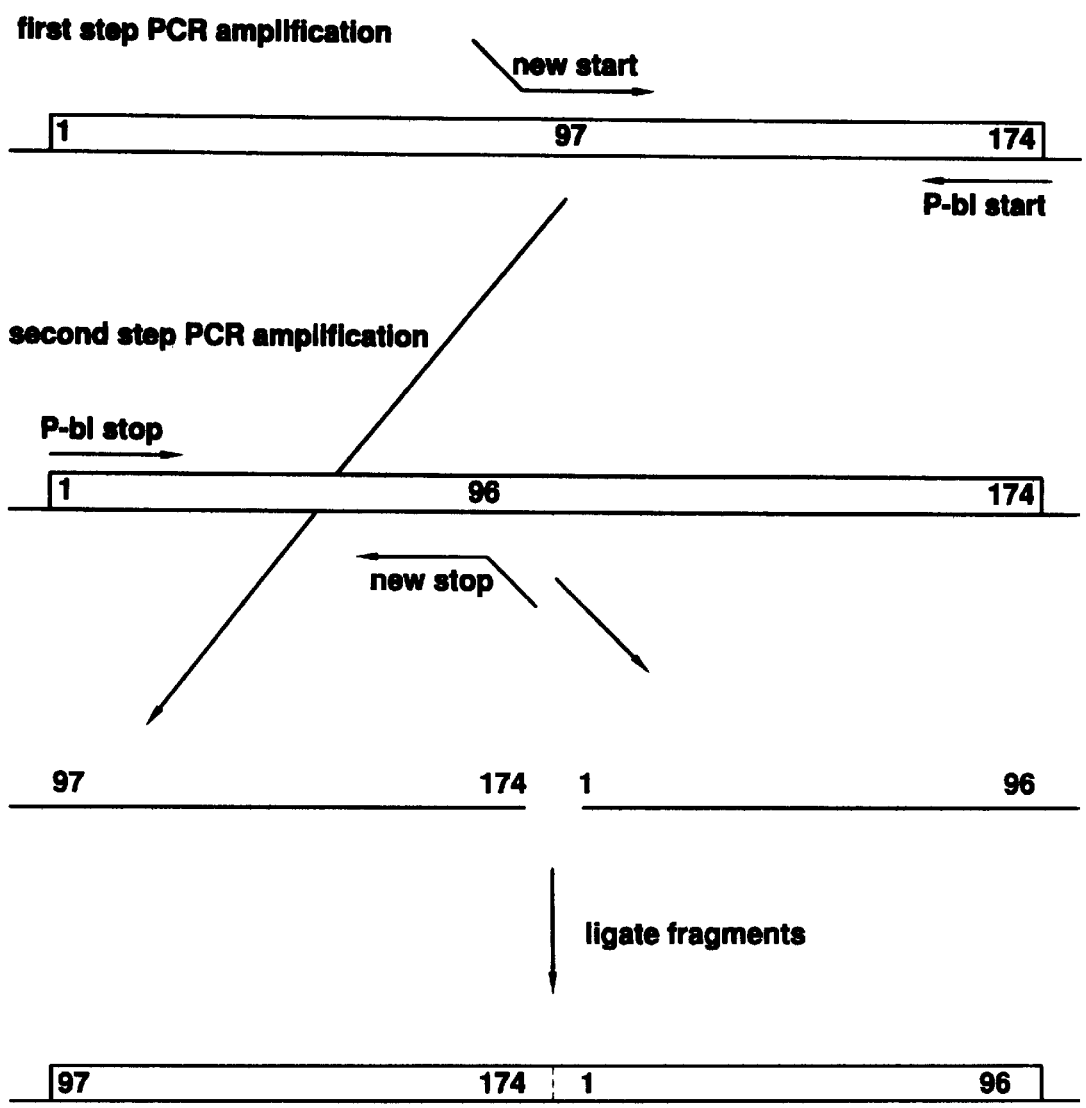

New N-terminus/C-terminus genes without a linker joining the original N-terminus and C-terminus can be made using two steps of PCR amplification and a blunt end ligation. The steps are illustrated in FIG. 3. In the first step, the primer set ("new start" and "P-bl start") is used to create and amplify, from the original gene sequence, the DNA fragment ("Fragment Start") that contains the sequence encoding the new N-terminal portion of the new protein. In the second step, the primer set ("new stop" and "P-bl stop") is used to create and amplify, from the original gene sequence, the DNA fragment ("Fragment Stop") that contains the sequence encoding the new C-terminal portion of the new protein. The "new start" and "new stop" primers are designed to include appropriate restriction sites which allow cloning of the new gene into expression vectors. Typical PCR conditions are one cycle 95° C. melting for two minutes; 25 cycles 94° C. denaturation for one minute, 50° C. annealing for 45 seconds and 72° C. extension for 45 seconds. Deep Vent polymerase (New England Biolabs) is used to reduce the occurrence of overhangs in conditions recommended by the manufacturer. The "P-bl start" and "P-bl stop" primers are phosphorylated at the 5' end to aid in the subsequent blunt end ligation of "Fragment Start" and "Fragment Stop" to each other. A 100 ul reaction contained 150 pmole of each primer and one ug of template DNA; and 1× Vent buffer (New England Biolabs), 300 uM dGTP, 300 uM DATP, 300 uM dTTP, 300 uM dCTP, and 1 unit Deep Vent polymerase. PCR reactions are performed in a Model 480 DNA thermal cycler (Perkin Elmer Corporation, Norwalk, Conn.). PCR reaction products are purified using a Wizard PCR Preps kit (Promega).

The primers are designed to include appropriate restriction enzyme recognition sites which allow for the cloning of the new gene into expression vectors. Typically "Fragment Start" is designed to create a NcoI restriction site, and "Fragment Stop" is designed to create a HindIII restriction site. Restriction digest reactions are purified using a Magic DNA Clean-up System kit (Promega). Fragments Start and Stop are resolved on a 1% TAE gel, stained with ethidium bromide and isolated using a Qiaex Gel Extraction kit (Qiagen). These fragments are combined with and annealed to the ends of the ~3800 base pair NcoI/HindIII vector fragment of pMON3934 by heating at 50° C. for ten minutes and allowed to slow cool. The three fragments are ligated together using T4 DNA ligase (Boehringer Mannheim). The result is a plasmid containing the full-length new N-terminus/C-terminus gene. A portion of the ligation reaction is used to transform E. coli strain DH5α cells (Life Technologies, Gaithersburg, Md.). Plasmid DNA is purified and sequence confirmed as below.

Figure 4:
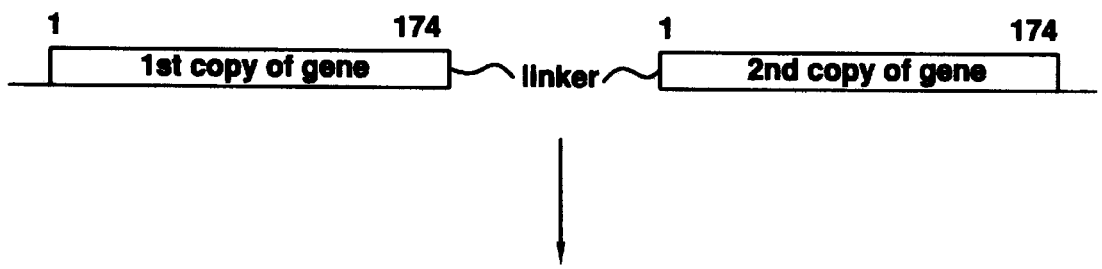
Figure 4:
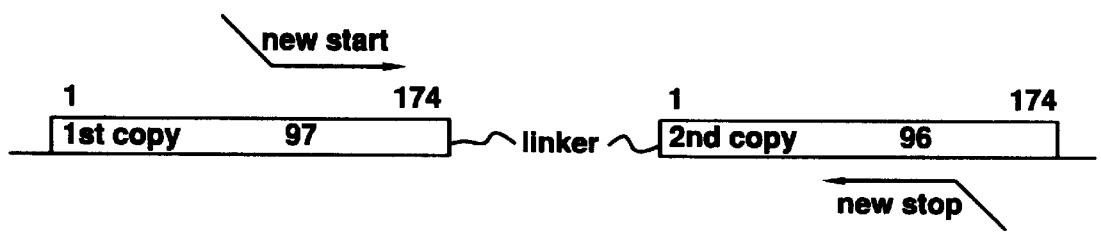
Figure 4:

Method III. Creation of new N-terminus/C-terminus genes by tandem-duplication method New N-terminus/C-terminus genes can be made based on the method described in R. A. Horlick, et al Protein Eng. 5:427–431 (1992). Polymerase chain reaction (PCR) amplification of the new N-terminus/C-terminus genes is performed using a tandemly duplicated template DNA. The steps are illustrated in FIG. 4.

The tandemly-duplicated template DNA is created by cloning and contains two copies of the gene separated by DNA sequence encoding a linker connecting the original C- and N-terminal ends of the two copies of the gene. Specific primer sets are used to create and amplify a full-length new N terminus/C-terminus gene from the tandemly-duplicated template DNA. These primers are designed to include appropriate restriction sites which allow for the cloning of the new gene into expression vectors. Typical PCR conditions are one cycle 95° C. melting for two minutes; 25 cycles 94° C. denaturation for one minute, 50° C. annealing for one minute and 72° C. extension for one minute; plus one cycle 72° C. extension for seven minutes. A Perkin Elmer GeneAmp PCR Core Reagents kit (Perkin Elmer Corporation, Norwalk, Conn.) is used. A 100 ul reaction contains 100 pmole of each primer and one ug of template DNA; and 1× PCR buffer, 200 uM dGTP, 200 uM DATP, 200 uM dTTP, 200 uM dCTP, 2.5 units AmpliTaq DNA polymerase and 2 mM $MgCl_2$. PCR reactions are performed in a Model 480 DNA thermal cycler (Perkin Elmer Corporation, Norwalk, Conn.). PCR reactions are purified using a Wizard PCR Preps kit (Promega).

DNA Isolation and Characterization

Plasmid DNA can be isolated by a number of different methods and using commercially available kits known to those skilled in the art. A few such methods are shown herein. Plasmid DNA is isolated using the Promega Wizard™ Miniprep kit (Madison, Wis.), the Qiagen QIAwell Plasmid isolation kits (Chatsworth, Calif.) or Qiagen Plasmid Midi kit. These kits follow the same general procedure for plasmid DNA isolation. Briefly, cells are pelleted by centrifugation (5000×g), plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted with TE. After screening for the colonies with the plasmid of interest, the E. coli cells are inoculated into 50–100 mLs of LB plus appropriate antibiotic for overnight growth at 37° C. in an air incubator while shaking. The purified plasmid DNA is used for DNA sequencing, further restriction enzyme digestion, additional subcloning of DNA fragments and transfection into mammalian, E. coli or other cells.

Sequence Confirmation.

Purified plasmid DNA is resuspended in $dH_2O$ and quantitated by measuring the absorbance at 260/280 nm in a Bausch and Lomb Spectronic 601 UV spectrometer. DNA samples are sequenced using ABI PRISSM DyeDeoxy™ terminator sequencing chemistry (Applied Biosystems Division of Perkin Elmer Corporation, Lincoln City, Calif.) kits (Part Number 401388 or 402078) according to the manufacturers suggested protocol usually modified by the addition of 5% DMSO to the sequencing mixture. Sequencing reactions are performed in a Model 480 DNA thermal cycler (Perkin Elmer Corporation, Norwalk, Conn.) following the recommended amplification conditions. Samples are purified to remove excess dye terminators with Centri-Sep™ spin columns (Princeton Separations, Adelphia, N.J.) and lyophilized. Fluorescent dye labeled sequencing reactions are resuspended in deionized formamide, and sequenced on denaturing 4.75% polyacrylamide-8M urea gels using an ABI Model 373A automated DNA sequencer. Overlapping DNA sequence fragments are analyzed and assembled into master DNA contigs using Sequencher DNA analysis software (Gene Codes Corporation, Ann Arbor, Mich.).

Expression of Stem Cell Factor Receptor Agonists in Mammalian Cells

Mammalian Cell Transfection/Production of Conditioned Media

The BHK-21 cell line can be obtained from the ATCC (Rockville, Md.). The cells are cultured in Dulbecco's modified Eagle media (DMEM/high-glucose), supplemented to 2 mM (mM) L-glutamine and 10% fetal bovine serum (FBS). This formulation is designated BHK growth media. Selective media is BHK growth media supplemented with 453 units/mL hygromycin B (Calbiochem, San Diego, Calif.). The BHK-21 cell line was previously stably transfected with the HSV transactivating protein VP16, which transactivates the IE110 promoter found on the plasmid pMON3359 (See Hippenmeyer et al., Bio/Technology, pp. 1037–1041, 1993). The VP16 protein drives expression of genes inserted behind the IE110 promoter. BHK-21 cells expressing the transactivating protein VP16 are designated BHK-VP16. The plasmid pMON1118 (See Highkin et al., Poultry Sci., 70: 970–981, 1991) expresses the hygromycin resistance gene from the SV40 promoter. A similar plasmid is available from ATCC, pSV2-hph.

BHK-VP16 cells are seeded into a 60 millimeter (mm) tissue culture dish at $3 \times 10^5$ cells per dish 24 hours prior to transfection. Cells are transfected for 16 hours in 3 mL of "OPTIMEM"™ (Gibco-BRL, Gaithersburg, Md.) containing 10 ug of plasmid DNA containing the gene of interest, 3 ug hygromycin resistance plasmid, pMON1118, and 80 ug of Gibco-BRL "LIPOFECTAMINE"™ per dish. The media is subsequently aspirated and replaced with 3 mL of growth media. At 48 hours post-transfection, media from each dish is collected and assayed for activity (transient conditioned media). The cells are removed from the dish by trypsin-EDTA, diluted 1:10 and transferred to 100 mm tissue culture dishes containing 10 mL of selective media. After approximately 7 days in selective media, resistant cells grow into colonies several millimeters in diameter. The colonies are removed from the dish with filter paper (cut to approximately the same size as the colonies and soaked in trypsin/EDTA) and transferred to individual wells of a 24 well plate containing 1 mL of selective media. After the clones are grown to confluence, the conditioned media is re-assayed, and positive clones are expanded into growth media.

Expression of Stem Cell Factor Receptor Agonists in E. coli

E. coli strain MON105 or JM101 harboring the plasmid of interest are grown at 37° C. in M9 plus casamino acids medium with shaking in a air incubator Model G25 from New Brunswick Scientific (Edison, N.J.). Growth is monitored at OD600 until it reaches a value of 1, at which time nalidixic acid (10 milligrams/mL) in 0.1N NaOH is added to a final concentration of 50 $\mu$g/mL. The cultures are then shaken at 37° C. for three to four additional hours. A high degree of aeration is maintained throughout culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al. Molecular Cloning: A Laboratory Manual, 1982). The culture is centrifuged (5000×g) to pellet the cells.

Additional strategies for achieving high-level expression of genes in E. coli can be found in Savvas, C. M. (Microbiological Reviews 60; 512–538, 1996).

Inclusion Body Preparation, Extraction, Refolding, Dialysis, DEAE Chromatography, and Characterization of the Stem Cell Factor Receptor Agonists Which Accumulate as Inclusion Bodies in E. coli Isolation of Inclusion Bodies:

The cell pellet from a 330 mL E. coli culture is resuspended in 15 mL of sonication buffer (10 mM 2-amino-2-(hydroxymethyl) 1,3-propanediol hydrochloride (Tris-HCl), pH 8.0+1 mM ethylenediaminetetraacetic acid (EDTA)). These resuspended cells are sonicated using the microtip probe of a Sonicator Cell Disruptor (Model W-375, Heat Systems-Ultrasonics, Inc., Farmingdale, N.Y.). Three rounds of sonication in sonication buffer followed by centrifugation are employed to disrupt the cells and wash the inclusion bodies (IB). The first round of sonication is a 3 minute burst followed by a 1 minute burst, and the final two rounds of sonication are for 1 minute each.

Extraction and refolding of proteins from inclusion body pellets:

Following the final centrifugation step, the IB pellet is resuspended in 10 mL of 50 mM Tris-HCl, pH 9.5, 8M urea and 5 mM dithiothreitol (DTT) and stirred at room temperature for approximately 45 minutes to allow for denaturation of the expressed protein.

The extraction solution is transferred to a beaker containing 70 mL of 5 mM Tris-HCl, pH 9.5 and 2.3M urea and gently stirred while exposed to air at 4° C. for 18 to 48 hours to allow the proteins to refold. Refolding is monitored by analysis on a Vydac (Hesperia, Calif.) C18 reversed phase high pressure liquid chromatography (RP-HPLC) column (0.46×25 cm). A linear gradient of 40% to 65% acetonitrile, containing 0.1% trifluoroacetic acid (TFA), is employed to monitor the refold. This gradient is developed over 30 minutes at a flow rate of 1.5 mL per minute. Denatured proteins generally elute later in the gradient than the refolded proteins.

Purification:

Following the refold, contaminating *E. coli* proteins are removed by acid precipitation. The pH of the refold solution is titrated to between pH 5.0 and pH 5.2 using 15% (v/v) acetic acid (HOAc). This solution is stirred at 40° C. for 2 hours and then centrifuged for 20 minutes at 12,000×g to pellet any insoluble protein.

The supernatant from the acid precipitation step is dialyzed using a Spectra/Por 3 membrane with a molecular weight cut off (MWCO) of 3,500 daltons. The dialysis is against 2 changes of 4 liters (a 50-fold excess) of 10 mM Tris-HCl, pH 8.0 for a total of 18 hours. Dialysis lowers the sample conductivity and removes urea prior to DEAE chromatography. The sample is then centrifuged (20 minutes at 12,000×g) to pellet any insoluble protein following dialysis.

A Bio-Rad Bio-Scale DEAE2 column (7×52 mm) is used for ion exchange chromatography. The column is equilibrated in a buffer containing 10 mM Tris-HCl, pH 8.0. The protein is eluted using a 0-to-500 mM sodium chloride (NaCl) gradient, in equilibration buffer, over 45 column volumes. A flow rate of 1 mL per minute is used throughout the run. Column fractions (2 mL per fraction) are collected across the gradient and analyzed by RP HPLC on a Vydac (Hesperia, Calif.) C18 column (0.46×25 cm). A linear gradient of 40% to 65% acetonitrile, containing 0.1% trifluoroacetic acid (TFA), is employed. This gradient is developed over 30 minutes at a flow rate of 1.5 mL per minute. Pooled fractions are then dialyzed against 2 changes of 4 liters (50-to-500-fold excess) of 10 mM ammonium acetate ($NH_4Ac$), pH 4.0 for a total of 18 hours. Dialysis is performed using a Spectra/Por 3 membrane with a MWCO of 3,500 daltons. Finally, the sample is sterile filtered using a 0.22 μm syringe filter (IuStar LB syringe filter, Costar, Cambridge, Mass.), and stored at 4° C.

In some cases the folded proteins can be affinity purified using affinity reagents such as mabs or receptor subunits attached to a suitable matrix. Alternatively, (or in addition) purification can be accomplished using any of a variety of chromatographic methods such as: ion exchange, gel filtration or hydrophobic chromatography or reversed phase HPLC.

These and other protein purification methods are described in detail in Methods in Enzymology, Volume 182 'Guide to Protein Purification' edited by Murray Deutscher, Academic Press, San Diego, Calif. (1990).

Protein Characterization:

The purified protein is analyzed by RP-HPLC, electrospray mass spectrometry, and SDS-PAGE. The protein quantitation is done by amino acid composition, RP-HPLC, and Bradford protein determination. In some cases tryptic peptide mapping is performed in conjunction with electrospray mass spectrometry to confirm the identity of the protein.

Methylcellulose Assay

This assay reflects the ability of colony stimulating factors to stimulate normal bone marrow cells to produce different types of hematopoietic colonies in vitro (Bradley et al., *Aust. Exp Biol. Sci.* 44:287–300, 1966), Pluznik et al., *J. Cell Comp. Physio* 66:319–324, 1965).

Methods

Approximately 30 mL of fresh, normal, healthy bone marrow aspirate are obtained from individuals following informed consent. Under sterile conditions samples are diluted 1:5 with a 1× PBS (#14040.059 Life Technologies, Gaithersburg, Md.) solution in a 50 mL conical tube (#25339-50 Corning, Corning Md.). Ficoll (Histopaque 1077 Sigma H-8889) is layered under the diluted sample and centrifuged, 300×g for 30 min. The mononuclear cell band is removed and washed two times in 1× PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen.

Cultures are set up in triplicate with a final volume of 1.0 mL in a 35×10 mm petri dish (Nunc#174926). Culture medium is purchased from Terry Fox Labs. (HCC4230 medium (Terry Fox Labs, Vancouver, B.C., Canada) and erythropoietin (Amgen, Thousand Oaks, Calif.) is added to the culture media. 3,000–10,000 CD34+ cells are added per dish. EPO receptor agonist proteins, in conditioned media from transfected mammalian cells or purified from conditioned media from transfected mammalian cells or *E. coli*, are added to give final concentrations ranging from 0.001 nM to 10 nM. Cultures are resuspended using a 3 cc syringe and 1.0 mL is dispensed per dish. Control (baseline response) cultures received no colony stimulating factors. Positive control cultures received conditioned media (PHA stimulated human cells: Terry Fox Lab. H2400). Cultures are incubated at 37° C., 5% $CO_2$ in humidified air.

Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

Human Cord Blood Hemopoietic Growth Factor Assays

Bone marrow cells are traditionally used for in vitro assays of hematopoietic colony stimulating factor (CSF) activity. However, human bone marrow is not always available, and there is considerable variability between donors. Umbilical cord blood is comparable to bone marrow as a source of hematopoietic stem cells and progenitors (Broxmeyer et al., *PNAS USA* 89:4109–113, 1992; Mayani et al., *Blood* 81:3252–3258, 1993). In contrast to bone marrow, cord blood is more readily available on a regular basis. There is also a potential to reduce assay variability by pooling cells obtained fresh from several donors, or to create a bank of cryopreserved cells for this purpose.

Transfected cell lines:

Cell lines, such as BHK or the murine pro B cell line Baf/3, can be transfected with a colony stimulating factor receptor, such as the human stem cell factor receptor which the cell line does not have. These transfected cell lines can be used to determine the activity of the ligand of which the receptor has been transfected.

EXAMPLE 1

Genes encoding the sequence rearranged Stem Cell Factor ligands can be constructed by any one of the methods described herein or by other recombinant methods known to those skilled in the art. For the purpose of this example, the site of permutation is between residues 92(Glu) and 93(Asn) of Stem Cell Factor.

In this example a new N-terminus and a new C-terminus is created without a linker joining the original termini. This is done, as described in Method II, in 2 steps of PCR and a blunt end ligation.

In the first PCR step, using a vector containing the DNA sequence of SEQ ID NO:46 as the template, and the primers "new start" and "blunt start", a DNA fragment is created which encodes the new N-terminus. This fragment is termed "fragment start". The sequence underlined in the new start primer is the NcoI restriction site.

New start primer=gcgcgc CCATGGACAACTCATCTAAGGAT SEQ ID NO:83
Blunt start primer=GGCTGCAACAGGGGG SEQ ID NO:84

In the second PCR step, using a vector containing the DNA sequence of SEQ ID NO:120 as the template, and the primers "new stop" and "blunt stop" create a DNA fragment which encodes the new C-terminus. This fragment is termed "fragment stop". The sequence underlined in the new stop primer is the HindIII restriction site.

New stop primer=gcgcgc AAGCTTATTATTTCTTTGACGCACTCCACAAGGT CATC SEQ ID NO:85
Blunt end primer=GAAGGGATCTGCAGGAATCGT SEQ ID NO:86

In the ligation step, the two fragments created in the two PCR reactions are ligated together, digested with NcoI and HindIII and cloned into an expression vector. The clones are screened by restriction analysis and DNA sequenced to confirm the proper sequence. The primers can be designed to create restriction sites other than NcoI and HindIII to clone into other expression vectors.

EXAMPLE 2

The sequence rearranged stem cell factor receptor agonists of the present invention can be assayed for bioactivity by the methods described herein or by other assays know to those skilled in the art.

Additional techniques for the construction of the variant genes, recombinant protein expression, protein purification, protein characterization, biological activity determination can be found in WO 94/12639, WO 94/12638, WO 95/20976, WO 95/21197, WO 95/20977, WO 95/21254 and WO 96/23888 which are hereby incorporated by reference in their entirety.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

What is claimed is:

1. A human stem cell factor receptor agonist polypeptide, comprising a modified stem cell factor amino acid sequence of the Formula:

GluGlyIleCysArgAsnArgValThrAsnAsnValLys SEQ ID NO:1
                                 10

AspValThrLysLeuValAlaAsnLeuProLysAspTyr
                        20

MetIleThrLeuLysTyrValProGlyMetAspValLeu
               30

ProSerHisCysTrpIleSerGluMetValValGlnLeu
40                               50

SerAspSerLeuThrAspLeuLeuAspLysPheSerAsn
                        60

IleSerGluGlyLeuSerAsnTyrSerIleIleAspLys
               70

LeuValAsnIleValAspAspLeuValGluCysValLys
80                               90

GluAsnSerSerLysAspLeuLysLysSerPheLysSer
               100

ProGluProArgLeuPheThrProGluGluPhePheArg
               110

IlePheAsnArgSerIleAspAlaPheLysAspPheVal
         120                      130

ValAlaSerGluThrSerAspCysValValSerSerThr
                       140

LeuSerProGluLysAspSerArgValSerValThrLys
               150

ProPheMetLeuProProValAlaAla
         160          165 wherein 1–23 amino acids are optionally deleted from the C-terminus of said stem cell factor receptor agonist polypeptide;

wherein the N-terminus is joined to the C-terminus directly or through a linker capable of joining the N-terminus to the C-terminus wherein C- and N-termini are created between the amino acid residue pairs of SEQ ID NO:1 selected from the group consisting of:

23-24, 24-25, 25-26, 26-27, 27-28, 28-29, 29-30, 30-31, 31-32, 32-33, 33-34, 34-35, 35-36, 36-37, 37-38, 38-39, 39-40, 40-41, 64-65, 65-66, 66-67, 67-68, 68-69, 69-70, 70-71, 89-90, 90-91, 91-92, 92-93, 93-94, 94-95, 95-96, 96-97, 97-98, 98-99, 99-100, 100-101, 101-102, 102-103, 103-104, 104-105, 105-106, 106-107, 107-108, 108-109, 109-110, and 110-111; and said stem cell factor receptor agonist polypeptide may optionally be immediately preceded by (methionine$^{-1}$), (alanine$^{-1}$) or (methionine$^{-2}$, alanine$^{-1}$).

2. The stem cell factor receptor agonist polypeptide, as recited in claim 1, wherein said linker is selected from the group consisting of;

Ser;

Asn;

Gly;

Thr;

GlySer;

AlaAla;

GlySerGly;

GlyGlyGly;

GlyAsnGly;

GlyAlaGly;

GlyThrGly;

AlaSerAla;

AlaAlaAla;

GlyGlyGlySer SEQ ID NO:37;

GlyGlyGlySerGlyGlyGlySer SEQ ID NO:38;

GlyGlyGlySerGlyGlyGlySerGlyGlyGlySer SEQ ID NO:39;

SerGlyGlySerGlyGlySer SEQ ID NO:40;

GluPheGlyAsnMet SEQ ID NO:41;

GluPheGlyGlyAsnMet SEQ ID NO:42;

GluPheGlyGlyAsnGlyGlyAsnMet SEQ ID NO:43;

GlyGlySerAspMetAlaGly SEQ ID NO:44; and

GlyGlyGlySerGlyGlyGlyThrGlyGlyGlySerGlyGlyGly SEQ ID NO:45.

3. The stem cell factor receptor agonist polypeptide of claim 1 selected from the group consisting of; SEQ ID NO:2, SEQ ID NO:3, SEQ ID NO:4; SEQ ID NO:5; SEQ ID NO:6; SEQ ID NO:7; SEQ ID NO:8; SEQ ID NO:9; SEQ ID NO:10; SEQ ID NO:11; SEQ ID NO:12; SEQ ID NO:13; SEQ ID NO:14; SEQ ID NO:15; SEQ ID NO:16; SEQ ID NO:17; SEQ ID NO:18; SEQ ID NO:19; SEQ ID NO:20; SEQ ID NO:21; SEQ ID NO:22; SEQ ID NO:23; SEQ ID NO:24; SEQ ID NO:25; SEQ ID NO:26; SEQ ID NO:27; SEQ ID NO:28; SEQ ID NO:29; SEQ ID NO:30; SEQ ID NO:31; SEQ ID NO:32; SEQ ID NO:33; SEQ ID NO:34; SEQ ID NO:35and SEQ ID NO:36.

4. The stem cell factor receptor agonist polypeptide of claim 3 selected from the group consisting of; SEQ ID NO:13; SEQ ID NO:14; SEQ ID NO:23 and SEQ ID NO:24.

5. A nucleic acid molecule comprising a DNA sequence encoding the stem cell factor receptor agonist polypeptide of claim 1.

6. A nucleic acid molecule comprising a DNA sequence encoding the stem cell factor receptor agonist polypeptide of claim 2.

7. A nucleic acid molecule comprising a DNA sequence encoding the stem cell factor receptor agonist polypeptide of claim 3.

8. A nucleic acid molecule comprising a DNA sequence encoding the stem cell factor receptor agonist polypeptide of claim 4.

9. A method of producing a stem cell factor receptor agonist polypeptide comprising: growing under suitable nutrient conditions, a host cell transformed or transfected with a replicable vector comprising said nucleic acid molecule of claim 5, 6, 7, or 8 in a manner allowing expression of said stem cell factor receptor agonist polypeptide and recovering said stem cell factor receptor agonist polypeptide.

10. A composition comprising; a stem cell factor receptor agonist polypeptide according to claim 1, 2, 3 or 4; and a pharmaceutically acceptable carrier.

11. A composition comprising; a stem cell factor receptor agonist polypeptide according to claim 1, 2, 3 or 4; a second factor selected from the group consisting of: a colony stimulating factor, a cytokine, a lymphokine, an interleukin, and a hematopoietic growth factor; and a pharmaceutically acceptable carrier.

12. The composition according to claim 11 wherein said second factor is selected from the group consisting of: GM-CSF, G-CSF, c-mpl ligand, M-CSF, IL-1, IL-4, IL-2, IL-3, IL-5, IL-6, IL-7, IL-8, IL-9, IL-10, IL-11, IL-12, IL-13, IL-15, LIF, flt3/flk2 ligand, human growth hormone, B-cell growth factor, B-cell differentiation factor, EPO, eosinophil differentiation factor, IL-3 variants, fusion proteins, G-CSF receptor agonists, c-mpl receptor agonists, IL-3 receptor agonists, and multi-functional receptor agonists.

* * * * *

SEQUENCE LISTING (1) GENERAL INFORMATION:

(iii) NUMBER OF SEQUENCES: 86

(2) INFORMATION FOR SEQ ID NO:1:

(i) SEQUENCE CHARACTERISTICS:
       (A) LENGTH: 165 amino acids
       (B) TYPE: amino acid
       (C) STRANDEDNESS: single
       (D) TOPOLOGY: linear (xi) SEQUENCE DESCRIPTION: SEQ ID NO:1:

Glu Gly Ile Cys Arg Asn Arg Val Thr Asn Asn Val Lys Asp Val Thr
 1               5                  10                  15

Lys Leu Val Ala Asn Leu Pro Lys Asp Tyr Met Ile Thr Leu Lys Tyr
             20                  25                  30

Val Pro Gly Met Asp Val Leu Pro Ser His Cys Trp Ile Ser Glu Met
         35                  40                  45

Val Val Gln Leu Ser Asp Ser Leu Thr Asp Leu Leu Asp Lys Phe Ser
     50                  55                  60

Asn Ile Ser Glu Gly Leu Ser Asn Tyr Ser Ile Ile Asp Lys Leu Val
 65                  70                  75                  80

Asn Ile Val Asp Asp Leu Val Glu Cys Val Lys Glu Asn Ser Ser Lys
                 85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
        115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

```
Pro Pro Val Ala Ala
            165
```

(2) INFORMATION FOR SEQ ID NO:2:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:2:

```
Lys Asp Tyr Met Ile Thr Leu Lys Tyr Val Pro Gly Met Asp Val Leu
  1               5                  10                  15

Pro Ser His Cys Trp Ile Ser Glu Met Val Val Gln Leu Ser Asp Ser
             20                  25                  30

Leu Thr Asp Leu Leu Asp Lys Phe Ser Asn Ile Ser Glu Gly Leu Ser
         35                  40                  45

Asn Tyr Ser Ile Ile Asp Lys Leu Val Asn Ile Val Asp Asp Leu Val
     50                  55                  60

Glu Cys Val Lys Glu Asn Ser Ser Lys Asp Leu Lys Lys Ser Phe Lys
 65                  70                  75                  80

Ser Pro Glu Pro Arg Leu Phe Thr Pro Glu Glu Phe Phe Arg Ile Phe
                 85                  90                  95

Asn Arg Ser Ile Asp Ala Phe Lys Asp Phe Val Val Ala Ser Glu Thr
                100                 105                 110

Ser Asp Cys Val Val Ser Ser Thr Leu Ser Pro Glu Lys Asp Ser Arg
            115                 120                 125

Val Ser Val Thr Lys Pro Phe Met Leu Pro Pro Val Ala Ala Gly Gly
        130                 135                 140

Gly Ser Glu Gly Ile Cys Arg Asn Arg Val Thr Asn Asn Val Lys Asp
145                 150                 155                 160

Val Thr Lys Leu Val Ala Asn Leu Pro
                165
```

(2) INFORMATION FOR SEQ ID NO:3:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:3:

```
Asp Tyr Met Ile Thr Leu Lys Tyr Val Pro Gly Met Asp Val Leu Pro
  1               5                  10                  15

Ser His Cys Trp Ile Ser Glu Met Val Val Gln Leu Ser Asp Ser Leu
             20                  25                  30

Thr Asp Leu Leu Asp Lys Phe Ser Asn Ile Ser Glu Gly Leu Ser Asn
         35                  40                  45

Tyr Ser Ile Ile Asp Lys Leu Val Asn Ile Val Asp Asp Leu Val Glu
     50                  55                  60

Cys Val Lys Glu Asn Ser Ser Lys Asp Leu Lys Lys Ser Phe Lys Ser
 65                  70                  75                  80

Pro Glu Pro Arg Leu Phe Thr Pro Glu Phe Phe Arg Ile Phe Asn
                 85                  90                  95
```

```
Arg Ser Ile Asp Ala Phe Lys Asp Phe Val Val Ala Ser Glu Thr Ser
            100                 105                 110

Asp Cys Val Val Ser Ser Thr Leu Ser Pro Glu Lys Asp Ser Arg Val
            115                 120                 125

Ser Val Thr Lys Pro Phe Met Leu Pro Pro Val Ala Ala Gly Gly Gly
            130                 135                 140

Ser Glu Gly Ile Cys Arg Asn Arg Val Thr Asn Asn Val Lys Asp Val
145                 150                 155                 160

Thr Lys Leu Val Ala Asn Leu Pro Lys
                165
```

(2) INFORMATION FOR SEQ ID NO:4:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:4:

```
Tyr Met Ile Thr Leu Lys Tyr Val Pro Gly Met Asp Val Leu Pro Ser
1               5                   10                  15

His Cys Trp Ile Ser Glu Met Val Val Gln Leu Ser Asp Ser Leu Thr
            20                  25                  30

Asp Leu Leu Asp Lys Phe Ser Asn Ile Ser Glu Gly Leu Ser Asn Tyr
            35                  40                  45

Ser Ile Ile Asp Lys Leu Val Asn Ile Val Asp Asp Leu Val Glu Cys
            50                  55                  60

Val Lys Glu Asn Ser Ser Lys Asp Leu Lys Lys Ser Phe Lys Ser Pro
65                  70                  75                  80

Glu Pro Arg Leu Phe Thr Pro Glu Glu Phe Phe Arg Ile Phe Asn Arg
                85                  90                  95

Ser Ile Asp Ala Phe Lys Asp Phe Val Val Ala Ser Glu Thr Ser Asp
            100                 105                 110

Cys Val Val Ser Ser Thr Leu Ser Pro Glu Lys Asp Ser Arg Val Ser
            115                 120                 125

Val Thr Lys Pro Phe Met Leu Pro Pro Val Ala Ala Gly Gly Gly Ser
            130                 135                 140

Glu Gly Ile Cys Arg Asn Arg Val Thr Asn Asn Val Lys Asp Val Thr
145                 150                 155                 160

Lys Leu Val Ala Asn Leu Pro Lys Asp
                165
```

(2) INFORMATION FOR SEQ ID NO:5:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:5:

```
Pro Gly Met Asp Val Leu Pro Ser His Cys Trp Ile Ser Glu Met Val
1               5                   10                  15

Val Gln Leu Ser Asp Ser Leu Thr Asp Leu Leu Asp Lys Phe Ser Asn
            20                  25                  30
```

```
Ile Ser Glu Gly Leu Ser Asn Tyr Ser Ile Ile Asp Lys Leu Val Asn
         35                  40                  45

Ile Val Asp Asp Leu Val Glu Cys Val Lys Glu Asn Ser Ser Lys Asp
 50                  55                  60

Leu Lys Lys Ser Phe Lys Ser Pro Glu Pro Arg Leu Phe Thr Pro Glu
 65                  70                  75                  80

Glu Phe Phe Arg Ile Phe Asn Arg Ser Ile Asp Ala Phe Lys Asp Phe
                 85                  90                  95

Val Val Ala Ser Glu Thr Ser Asp Cys Val Val Ser Ser Thr Leu Ser
                100                 105                 110

Pro Glu Lys Asp Ser Arg Val Ser Val Thr Lys Pro Phe Met Leu Pro
                115                 120                 125

Pro Val Ala Ala Gly Gly Gly Ser Glu Gly Ile Cys Arg Asn Arg Val
        130                 135                 140

Thr Asn Asn Val Lys Asp Val Thr Lys Leu Val Ala Asn Leu Pro Lys
145                 150                 155                 160

Asp Tyr Met Ile Thr Leu Lys Tyr Val
                165
```

(2) INFORMATION FOR SEQ ID NO:6:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:6:

```
Gly Met Asp Val Leu Pro Ser His Cys Trp Ile Ser Glu Met Val Val
 1               5                  10                  15

Gln Leu Ser Asp Ser Leu Thr Asp Leu Leu Asp Lys Phe Ser Asn Ile
                 20                  25                  30

Ser Glu Gly Leu Ser Asn Tyr Ser Ile Ile Asp Lys Leu Val Asn Ile
             35                  40                  45

Val Asp Asp Leu Val Glu Cys Val Lys Glu Asn Ser Ser Lys Asp Leu
 50                  55                  60

Lys Lys Ser Phe Lys Ser Pro Glu Pro Arg Leu Phe Thr Pro Glu Glu
 65                  70                  75                  80

Phe Phe Arg Ile Phe Asn Arg Ser Ile Asp Ala Phe Lys Asp Phe Val
             85                  90                  95

Val Ala Ser Glu Thr Ser Asp Cys Val Val Ser Ser Thr Leu Ser Pro
            100                 105                 110

Glu Lys Asp Ser Arg Val Ser Val Thr Lys Pro Phe Met Leu Pro Pro
            115                 120                 125

Val Ala Ala Gly Gly Gly Ser Glu Gly Ile Cys Arg Asn Arg Val Thr
        130                 135                 140

Asn Asn Val Lys Asp Val Thr Lys Leu Val Ala Asn Leu Pro Lys Asp
145                 150                 155                 160

Tyr Met Ile Thr Leu Lys Tyr Val Pro
                165
```

(2) INFORMATION FOR SEQ ID NO:7:

(i) SEQUENCE CHARACTERISTICS:
        (A) LENGTH: 169 amino acids
        (B) TYPE: amino acid
        (C) STRANDEDNESS: single -continued (D) TOPOLOGY: linear (ii) MOLECULE TYPE: None (xi) SEQUENCE DESCRIPTION: SEQ ID NO:7:

Met Asp Val Leu Pro Ser His Cys Trp Ile Ser Glu Met Val Val Gln
1               5                   10                  15

Leu Ser Asp Ser Leu Thr Asp Leu Leu Asp Lys Phe Ser Asn Ile Ser
                20                  25                  30

Glu Gly Leu Ser Asn Tyr Ser Ile Ile Asp Lys Leu Val Asn Ile Val
            35                  40                  45

Asp Asp Leu Val Glu Cys Val Lys Glu Asn Ser Ser Lys Asp Leu Lys
        50                  55                  60

Lys Ser Phe Lys Ser Pro Glu Pro Arg Leu Phe Thr Pro Glu Glu Phe
65                  70                  75                  80

Phe Arg Ile Phe Asn Arg Ser Ile Asp Ala Phe Lys Asp Phe Val Val
                85                  90                  95

Ala Ser Glu Thr Ser Asp Cys Val Val Ser Ser Thr Leu Ser Pro Glu
                100                 105                 110

Lys Asp Ser Arg Val Ser Val Thr Lys Pro Phe Met Leu Pro Pro Val
                115                 120                 125

Ala Ala Gly Gly Gly Ser Glu Gly Ile Cys Arg Asn Arg Val Thr Asn
        130                 135                 140

Asn Val Lys Asp Val Thr Lys Leu Val Ala Asn Leu Pro Lys Asp Tyr
145                 150                 155                 160

Met Ile Thr Leu Lys Tyr Val Pro Gly
                165

(2) INFORMATION FOR SEQ ID NO:8:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:8:

Asp Val Leu Pro Ser His Cys Trp Ile Ser Glu Met Val Val Gln Leu
1               5                   10                  15

Ser Asp Ser Leu Thr Asp Leu Leu Asp Lys Phe Ser Asn Ile Ser Glu
                20                  25                  30

Gly Leu Ser Asn Tyr Ser Ile Ile Asp Lys Leu Val Asn Ile Val Asp
            35                  40                  45

Asp Leu Val Glu Cys Val Lys Glu Asn Ser Ser Lys Asp Leu Lys Lys
        50                  55                  60

Ser Phe Lys Ser Pro Glu Pro Arg Leu Phe Thr Pro Glu Glu Phe Phe
65                  70                  75                  80

Arg Ile Phe Asn Arg Ser Ile Asp Ala Phe Lys Asp Phe Val Val Ala
                85                  90                  95

Ser Glu Thr Ser Asp Cys Val Val Ser Ser Thr Leu Ser Pro Glu Lys
                100                 105                 110

Asp Ser Arg Val Ser Val Thr Lys Pro Phe Met Leu Pro Pro Val Ala
                115                 120                 125

Ala Gly Gly Gly Ser Glu Gly Ile Cys Arg Asn Arg Val Thr Asn Asn
        130                 135                 140

Val Lys Asp Val Thr Lys Leu Val Ala Asn Leu Pro Lys Asp Tyr Met

```
                145                 150                 155                 160
Ile Thr Leu Lys Tyr Val Pro Gly Met
                165
```

(2) INFORMATION FOR SEQ ID NO:9:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:9:

```
Val Leu Pro Ser His Cys Trp Ile Ser Glu Met Val Val Gln Leu Ser
 1               5                  10                  15

Asp Ser Leu Thr Asp Leu Leu Asp Lys Phe Ser Asn Ile Ser Glu Gly
                20                  25                  30

Leu Ser Asn Tyr Ser Ile Ile Asp Lys Leu Val Asn Ile Val Asp Asp
                35                  40                  45

Leu Val Glu Cys Val Lys Glu Asn Ser Ser Lys Asp Leu Lys Lys Ser
            50                  55                  60

Phe Lys Ser Pro Glu Pro Arg Leu Phe Thr Pro Glu Glu Phe Phe Arg
 65                 70                  75                  80

Ile Phe Asn Arg Ser Ile Asp Ala Phe Lys Asp Phe Val Val Ala Ser
                85                  90                  95

Glu Thr Ser Asp Cys Val Val Ser Ser Thr Leu Ser Pro Glu Lys Asp
                100                 105                 110

Ser Arg Val Ser Val Thr Lys Pro Phe Met Leu Pro Pro Val Ala Ala
            115                 120                 125

Gly Gly Gly Ser Glu Gly Ile Cys Arg Asn Arg Val Thr Asn Asn Val
    130                 135                 140

Lys Asp Val Thr Lys Leu Val Ala Asn Leu Pro Lys Asp Tyr Met Ile
145                 150                 155                 160

Thr Leu Lys Tyr Val Pro Gly Met Asp
                165
```

(2) INFORMATION FOR SEQ ID NO:10:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

```
Leu Pro Ser His Cys Trp Ile Ser Glu Met Val Val Gln Leu Ser Asp
 1               5                  10                  15

Ser Leu Thr Asp Leu Leu Asp Lys Phe Ser Asn Ile Ser Glu Gly Leu
                20                  25                  30

Ser Asn Tyr Ser Ile Ile Asp Lys Leu Val Asn Ile Val Asp Asp Leu
                35                  40                  45

Val Glu Cys Val Lys Glu Asn Ser Ser Lys Asp Leu Lys Lys Ser Phe
            50                  55                  60

Lys Ser Pro Glu Pro Arg Leu Phe Thr Pro Glu Glu Phe Phe Arg Ile
 65                 70                  75                  80

Phe Asn Arg Ser Ile Asp Ala Phe Lys Asp Phe Val Val Ala Ser Glu
```

```
                 85                  90                   95
Thr Ser Asp Cys Val Val Ser Ser Thr Leu Ser Pro Glu Lys Asp Ser
                100                 105                 110
Arg Val Ser Val Thr Lys Pro Phe Met Leu Pro Pro Val Ala Ala Gly
            115                 120                 125
Gly Gly Ser Glu Gly Ile Cys Arg Asn Arg Val Thr Asn Asn Val Lys
        130                 135                 140
Asp Val Thr Lys Leu Val Ala Asn Leu Pro Lys Asp Tyr Met Ile Thr
145                 150                 155                 160
Leu Lys Tyr Val Pro Gly Met Asp Val
                165
```

(2) INFORMATION FOR SEQ ID NO:11:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Pro Ser His Cys Trp Ile Ser Glu Met Val Val Gln Leu Ser Asp Ser
1                5                  10                  15
Leu Thr Asp Leu Leu Asp Lys Phe Ser Asn Ile Ser Glu Gly Leu Ser
            20                  25                  30
Asn Tyr Ser Ile Ile Asp Lys Leu Val Asn Ile Val Asp Asp Leu Val
        35                  40                  45
Glu Cys Val Lys Glu Asn Ser Ser Lys Asp Leu Lys Lys Ser Phe Lys
    50                  55                  60
Ser Pro Glu Pro Arg Leu Phe Thr Pro Glu Glu Phe Phe Arg Ile Phe
65                  70                  75                  80
Asn Arg Ser Ile Asp Ala Phe Lys Asp Phe Val Val Ala Ser Glu Thr
                85                  90                  95
Ser Asp Cys Val Val Ser Ser Thr Leu Ser Pro Glu Lys Asp Ser Arg
                100                 105                 110
Val Ser Val Thr Lys Pro Phe Met Leu Pro Pro Val Ala Ala Gly Gly
            115                 120                 125
Gly Ser Glu Gly Ile Cys Arg Asn Arg Val Thr Asn Asn Val Lys Asp
        130                 135                 140
Val Thr Lys Leu Val Ala Asn Leu Pro Lys Asp Tyr Met Ile Thr Leu
145                 150                 155                 160
Lys Tyr Val Pro Gly Met Asp Val Leu
                165
```

(2) INFORMATION FOR SEQ ID NO:12:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

```
Ser His Cys Trp Ile Ser Glu Met Val Val Gln Leu Ser Asp Ser Leu
1                5                  10                  15
Thr Asp Leu Leu Asp Lys Phe Ser Asn Ile Ser Glu Gly Leu Ser Asn
```

-continued

```
                20                  25                  30
Tyr Ser Ile Ile Asp Lys Leu Val Asn Ile Val Asp Asp Leu Val Glu
        35                  40                  45

Cys Val Lys Glu Asn Ser Ser Lys Asp Leu Lys Lys Ser Phe Lys Ser
 50                  55                  60

Pro Glu Pro Arg Leu Phe Thr Pro Glu Glu Phe Arg Ile Phe Asn
 65                  70                  75                  80

Arg Ser Ile Asp Ala Phe Lys Asp Phe Val Val Ala Ser Glu Thr Ser
                85                  90                  95

Asp Cys Val Val Ser Ser Thr Leu Ser Pro Glu Lys Asp Ser Arg Val
                100                 105                 110

Ser Val Thr Lys Pro Phe Met Leu Pro Pro Val Ala Ala Gly Gly Gly
                115                 120                 125

Ser Glu Gly Ile Cys Arg Asn Arg Val Thr Asn Asn Val Lys Asp Val
                130                 135                 140

Thr Lys Leu Val Ala Asn Leu Pro Lys Asp Tyr Met Ile Thr Leu Lys
145                 150                 155                 160

Tyr Val Pro Gly Met Asp Val Leu Pro
                165
```

(2) INFORMATION FOR SEQ ID NO:13:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

```
Asn Ile Ser Glu Gly Leu Ser Asn Tyr Ser Ile Ile Asp Lys Leu Val
 1               5                  10                  15

Asn Ile Val Asp Asp Leu Val Glu Cys Val Lys Glu Asn Ser Ser Lys
                20                  25                  30

Asp Leu Lys Lys Ser Phe Lys Ser Pro Glu Pro Arg Leu Phe Thr Pro
                35                  40                  45

Glu Glu Phe Phe Arg Ile Phe Asn Arg Ser Ile Asp Ala Phe Lys Asp
 50                  55                  60

Phe Val Val Ala Ser Glu Thr Ser Asp Cys Val Val Ser Ser Thr Leu
 65                  70                  75                  80

Ser Pro Glu Lys Asp Ser Arg Val Ser Val Thr Lys Pro Phe Met Leu
                85                  90                  95

Pro Pro Val Ala Ala Gly Gly Gly Ser Glu Gly Ile Cys Arg Asn Arg
                100                 105                 110

Val Thr Asn Asn Val Lys Asp Val Thr Lys Leu Val Ala Asn Leu Pro
                115                 120                 125

Lys Asp Tyr Met Ile Thr Leu Lys Tyr Val Pro Gly Met Asp Val Leu
                130                 135                 140

Pro Ser His Cys Trp Ile Ser Glu Met Val Val Gln Leu Ser Asp Ser
145                 150                 155                 160

Leu Thr Asp Leu Leu Asp Lys Phe Ser
                165
```

(2) INFORMATION FOR SEQ ID NO:14:

(i) SEQUENCE CHARACTERISTICS:
        (A) LENGTH: 169 amino acids (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Ile Ser Glu Gly Leu Ser Asn Tyr Ser Ile Ile Asp Lys Leu Val Asn
1               5                   10                  15

Ile Val Asp Asp Leu Val Glu Cys Val Lys Glu Asn Ser Ser Lys Asp
                20                  25                  30

Leu Lys Lys Ser Phe Lys Ser Pro Glu Pro Arg Leu Phe Thr Pro Glu
            35                  40                  45

Glu Phe Phe Arg Ile Phe Asn Arg Ser Ile Asp Ala Phe Lys Asp Phe
    50                  55                  60

Val Val Ala Ser Glu Thr Ser Asp Cys Val Ser Ser Thr Leu Ser
65                  70                  75                  80

Pro Glu Lys Asp Ser Arg Val Ser Val Thr Lys Pro Phe Met Leu Pro
                85                  90                  95

Pro Val Ala Ala Gly Gly Ser Glu Gly Ile Cys Arg Asn Arg Val
                100                 105                 110

Thr Asn Asn Val Lys Asp Val Thr Lys Leu Val Ala Asn Leu Pro Lys
                115                 120                 125

Asp Tyr Met Ile Thr Leu Lys Tyr Val Pro Gly Met Asp Val Leu Pro
        130                 135                 140

Ser His Cys Trp Ile Ser Glu Met Val Val Gln Leu Ser Asp Ser Leu
145                 150                 155                 160

Thr Asp Leu Leu Asp Lys Phe Ser Asn
                165

(2) INFORMATION FOR SEQ ID NO:15:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

Ser Glu Gly Leu Ser Asn Tyr Ser Ile Ile Asp Lys Leu Val Asn Ile
1               5                   10                  15

Val Asp Asp Leu Val Glu Cys Val Lys Glu Asn Ser Ser Lys Asp Leu
                20                  25                  30

Lys Lys Ser Phe Lys Ser Pro Glu Pro Arg Leu Phe Thr Pro Glu Glu
            35                  40                  45

Phe Phe Arg Ile Phe Asn Arg Ser Ile Asp Ala Phe Lys Asp Phe Val
    50                  55                  60

Val Ala Ser Glu Thr Ser Asp Cys Val Val Ser Ser Thr Leu Ser Pro
65                  70                  75                  80

Glu Lys Asp Ser Arg Val Ser Val Thr Lys Pro Phe Met Leu Pro Pro
                85                  90                  95

Val Ala Ala Gly Gly Gly Ser Glu Gly Ile Cys Arg Asn Arg Val Thr
                100                 105                 110

Asn Asn Val Lys Asp Val Thr Lys Leu Val Ala Asn Leu Pro Lys Asp
                115                 120                 125

Tyr Met Ile Thr Leu Lys Tyr Val Pro Gly Met Asp Val Leu Pro Ser
        130                 135                 140

```
His Cys Trp Ile Ser Glu Met Val Val Gln Leu Ser Asp Ser Leu Thr
145                 150                 155                 160

Asp Leu Leu Asp Lys Phe Ser Asn Ile
                165
```

(2) INFORMATION FOR SEQ ID NO:16:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:16:

```
Glu Gly Leu Ser Asn Tyr Ser Ile Ile Asp Lys Leu Val Asn Ile Val
1               5                   10                  15

Asp Asp Leu Val Glu Cys Val Lys Glu Asn Ser Ser Lys Asp Leu Lys
                20                  25                  30

Lys Ser Phe Lys Ser Pro Glu Pro Arg Leu Phe Thr Pro Glu Glu Phe
            35                  40                  45

Phe Arg Ile Phe Asn Arg Ser Ile Asp Ala Phe Lys Asp Phe Val Val
    50                  55                  60

Ala Ser Glu Thr Ser Asp Cys Val Val Ser Thr Leu Ser Pro Glu
65                  70                  75                  80

Lys Asp Ser Arg Val Ser Val Thr Lys Pro Phe Met Leu Pro Pro Val
                85                  90                  95

Ala Ala Gly Gly Gly Ser Glu Gly Ile Cys Arg Asn Arg Val Thr Asn
            100                 105                 110

Asn Val Lys Asp Val Thr Lys Leu Val Ala Asn Leu Pro Lys Asp Tyr
    115                 120                 125

Met Ile Thr Leu Lys Tyr Val Pro Gly Met Asp Val Leu Pro Ser His
130                 135                 140

Cys Trp Ile Ser Glu Met Val Val Gln Leu Ser Asp Ser Leu Thr Asp
145                 150                 155                 160

Leu Leu Asp Lys Phe Ser Asn Ile Ser
                165
```

(2) INFORMATION FOR SEQ ID NO:17:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:17:

```
Gly Leu Ser Asn Tyr Ser Ile Ile Asp Lys Leu Val Asn Ile Val Asp
1               5                   10                  15

Asp Leu Val Glu Cys Val Lys Glu Asn Ser Ser Lys Asp Leu Lys Lys
                20                  25                  30

Ser Phe Lys Ser Pro Glu Pro Arg Leu Phe Thr Pro Glu Glu Phe Phe
            35                  40                  45

Arg Ile Phe Asn Arg Ser Ile Asp Ala Phe Lys Asp Phe Val Val Ala
    50                  55                  60

Ser Glu Thr Ser Asp Cys Val Val Ser Ser Thr Leu Ser Pro Glu Lys
65                  70                  75                  80
```

```
Asp Ser Arg Val Ser Val Thr Lys Pro Phe Met Leu Pro Pro Val Ala
            85                  90                  95

Ala Gly Gly Gly Ser Glu Gly Ile Cys Arg Asn Arg Val Thr Asn Asn
            100                 105                 110

Val Lys Asp Val Thr Lys Leu Val Ala Asn Leu Pro Lys Asp Tyr Met
            115                 120                 125

Ile Thr Leu Lys Tyr Val Pro Gly Met Asp Val Leu Pro Ser His Cys
            130                 135                 140

Trp Ile Ser Glu Met Val Val Gln Leu Ser Asp Ser Leu Thr Asp Leu
145                 150                 155                 160

Leu Asp Lys Phe Ser Asn Ile Ser Glu
                165
```

(2) INFORMATION FOR SEQ ID NO:18:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:18:

```
Leu Ser Asn Tyr Ser Ile Ile Asp Lys Leu Val Asn Ile Val Asp Asp
1                   5                   10                  15

Leu Val Glu Cys Val Lys Glu Asn Ser Ser Lys Asp Leu Lys Lys Ser
            20                  25                  30

Phe Lys Ser Pro Glu Pro Arg Leu Phe Thr Pro Glu Glu Phe Phe Arg
            35                  40                  45

Ile Phe Asn Arg Ser Ile Asp Ala Phe Lys Asp Phe Val Val Ala Ser
            50                  55                  60

Glu Thr Ser Asp Cys Val Val Ser Ser Thr Leu Ser Pro Glu Lys Asp
65                  70                  75                  80

Ser Arg Val Ser Val Thr Lys Pro Phe Met Leu Pro Pro Val Ala Ala
            85                  90                  95

Gly Gly Gly Ser Glu Gly Ile Cys Arg Asn Arg Val Thr Asn Asn Val
            100                 105                 110

Lys Asp Val Thr Lys Leu Val Ala Asn Leu Pro Lys Asp Tyr Met Ile
            115                 120                 125

Thr Leu Lys Tyr Val Pro Gly Met Asp Val Leu Pro Ser His Cys Trp
            130                 135                 140

Ile Ser Glu Met Val Val Gln Leu Ser Asp Ser Leu Thr Asp Leu Leu
145                 150                 155                 160

Asp Lys Phe Ser Asn Ile Ser Glu Gly
                165
```

(2) INFORMATION FOR SEQ ID NO:19:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:19:

```
Ser Asn Tyr Ser Ile Ile Asp Lys Leu Val Asn Ile Val Asp Asp Leu
1                   5                   10                  15
```

```
Val Glu Cys Val Lys Glu Asn Ser Ser Lys Asp Leu Lys Lys Ser Phe
            20                  25                  30

Lys Ser Pro Glu Pro Arg Leu Phe Thr Pro Glu Glu Phe Phe Arg Ile
        35                  40                  45

Phe Asn Arg Ser Ile Asp Ala Phe Lys Asp Phe Val Val Ala Ser Glu
    50                  55                  60

Thr Ser Asp Cys Val Val Ser Ser Thr Leu Ser Pro Glu Lys Asp Ser
65                  70                  75                  80

Arg Val Ser Val Thr Lys Pro Phe Met Leu Pro Pro Val Ala Ala Gly
                85                  90                  95

Gly Gly Ser Glu Gly Ile Cys Arg Asn Arg Val Thr Asn Asn Val Lys
            100                 105                 110

Asp Val Thr Lys Leu Val Ala Asn Leu Pro Lys Asp Tyr Met Ile Thr
        115                 120                 125

Leu Lys Tyr Val Pro Gly Met Asp Val Leu Pro Ser His Cys Trp Ile
    130                 135                 140

Ser Glu Met Val Val Gln Leu Ser Asp Ser Leu Thr Asp Leu Leu Asp
145                 150                 155                 160

Lys Phe Ser Asn Ile Ser Glu Gly Leu
                165
```

(2) INFORMATION FOR SEQ ID NO:20:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:20:

```
Val Lys Glu Asn Ser Ser Lys Asp Leu Lys Lys Ser Phe Lys Ser Pro
1               5                   10                  15

Glu Pro Arg Leu Phe Thr Pro Glu Glu Phe Phe Arg Ile Phe Asn Arg
            20                  25                  30

Ser Ile Asp Ala Phe Lys Asp Phe Val Val Ala Ser Glu Thr Ser Asp
        35                  40                  45

Cys Val Val Ser Ser Thr Leu Ser Pro Glu Lys Asp Ser Arg Val Ser
    50                  55                  60

Val Thr Lys Pro Phe Met Leu Pro Pro Val Ala Ala Gly Gly Gly Ser
65                  70                  75                  80

Glu Gly Ile Cys Arg Asn Arg Val Thr Asn Asn Val Lys Asp Val Thr
                85                  90                  95

Lys Leu Val Ala Asn Leu Pro Lys Asp Tyr Met Ile Thr Leu Lys Tyr
            100                 105                 110

Val Pro Gly Met Asp Val Leu Pro Ser His Cys Trp Ile Ser Glu Met
        115                 120                 125

Val Val Gln Leu Ser Asp Ser Leu Thr Asp Leu Leu Asp Lys Phe Ser
    130                 135                 140

Asn Ile Ser Glu Gly Leu Ser Asn Tyr Ser Ile Ile Asp Lys Leu Val
145                 150                 155                 160

Asn Ile Val Asp Asp Leu Val Glu Cys
                165
```

(2) INFORMATION FOR SEQ ID NO:21:

-continued (i) SEQUENCE CHARACTERISTICS:
    (A) LENGTH: 169 amino acids
    (B) TYPE: amino acid
    (C) STRANDEDNESS: single
    (D) TOPOLOGY: linear (ii) MOLECULE TYPE: None (xi) SEQUENCE DESCRIPTION: SEQ ID NO:21:

Lys Glu Asn Ser Ser Lys Asp Leu Lys Lys Ser Phe Lys Ser Pro Glu
 1               5                  10                  15

Pro Arg Leu Phe Thr Pro Glu Glu Phe Arg Ile Phe Asn Arg Ser
             20                  25                  30

Ile Asp Ala Phe Lys Asp Phe Val Val Ala Ser Glu Thr Ser Asp Cys
             35                  40                  45

Val Val Ser Ser Thr Leu Ser Pro Glu Lys Asp Ser Arg Val Ser Val
 50                  55                  60

Thr Lys Pro Phe Met Leu Pro Pro Val Ala Ala Gly Gly Gly Ser Glu
 65                  70                  75                  80

Gly Ile Cys Arg Asn Arg Val Thr Asn Val Lys Asp Val Thr Lys
             85                  90                  95

Leu Val Ala Asn Leu Pro Lys Asp Tyr Met Ile Thr Leu Lys Tyr Val
             100                 105                 110

Pro Gly Met Asp Val Leu Pro Ser His Cys Trp Ile Ser Glu Met Val
             115                 120                 125

Val Gln Leu Ser Asp Ser Leu Thr Asp Leu Leu Asp Lys Phe Ser Asn
 130                 135                 140

Ile Ser Glu Gly Leu Ser Asn Tyr Ser Ile Ile Asp Lys Leu Val Asn
 145                 150                 155                 160

Ile Val Asp Asp Leu Val Glu Cys Val
                 165

(2) INFORMATION FOR SEQ ID NO:22:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:22:

Glu Asn Ser Ser Lys Asp Leu Lys Lys Ser Phe Lys Ser Pro Glu Pro
 1               5                  10                  15

Arg Leu Phe Thr Pro Glu Glu Phe Phe Arg Ile Phe Asn Arg Ser Ile
             20                  25                  30

Asp Ala Phe Lys Asp Phe Val Val Ala Ser Glu Thr Ser Asp Cys Val
             35                  40                  45

Val Ser Ser Thr Leu Ser Pro Glu Lys Asp Ser Arg Val Ser Val Thr
 50                  55                  60

Lys Pro Phe Met Leu Pro Pro Val Ala Ala Gly Gly Gly Ser Glu Gly
 65                  70                  75                  80

Ile Cys Arg Asn Arg Val Thr Asn Val Lys Asp Val Thr Lys Leu
             85                  90                  95

Val Ala Asn Leu Pro Lys Asp Tyr Met Ile Thr Leu Lys Tyr Val Pro
             100                 105                 110

Gly Met Asp Val Leu Pro Ser His Cys Trp Ile Ser Glu Met Val Val
             115                 120                 125

```
Gln Leu Ser Asp Ser Leu Thr Asp Leu Leu Asp Lys Phe Ser Asn Ile
    130                 135                 140

Ser Glu Gly Leu Ser Asn Tyr Ser Ile Ile Asp Lys Leu Val Asn Ile
145                 150                 155                 160

Val Asp Asp Leu Val Glu Cys Val Lys
                165
```

(2) INFORMATION FOR SEQ ID NO:23:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:23:

```
Asn Ser Ser Lys Asp Leu Lys Lys Ser Phe Lys Ser Pro Glu Pro Arg
1               5                   10                  15

Leu Phe Thr Pro Glu Glu Phe Phe Arg Ile Phe Asn Arg Ser Ile Asp
                20                  25                  30

Ala Phe Lys Asp Phe Val Val Ala Ser Glu Thr Ser Asp Cys Val Val
                35                  40                  45

Ser Ser Thr Leu Ser Pro Glu Lys Asp Ser Arg Val Ser Val Thr Lys
50                  55                  60

Pro Phe Met Leu Pro Pro Val Ala Ala Gly Gly Gly Ser Glu Gly Ile
65                  70                  75                  80

Cys Arg Asn Arg Val Thr Asn Asn Val Lys Asp Val Thr Lys Leu Val
                85                  90                  95

Ala Asn Leu Pro Lys Asp Tyr Met Ile Thr Leu Lys Tyr Val Pro Gly
                100                 105                 110

Met Asp Val Leu Pro Ser His Cys Trp Ile Ser Glu Met Val Val Gln
                115                 120                 125

Leu Ser Asp Ser Leu Thr Asp Leu Leu Asp Lys Phe Ser Asn Ile Ser
                130                 135                 140

Glu Gly Leu Ser Asn Tyr Ser Ile Ile Asp Lys Leu Val Asn Ile Val
145                 150                 155                 160

Asp Asp Leu Val Glu Cys Val Lys Glu
                165
```

(2) INFORMATION FOR SEQ ID NO:24:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:24:

```
Ser Ser Lys Asp Leu Lys Lys Ser Phe Lys Ser Pro Glu Pro Arg Leu
1               5                   10                  15

Phe Thr Pro Glu Glu Phe Phe Arg Ile Phe Asn Arg Ser Ile Asp Ala
                20                  25                  30

Phe Lys Asp Phe Val Val Ala Ser Glu Thr Ser Asp Cys Val Val Ser
                35                  40                  45

Ser Thr Leu Ser Pro Glu Lys Asp Ser Arg Val Ser Val Thr Lys Pro
50                  55                  60
```

```
Phe Met Leu Pro Pro Val Ala Ala Gly Gly Gly Ser Glu Gly Ile Cys
 65              70                  75                  80

Arg Asn Arg Val Thr Asn Asn Val Lys Asp Val Thr Lys Leu Val Ala
             85                  90                  95

Asn Leu Pro Lys Asp Tyr Met Ile Thr Leu Lys Tyr Val Pro Gly Met
             100                 105                 110

Asp Val Leu Pro Ser His Cys Trp Ile Ser Glu Met Val Val Gln Leu
             115                 120                 125

Ser Asp Ser Leu Thr Asp Leu Leu Asp Lys Phe Ser Asn Ile Ser Glu
             130                 135             140

Gly Leu Ser Asn Tyr Ser Ile Ile Asp Lys Leu Val Asn Ile Val Asp
145              150                 155                 160

Asp Leu Val Glu Cys Val Lys Glu Asn
             165
```

(2) INFORMATION FOR SEQ ID NO:25:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:25:

```
Ser Lys Asp Leu Lys Lys Ser Phe Lys Ser Pro Glu Pro Arg Leu Phe
  1              5                  10                  15

Thr Pro Glu Glu Phe Phe Arg Ile Phe Asn Arg Ser Ile Asp Ala Phe
             20                  25                  30

Lys Asp Phe Val Val Ala Ser Glu Thr Ser Asp Cys Val Val Ser Ser
             35                  40                  45

Thr Leu Ser Pro Glu Lys Asp Ser Arg Val Ser Val Thr Lys Pro Phe
 50                  55                  60

Met Leu Pro Pro Val Ala Ala Gly Gly Gly Ser Glu Gly Ile Cys Arg
 65              70                  75                  80

Asn Arg Val Thr Asn Asn Val Lys Asp Val Thr Lys Leu Val Ala Asn
             85                  90                  95

Leu Pro Lys Asp Tyr Met Ile Thr Leu Lys Tyr Val Pro Gly Met Asp
             100                 105                 110

Val Leu Pro Ser His Cys Trp Ile Ser Glu Met Val Val Gln Leu Ser
             115                 120                 125

Asp Ser Leu Thr Asp Leu Leu Asp Lys Phe Ser Asn Ile Ser Glu Gly
             130                 135             140

Leu Ser Asn Tyr Ser Ile Ile Asp Lys Leu Val Asn Ile Val Asp Asp
145              150                 155                 160

Leu Val Glu Cys Val Lys Glu Asn Ser
             165
```

(2) INFORMATION FOR SEQ ID NO:26:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:26:

```
Lys Asp Leu Lys Lys Ser Phe Lys Ser Pro Glu Pro Arg Leu Phe Thr
 1               5                  10                  15

Pro Glu Glu Phe Phe Arg Ile Phe Asn Arg Ser Ile Asp Ala Phe Lys
                 20                  25                  30

Asp Phe Val Val Ala Ser Glu Thr Ser Asp Cys Val Val Ser Ser Thr
             35                  40                  45

Leu Ser Pro Glu Lys Asp Ser Arg Val Ser Val Thr Lys Pro Phe Met
 50                  55                  60

Leu Pro Pro Val Ala Ala Gly Gly Gly Ser Glu Gly Ile Cys Arg Asn
 65                  70                  75                  80

Arg Val Thr Asn Asn Val Lys Asp Val Thr Lys Leu Val Ala Asn Leu
                 85                  90                  95

Pro Lys Asp Tyr Met Ile Thr Leu Lys Tyr Val Pro Gly Met Asp Val
                 100                 105                 110

Leu Pro Ser His Cys Trp Ile Ser Glu Met Val Val Gln Leu Ser Asp
                 115                 120                 125

Ser Leu Thr Asp Leu Leu Asp Lys Phe Ser Asn Ile Ser Glu Gly Leu
 130                 135                 140

Ser Asn Tyr Ser Ile Ile Asp Lys Leu Val Asn Ile Val Asp Asp Leu
 145                 150                 155                 160

Val Glu Cys Val Lys Glu Asn Ser Ser
                 165
```

(2) INFORMATION FOR SEQ ID NO:27:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:27:

```
Asp Leu Lys Lys Ser Phe Lys Ser Pro Glu Pro Arg Leu Phe Thr Pro
 1               5                  10                  15

Glu Glu Phe Phe Arg Ile Phe Asn Arg Ser Ile Asp Ala Phe Lys Asp
                 20                  25                  30

Phe Val Val Ala Ser Glu Thr Ser Asp Cys Val Val Ser Ser Thr Leu
             35                  40                  45

Ser Pro Glu Lys Asp Ser Arg Val Ser Val Thr Lys Pro Phe Met Leu
 50                  55                  60

Pro Pro Val Ala Ala Gly Gly Gly Ser Glu Gly Ile Cys Arg Asn Arg
 65                  70                  75                  80

Val Thr Asn Asn Val Lys Asp Val Thr Lys Leu Val Ala Asn Leu Pro
                 85                  90                  95

Lys Asp Tyr Met Ile Thr Leu Lys Tyr Val Pro Gly Met Asp Val Leu
                 100                 105                 110

Pro Ser His Cys Trp Ile Ser Glu Met Val Val Gln Leu Ser Asp Ser
                 115                 120                 125

Leu Thr Asp Leu Leu Asp Lys Phe Ser Asn Ile Ser Glu Gly Leu Ser
 130                 135                 140

Asn Tyr Ser Ile Ile Asp Lys Leu Val Asn Ile Val Asp Asp Leu Val
 145                 150                 155                 160

Glu Cys Val Lys Glu Asn Ser Ser Lys
                 165
```

(2) INFORMATION FOR SEQ ID NO:28:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:28:

```
Leu Lys Lys Ser Phe Lys Ser Pro Glu Pro Arg Leu Phe Thr Pro Glu
 1               5                  10                  15
Glu Phe Phe Arg Ile Phe Asn Arg Ser Ile Asp Ala Phe Lys Asp Phe
                20                  25                  30
Val Val Ala Ser Glu Thr Ser Asp Cys Val Val Ser Ser Thr Leu Ser
            35                  40                  45
Pro Glu Lys Asp Ser Arg Val Ser Val Thr Lys Pro Phe Met Leu Pro
        50                  55                  60
Pro Val Ala Ala Gly Gly Gly Ser Glu Gly Ile Cys Arg Asn Arg Val
    65                  70                  75                  80
Thr Asn Asn Val Lys Asp Val Thr Lys Leu Val Ala Asn Leu Pro Lys
                85                  90                  95
Asp Tyr Met Ile Thr Leu Lys Tyr Val Pro Gly Met Asp Val Leu Pro
            100                 105                 110
Ser His Cys Trp Ile Ser Glu Met Val Val Gln Leu Ser Asp Ser Leu
        115                 120                 125
Thr Asp Leu Leu Asp Lys Phe Ser Asn Ile Ser Glu Gly Leu Ser Asn
    130                 135                 140
Tyr Ser Ile Ile Asp Lys Leu Val Asn Ile Val Asp Asp Leu Val Glu
145                 150                 155                 160
Cys Val Lys Glu Asn Ser Ser Lys Asp
                165
```

(2) INFORMATION FOR SEQ ID NO:29:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:29:

```
Lys Lys Ser Phe Lys Ser Pro Glu Pro Arg Leu Phe Thr Pro Glu Glu
 1               5                  10                  15
Phe Phe Arg Ile Phe Asn Arg Ser Ile Asp Ala Phe Lys Asp Phe Val
                20                  25                  30
Val Ala Ser Glu Thr Ser Asp Cys Val Val Ser Ser Thr Leu Ser Pro
            35                  40                  45
Glu Lys Asp Ser Arg Val Ser Val Thr Lys Pro Phe Met Leu Pro Pro
        50                  55                  60
Val Ala Ala Gly Gly Gly Ser Glu Gly Ile Cys Arg Asn Arg Val Thr
    65                  70                  75                  80
Asn Asn Val Lys Asp Val Thr Lys Leu Val Ala Asn Leu Pro Lys Asp
                85                  90                  95
Tyr Met Ile Thr Leu Lys Tyr Val Pro Gly Met Asp Val Leu Pro Ser
            100                 105                 110
His Cys Trp Ile Ser Glu Met Val Val Gln Leu Ser Asp Ser Leu Thr
```

```
                    115                 120                   125

Asp Leu Leu Asp Lys Phe Ser Asn Ile Ser Glu Gly Leu Ser Asn Tyr
        130                 135                 140

Ser Ile Ile Asp Lys Leu Val Asn Ile Val Asp Asp Leu Val Glu Cys
145                 150                 155                 160

Val Lys Glu Asn Ser Ser Lys Asp Leu
                165
```

(2) INFORMATION FOR SEQ ID NO:30:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:30:

```
Lys Ser Phe Lys Ser Pro Glu Pro Arg Leu Phe Thr Pro Glu Glu Phe
1               5                   10                  15

Phe Arg Ile Phe Asn Arg Ser Ile Asp Ala Phe Lys Asp Phe Val Val
                20                  25                  30

Ala Ser Glu Thr Ser Asp Cys Val Val Ser Ser Thr Leu Ser Pro Glu
            35                  40                  45

Lys Asp Ser Arg Val Ser Val Thr Lys Pro Phe Met Leu Pro Pro Val
        50                  55                  60

Ala Ala Gly Gly Gly Ser Glu Gly Ile Cys Arg Asn Arg Val Thr Asn
65                  70                  75                  80

Asn Val Lys Asp Val Thr Lys Leu Val Ala Asn Leu Pro Lys Asp Tyr
                85                  90                  95

Met Ile Thr Leu Lys Tyr Val Pro Gly Met Asp Val Leu Pro Ser His
            100                 105                 110

Cys Trp Ile Ser Glu Met Val Val Gln Leu Ser Asp Ser Leu Thr Asp
        115                 120                 125

Leu Leu Asp Lys Phe Ser Asn Ile Ser Glu Gly Leu Ser Asn Tyr Ser
    130                 135                 140

Ile Ile Asp Lys Leu Val Asn Ile Val Asp Asp Leu Val Glu Cys Val
145                 150                 155                 160

Lys Glu Asn Ser Ser Lys Asp Leu Lys
                165
```

(2) INFORMATION FOR SEQ ID NO:31:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:31:

```
Ser Phe Lys Ser Pro Glu Pro Arg Leu Phe Thr Pro Glu Glu Phe Phe
1               5                   10                  15

Arg Ile Phe Asn Arg Ser Ile Asp Ala Phe Lys Asp Phe Val Val Ala
                20                  25                  30

Ser Glu Thr Ser Asp Cys Val Val Ser Ser Thr Leu Ser Pro Glu Lys
            35                  40                  45

Asp Ser Arg Val Ser Val Thr Lys Pro Phe Met Leu Pro Pro Val Ala
```

```
           50                  55                  60
Ala Gly Gly Gly Ser Glu Gly Ile Cys Arg Asn Arg Val Thr Asn Asn
 65                  70                  75                  80

Val Lys Asp Val Thr Lys Leu Val Ala Asn Leu Pro Lys Asp Tyr Met
                 85                  90                  95

Ile Thr Leu Lys Tyr Val Pro Gly Met Asp Val Leu Pro Ser His Cys
                100                 105                 110

Trp Ile Ser Glu Met Val Val Gln Leu Ser Asp Ser Leu Thr Asp Leu
                115                 120                 125

Leu Asp Lys Phe Ser Asn Ile Ser Glu Gly Leu Ser Asn Tyr Ser Ile
            130                 135                 140

Ile Asp Lys Leu Val Asn Ile Val Asp Asp Leu Val Glu Cys Val Lys
145                 150                 155                 160

Glu Asn Ser Ser Lys Asp Leu Lys Lys
                165
```

(2) INFORMATION FOR SEQ ID NO:32:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:32:

```
Phe Lys Ser Pro Glu Pro Arg Leu Phe Thr Pro Glu Glu Phe Phe Arg
 1                   5                  10                  15

Ile Phe Asn Arg Ser Ile Asp Ala Phe Lys Asp Phe Val Val Ala Ser
                 20                  25                  30

Glu Thr Ser Asp Cys Val Val Ser Ser Thr Leu Ser Pro Glu Lys Asp
             35                  40                  45

Ser Arg Val Ser Val Thr Lys Pro Phe Met Leu Pro Pro Val Ala Ala
     50                  55                  60

Gly Gly Gly Ser Glu Gly Ile Cys Arg Asn Arg Val Thr Asn Asn Val
 65                  70                  75                  80

Lys Asp Val Thr Lys Leu Val Ala Asn Leu Pro Lys Asp Tyr Met Ile
                 85                  90                  95

Thr Leu Lys Tyr Val Pro Gly Met Asp Val Leu Pro Ser His Cys Trp
                100                 105                 110

Ile Ser Glu Met Val Val Gln Leu Ser Asp Ser Leu Thr Asp Leu Leu
            115                 120                 125

Asp Lys Phe Ser Asn Ile Ser Glu Gly Leu Ser Asn Tyr Ser Ile Ile
        130                 135                 140

Asp Lys Leu Val Asn Ile Val Asp Asp Leu Val Glu Cys Val Lys Glu
145                 150                 155                 160

Asn Ser Ser Lys Asp Leu Lys Lys Ser
                165
```

(2) INFORMATION FOR SEQ ID NO:33:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:33:

Lys Ser Pro Glu Pro Arg Leu Phe Thr Pro Glu Phe Phe Arg Ile
1               5                  10                 15

Phe Asn Arg Ser Ile Asp Ala Phe Lys Asp Phe Val Val Ala Ser Glu
            20                  25                  30

Thr Ser Asp Cys Val Val Ser Ser Thr Leu Ser Pro Glu Lys Asp Ser
        35                  40                  45

Arg Val Ser Val Thr Lys Pro Phe Met Leu Pro Pro Val Ala Ala Gly
    50                  55                  60

Gly Gly Ser Glu Gly Ile Cys Arg Asn Arg Val Thr Asn Asn Val Lys
65                  70                  75                  80

Asp Val Thr Lys Leu Val Ala Asn Leu Pro Lys Asp Tyr Met Ile Thr
                85                  90                  95

Leu Lys Tyr Val Pro Gly Met Asp Val Leu Pro Ser His Cys Trp Ile
            100                 105                 110

Ser Glu Met Val Val Gln Leu Ser Asp Ser Leu Thr Asp Leu Leu Asp
            115                 120                 125

Lys Phe Ser Asn Ile Ser Glu Gly Leu Ser Asn Tyr Ser Ile Ile Asp
    130                 135                 140

Lys Leu Val Asn Ile Val Asp Asp Leu Val Glu Cys Val Lys Glu Asn
145                 150                 155                 160

Ser Ser Lys Asp Leu Lys Lys Ser Phe
                165

(2) INFORMATION FOR SEQ ID NO:34:

(i) SEQUENCE CHARACTERISTICS:
      (A) LENGTH: 169 amino acids
      (B) TYPE: amino acid
      (C) STRANDEDNESS: single
      (D) TOPOLOGY: linear (ii) MOLECULE TYPE: None (xi) SEQUENCE DESCRIPTION: SEQ ID NO:34:

Ser Pro Glu Pro Arg Leu Phe Thr Pro Glu Glu Phe Phe Arg Ile Phe
1               5                  10                 15

Asn Arg Ser Ile Asp Ala Phe Lys Asp Phe Val Val Ala Ser Glu Thr
            20                  25                  30

Ser Asp Cys Val Val Ser Ser Thr Leu Ser Pro Glu Lys Asp Ser Arg
        35                  40                  45

Val Ser Val Thr Lys Pro Phe Met Leu Pro Pro Val Ala Ala Gly Gly
    50                  55                  60

Gly Ser Glu Gly Ile Cys Arg Asn Arg Val Thr Asn Asn Val Lys Asp
65                  70                  75                  80

Val Thr Lys Leu Val Ala Asn Leu Pro Lys Asp Tyr Met Ile Thr Leu
                85                  90                  95

Lys Tyr Val Pro Gly Met Asp Val Leu Pro Ser His Cys Trp Ile Ser
            100                 105                 110

Glu Met Val Val Gln Leu Ser Asp Ser Leu Thr Asp Leu Leu Asp Lys
            115                 120                 125

Phe Ser Asn Ile Ser Glu Gly Leu Ser Asn Tyr Ser Ile Ile Asp Lys
    130                 135                 140

Leu Val Asn Ile Val Asp Asp Leu Val Glu Cys Val Lys Glu Asn Ser
145                 150                 155                 160

Ser Lys Asp Leu Lys Lys Ser Phe Lys
                165

(2) INFORMATION FOR SEQ ID NO:35:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:35:

```
Pro Glu Pro Arg Leu Phe Thr Pro Glu Glu Phe Phe Arg Ile Phe Asn
 1               5                  10                  15

Arg Ser Ile Asp Ala Phe Lys Asp Phe Val Val Ala Ser Glu Thr Ser
            20                  25                  30

Asp Cys Val Val Ser Ser Thr Leu Ser Pro Glu Lys Asp Ser Arg Val
        35                  40                  45

Ser Val Thr Lys Pro Phe Met Leu Pro Pro Val Ala Ala Gly Gly Gly
    50                  55                  60

Ser Glu Gly Ile Cys Arg Asn Arg Val Thr Asn Asn Val Lys Asp Val
65                  70                  75                  80

Thr Lys Leu Val Ala Asn Leu Pro Lys Asp Tyr Met Ile Thr Leu Lys
                85                  90                  95

Tyr Val Pro Gly Met Asp Val Leu Pro Ser His Cys Trp Ile Ser Glu
                100                 105                 110

Met Val Val Gln Leu Ser Asp Ser Leu Thr Asp Leu Leu Asp Lys Phe
                115                 120                 125

Ser Asn Ile Ser Glu Gly Leu Ser Asn Tyr Ser Ile Ile Asp Lys Leu
            130                 135                 140

Val Asn Ile Val Asp Asp Leu Val Glu Cys Val Lys Glu Asn Ser Ser
145                 150                 155                 160

Lys Asp Leu Lys Lys Ser Phe Lys Ser
                165
```

(2) INFORMATION FOR SEQ ID NO:36:

(i) SEQUENCE CHARACTERISTICS:
        (A) LENGTH: 169 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:36:

```
Glu Pro Arg Leu Phe Thr Pro Glu Glu Phe Phe Arg Ile Phe Asn Arg
 1               5                  10                  15

Ser Ile Asp Ala Phe Lys Asp Phe Val Val Ala Ser Glu Thr Ser Asp
            20                  25                  30

Cys Val Val Ser Ser Thr Leu Ser Pro Glu Lys Asp Ser Arg Val Ser
        35                  40                  45

Val Thr Lys Pro Phe Met Leu Pro Pro Val Ala Ala Gly Gly Gly Ser
    50                  55                  60

Glu Gly Ile Cys Arg Asn Arg Val Thr Asn Asn Val Lys Asp Val Thr
65                  70                  75                  80

Lys Leu Val Ala Asn Leu Pro Lys Asp Tyr Met Ile Thr Leu Lys Tyr
                85                  90                  95

Val Pro Gly Met Asp Val Leu Pro Ser His Cys Trp Ile Ser Glu Met
                100                 105                 110
```

```
Val Val Gln Leu Ser Asp Ser Leu Thr Asp Leu Leu Asp Lys Phe Ser
        115                 120                 125
Asn Ile Ser Glu Gly Leu Ser Asn Tyr Ser Ile Ile Asp Lys Leu Val
        130                 135                 140
Asn Ile Val Asp Asp Leu Val Glu Cys Val Lys Glu Asn Ser Ser Lys
145                 150                 155                 160
Asp Leu Lys Lys Ser Phe Lys Ser Pro
                165
```

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS: single
        (D) TOPOLOGY: linear (xi) SEQUENCE DESCRIPTION: SEQ ID NO:37:

```
Gly Gly Gly Ser
1
```

(2) INFORMATION FOR SEQ ID NO:38:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:38:

```
Gly Gly Gly Ser Gly Gly Gly Ser
1               5
```

(2) INFORMATION FOR SEQ ID NO:39:

(i) SEQUENCE CHARACTERISTICS:
        (A) LENGTH: 12 amino acids
        (B) TYPE: amino acid
        (C) STRANDEDNESS: single
        (D) TOPOLOGY: linear (xi) SEQUENCE DESCRIPTION: SEQ ID NO:39:

```
Gly Gly Gly Ser Gly Gly Gly Ser Gly Gly Gly Ser
1               5                   10
```

(2) INFORMATION FOR SEQ ID NO:40:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:40:

```
Ser Gly Gly Ser Gly Gly Ser
1               5
```

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS: single
        (D) TOPOLOGY: linear (xi) SEQUENCE DESCRIPTION: SEQ ID NO:41:

```
Glu Phe Gly Asn Met
1               5

(2) INFORMATION FOR SEQ ID NO:42:

(i) SEQUENCE CHARACTERISTICS:
        (A) LENGTH: 6 amino acids
        (B) TYPE: amino acid
        (C) STRANDEDNESS: single
        (D) TOPOLOGY: linear (xi) SEQUENCE DESCRIPTION: SEQ ID NO:42:

Glu Phe Gly Gly Asn Met
1               5

(2) INFORMATION FOR SEQ ID NO:43:

(i) SEQUENCE CHARACTERISTICS:
        (A) LENGTH: 9 amino acids
        (B) TYPE: amino acid
        (C) STRANDEDNESS: single
        (D) TOPOLOGY: linear (xi) SEQUENCE DESCRIPTION: SEQ ID NO:43:

Glu Phe Gly Gly Asn Gly Gly Asn Met
1               5

(2) INFORMATION FOR SEQ ID NO:44:

(i) SEQUENCE CHARACTERISTICS:
        (A) LENGTH: 7 amino acids
        (B) TYPE: amino acid
        (C) STRANDEDNESS: single
        (D) TOPOLOGY: linear (xi) SEQUENCE DESCRIPTION: SEQ ID NO:44:

Gly Gly Ser Asp Met Ala Gly
1               5

(2) INFORMATION FOR SEQ ID NO:45:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:45:

Gly Gly Gly Ser Gly Gly Gly Thr Gly Gly Gly Ser Gly Gly Gly
1               5                   10                  15

(2) INFORMATION FOR SEQ ID NO:46:

(i) SEQUENCE CHARACTERISTICS:
        (A) LENGTH: 495 base pairs
        (B) TYPE: nucleic acid
        (C) STRANDEDNESS: single
        (D) TOPOLOGY: linear (xi) SEQUENCE DESCRIPTION: SEQ ID NO:46:

GAAGGGATCT GCAGGAATCG TGTGACTAAT AATGTAAAAG ACGTCACTAA ATTGGTGGCA      60

AATCTTCCAA AAGACTACAT GATAACCCTC AAATATGTCC CCGGGATGGA TGTTTTGCCA    120

AGTCATTGTT GGATAAGCGA GATGGTAGTA CAATTGTCAG ACAGCTTGAC TGATCTTCTG    180

GACAAGTTTT CAAATATTTC TGAAGGCTTG AGTAATTATT CCATCATAGA CAAACTTGTG    240

AATATAGTCG ATGACCTTGT GGAGTGCGTC AAAGAAAACT CATCTAAGGA TCTAAAAAAA    300
```

```
TCATTCAAGA GCCCAGAACC CAGGCTCTTT ACTCCTGAAG AATTCTTTAG AATTTTTAAT      360

AGATCCATTG ATGCCTTCAA GGACTTTGTA GTGGCATCTG AAACTAGTGA TTGTGTGGTT      420

TCTTCAACAT TAAGTCCTGA GAAAGATTCC AGAGTCAGTG TCACAAAACC ATTTATGTTA      480

CCCCCTGTTG CAGCC                                                      495

(2) INFORMATION FOR SEQ ID NO:47:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:47:

AAAGACTACA TGATAACCCT CAAATATGTC CCCGGGATGG ATGTTTTGCC AAGTCATTGT       60

TGGATAAGCG AGATGGTAGT ACAATTGTCA GACAGCTTGA CTGATCTTCT GGACAAGTTT      120

TCAAATATTT CTGAAGGCTT GAGTAATTAT TCCATCATAG ACAAACTTGT GAATATAGTC      180

GATGACCTTG TGGAGTGCGT CAAAGAAAAC TCATCTAAGG ATCTAAAAAA ATCATTCAAG      240

AGCCCAGAAC CCAGGCTCTT TACTCCTGAA GAATTCTTTA GAATTTTTAA TAGATCCATT      300

GATGCCTTCA AGGACTTTGT AGTGGCATCT GAAACTAGTG ATTGTGTGGT TCTTCAACA       360

TTAAGTCCTG AGAAAGATTC CAGAGTCAGT GTCACAAAAC CATTTATGTT ACCCCCTGTT      420

GCAGCCGGCG GCGGCTCCGA AGGGATCTGC AGGAATCGTG TGACTAATAA TGTAAAAGAC      480

GTCACTAAAT TGGTGGCAAA TCTTCCA                                         507

(2) INFORMATION FOR SEQ ID NO:48:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:48:

GACTACATGA TAACCCTCAA ATATGTCCCC GGGATGGATG TTTTGCCAAG TCATTGTTGG       60

ATAAGCGAGA TGGTAGTACA ATTGTCAGAC AGCTTGACTG ATCTTCTGGA CAAGTTTTCA      120

AATATTTCTG AAGGCTTGAG TAATTATTCC ATCATAGACA AACTTGTGAA TATAGTCGAT      180

GACCTTGTGG AGTGCGTCAA AGAAAACTCA TCTAAGGATC TAAAAAAATC ATTCAAGAGC      240

CCAGAACCCA GGCTCTTTAC TCCTGAAGAA TTCTTTAGAA TTTTTAATAG ATCCATTGAT      300

GCCTTCAAGG ACTTTGTAGT GGCATCTGAA ACTAGTGATT GTGTGGTTTC TTCAACATTA      360

AGTCCTGAGA AGATTCCAG AGTCAGTGTC ACAAAACCAT TTATGTTACC CCTGTTGCA       420

GCCGGCGGCG GCTCCGAAGG GATCTGCAGG AATCGTGTGA CTAATAATGT AAAAGACGTC      480

ACTAAATTGG TGGCAAATCT TCCAAAA                                         507

(2) INFORMATION FOR SEQ ID NO:49:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:49:

TACATGATAA CCCTCAAATA TGTCCCCGGG ATGGATGTTT TGCCAAGTCA TTGTTGGATA       60

AGCGAGATGG TAGTACAATT GTCAGACAGC TTGACTGATC TTCTGGACAA GTTTTCAAAT      120
```

```
ATTTCTGAAG GCTTGAGTAA TTATTCCATC ATAGACAAAC TTGTGAATAT AGTCGATGAC      180

CTTGTGGAGT GCGTCAAAGA AAACTCATCT AAGGATCTAA AAAAATCATT CAAGAGCCCA      240

GAACCCAGGC TCTTTACTCC TGAAGAATTC TTTAGAATTT TTAATAGATC CATTGATGCC      300

TTCAAGGACT TTGTAGTGGC ATCTGAAACT AGTGATTGTG TGGTTTCTTC AACATTAAGT      360

CCTGAGAAAG ATTCCAGAGT CAGTGTCACA AAACCATTTA TGTTACCCCC TGTTGCAGCC      420

GGCGGCGGCT CCGAAGGGAT CTGCAGGAAT CGTGTGACTA ATAATGTAAA AGACGTCACT      480

AAATTGGTGG CAAATCTTCC AAAAGAC                                         507

(2) INFORMATION FOR SEQ ID NO:50:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:50:

CCCGGGATGG ATGTTTTGCC AAGTCATTGT TGGATAAGCG AGATGGTAGT ACAATTGTCA       60

GACAGCTTGA CTGATCTTCT GGACAAGTTT TCAAATATTT CTGAAGGCTT GAGTAATTAT      120

TCCATCATAG ACAAACTTGT GAATATAGTC GATGACCTTG TGGAGTGCGT CAAAGAAAAC      180

TCATCTAAGG ATCTAAAAAA ATCATTCAAG AGCCCAGAAC CCAGGCTCTT TACTCCTGAA      240

GAATTCTTTA GAATTTTTAA TAGATCCATT GATGCCTTCA AGGACTTTGT AGTGGCATCT      300

GAAACTAGTG ATTGTGTGGT TTCTTCAACA TTAAGTCCTG AGAAAGATTC CAGAGTCAGT      360

GTCACAAAAC CATTTATGTT ACCCCCTGTT GCAGCCGGCG GCGGCTCCGA AGGGATCTGC      420

AGGAATCGTG TGACTAATAA TGTAAAAGAC GTCACTAAAT TGGTGGCAAA TCTTCCAAAA      480

GACTACATGA TAACCCTCAA ATATGTC                                         507

(2) INFORMATION FOR SEQ ID NO:51:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:51:

GGGATGGATG TTTTGCCAAG TCATTGTTGG ATAAGCGAGA TGGTAGTACA ATTGTCAGAC       60

AGCTTGACTG ATCTTCTGGA CAAGTTTTCA AATATTTCTG AAGGCTTGAG TAATTATTCC      120

ATCATAGACA AACTTGTGAA TATAGTCGAT GACCTTGTGG AGTGCGTCAA AGAAAACTCA      180

TCTAAGGATC TAAAAAAATC ATTCAAGAGC CCAGAACCCA GGCTCTTTAC TCCTGAAGAA      240

TTCTTTAGAA TTTTTAATAG ATCCATTGAT GCCTTCAAGG ACTTTGTAGT GGCATCTGAA      300

ACTAGTGATT GTGTGGTTTC TTCAACATTA AGTCCTGAGA AAGATTCCAG AGTCAGTGTC      360

ACAAAACCAT TTATGTTACC CCCTGTTGCA GCCGGCGGCG GCTCCGAAGG GATCTGCAGG      420

AATCGTGTGA CTAATAATGT AAAAGACGTC ACTAAATTGG TGGCAAATCT TCCAAAAGAC      480

TACATGATAA CCCTCAAATA TGTCCCC                                         507

(2) INFORMATION FOR SEQ ID NO:52:

(i) SEQUENCE CHARACTERISTICS:
        (A) LENGTH: 507 base pairs
        (B) TYPE: nucleic acid
        (C) STRANDEDNESS: single
```

(D) TOPOLOGY: linear (xi) SEQUENCE DESCRIPTION: SEQ ID NO:52:

| | |
|---|---|
| ATGGATGTTT TGCCAAGTCA TTGTTGGATA AGCGAGATGG TAGTACAATT GTCAGACAGC | 60 |
| TTGACTGATC TTCTGGACAA GTTTTCAAAT ATTTCTGAAG GCTTGAGTAA TTATTCCATC | 120 |
| ATAGACAAAC TTGTGAATAT AGTCGATGAC CTTGTGGAGT GCGTCAAAGA AAACTCATCT | 180 |
| AAGGATCTAA AAAAATCATT CAAGAGCCCA GAACCCAGGC TCTTTACTCC TGAAGAATTC | 240 |
| TTTAGAATTT TTAATAGATC CATTGATGCC TTCAAGGACT TTGTAGTGGC ATCTGAAACT | 300 |
| AGTGATTGTG TGGTTTCTTC AACATTAAGT CCTGAGAAAG ATTCCAGAGT CAGTGTCACA | 360 |
| AAACCATTTA TGTTACCCCC TGTTGCAGCC GGCGGCGGCT CCGAAGGGAT CTGCAGGAAT | 420 |
| CGTGTGACTA ATAATGTAAA AGACGTCACT AAATTGGTGG CAAATCTTCC AAAAGACTAC | 480 |
| ATGATAACCC TCAAATATGT CCCCGGG | 507 |

(2) INFORMATION FOR SEQ ID NO:53:

(i) SEQUENCE CHARACTERISTICS:
 (A) LENGTH: 507 base pairs
 (B) TYPE: nucleic acid
 (C) STRANDEDNESS: single
 (D) TOPOLOGY: linear (xi) SEQUENCE DESCRIPTION: SEQ ID NO:53:

| | |
|---|---|
| GATGTTTTGC CAAGTCATTG TTGGATAAGC GAGATGGTAG TACAATTGTC AGACAGCTTG | 60 |
| ACTGATCTTC TGGACAAGTT TTCAAATATT TCTGAAGGCT TGAGTAATTA TTCCATCATA | 120 |
| GACAAACTTG TGAATATAGT CGATGACCTT GTGGAGTGCG TCAAAGAAAA CTCATCTAAG | 180 |
| GATCTAAAAA AATCATTCAA GAGCCCAGAA CCCAGGCTCT TTACTCCTGA AGAATTCTTT | 240 |
| AGAATTTTTA ATAGATCCAT TGATGCCTTC AAGGACTTTG TAGTGGCATC TGAAACTAGT | 300 |
| GATTGTGTGG TTTCTTCAAC ATTAAGTCCT GAGAAAGATT CCAGAGTCAG TGTCACAAAA | 360 |
| CCATTTATGT TACCCCCTGT TGCAGCCGGC GGCGGCTCCG AAGGGATCTG CAGGAATCGT | 420 |
| GTGACTAATA ATGTAAAAGA CGTCACTAAA TTGGTGGCAA ATCTTCCAAA AGACTACATG | 480 |
| ATAACCCTCA AATATGTCCC CGGGATG | 507 |

(2) INFORMATION FOR SEQ ID NO:54:

(i) SEQUENCE CHARACTERISTICS:
 (A) LENGTH: 507 base pairs
 (B) TYPE: nucleic acid
 (C) STRANDEDNESS: single
 (D) TOPOLOGY: linear (xi) SEQUENCE DESCRIPTION: SEQ ID NO:54:

| | |
|---|---|
| GTTTTGCCAA GTCATTGTTG GATAAGCGAG ATGGTAGTAC AATTGTCAGA CAGCTTGACT | 60 |
| GATCTTCTGG ACAAGTTTTC AAATATTTCT GAAGGCTTGA GTAATTATTC CATCATAGAC | 120 |
| AAACTTGTGA ATATAGTCGA TGACCTTGTG GAGTGCGTCA AGAAAACTC ATCTAAGGAT | 180 |
| CTAAAAAAAT CATTCAAGAG CCCAGAACCC AGGCTCTTTA CTCCTGAAGA ATTCTTTAGA | 240 |
| ATTTTTAATA GATCCATTGA TGCCTTCAAG GACTTTGTAG TGGCATCTGA AACTAGTGAT | 300 |
| TGTGTGGTTT CTTCAACATT AAGTCCTGAG AAAGATTCCA GAGTCAGTGT CACAAAACCA | 360 |
| TTTATGTTAC CCCCTGTTGC AGCCGGCGGC GGCTCCGAAG GGATCTGCAG GAATCGTGTG | 420 |
| ACTAATAATG TAAAAGACGT CACTAAATTG GTGGCAAATC TTCCAAAAGA CTACATGATA | 480 |
| ACCCTCAAAT ATGTCCCCGG GATGGAT | 507 |

(2) INFORMATION FOR SEQ ID NO:55:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:55:

```
TTGCCAAGTC ATTGTTGGAT AAGCGAGATG GTAGTACAAT TGTCAGACAG CTTGACTGAT    60
CTTCTGGACA AGTTTTCAAA TATTTCTGAA GGCTTGAGTA ATTATTCCAT CATAGACAAA   120
CTTGTGAATA TAGTCGATGA CCTTGTGGAG TGCGTCAAAG AAAACTCATC TAAGGATCTA   180
AAAAAATCAT TCAAGAGCCC AGAACCCAGG CTCTTTACTC CTGAAGAATT CTTTAGAATT   240
TTTAATAGAT CCATTGATGC CTTCAAGGAC TTTGTAGTGG CATCTGAAAC TAGTGATTGT   300
GTGGTTTCTT CAACATTAAG TCCTGAGAAA GATTCCAGAG TCAGTGTCAC AAAACCATTT   360
ATGTTACCCC CTGTTGCAGC CGGCGGCGGC TCCGAAGGGA TCTGCAGGAA TCGTGTGACT   420
AATAATGTAA AAGACGTCAC TAAATTGGTG GCAAATCTTC CAAAAGACTA CATGATAACC   480
CTCAAATATG TCCCCGGGAT GGATGTT                                      507
```

(2) INFORMATION FOR SEQ ID NO:56:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:56:

```
CCAAGTCATT GTTGGATAAG CGAGATGGTA GTACAATTGT CAGACAGCTT GACTGATCTT    60
CTGGACAAGT TTTCAAATAT TTCTGAAGGC TTGAGTAATT ATTCCATCAT AGACAAACTT   120
GTGAATATAG TCGATGACCT TGTGGAGTGC GTCAAAGAAA ACTCATCTAA GGATCTAAAA   180
AAATCATTCA AGAGCCCAGA ACCCAGGCTC TTTACTCCTG AAGAATTCTT TAGAATTTTT   240
AATAGATCCA TTGATGCCTT CAAGGACTTT GTAGTGGCAT CTGAAACTAG TGATTGTGTG   300
GTTTCTTCAA CATTAAGTCC TGAGAAAGAT TCCAGAGTCA GTGTCACAAA ACCATTTATG   360
TTACCCCCTG TTGCAGCCGG CGGCGGCTCC GAAGGGATCT GCAGGAATCG TGTGACTAAT   420
AATGTAAAAG ACGTCACTAA ATTGGTGGCA AATCTTCCAA AAGACTACAT GATAACCCTC   480
AAATATGTCC CCGGGATGGA TGTTTTG                                      507
```

(2) INFORMATION FOR SEQ ID NO:57:

(i) SEQUENCE CHARACTERISTICS:
        (A) LENGTH: 507 base pairs
        (B) TYPE: nucleic acid
        (C) STRANDEDNESS: single
        (D) TOPOLOGY: linear (xi) SEQUENCE DESCRIPTION: SEQ ID NO:57:

```
AGTCATTGTT GGATAAGCGA GATGGTAGTA CAATTGTCAG ACAGCTTGAC TGATCTTCTG    60
GACAAGTTTT CAAATATTTC TGAAGGCTTG AGTAATTATT CCATCATAGA CAAACTTGTG   120
AATATAGTCG ATGACCTTGT GGAGTGCGTC AAAGAAAACT CATCTAAGGA TCTAAAAAAA   180
TCATTCAAGA GCCCAGAACC CAGGCTCTTT ACTCCTGAAG AATTCTTTAG AATTTTTAAT   240
AGATCCATTG ATGCCTTCAA GGACTTTGTA GTGGCATCTG AAACTAGTGA TTGTGTGGTT   300
TCTTCAACAT TAAGTCCTGA GAAAGATTCC AGAGTCAGTG TCACAAAACC ATTTATGTTA   360
```

```
CCCCCTGTTG CAGCCGGCGG CGGCTCCGAA GGGATCTGCA GGAATCGTGT GACTAATAAT      420

GTAAAAGACG TCACTAAATT GGTGGCAAAT CTTCCAAAAG ACTACATGAT AACCCTCAAA      480

TATGTCCCCG GGATGGATGT TTTGCCA                                         507

(2) INFORMATION FOR SEQ ID NO:58:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:58:

AATATTTCTG AAGGCTTGAG TAATTATTCC ATCATAGACA AACTTGTGAA TATAGTCGAT       60

GACCTTGTGG AGTGCGTCAA AGAAAACTCA TCTAAGGATC TAAAAAAATC ATTCAAGAGC      120

CCAGAACCCA GGCTCTTTAC TCCTGAAGAA TTCTTTAGAA TTTTTAATAG ATCCATTGAT      180

GCCTTCAAGG ACTTTGTAGT GGCATCTGAA ACTAGTGATT GTGTGGTTTC TTCAACATTA      240

AGTCCTGAGA AAGATTCCAG AGTCAGTGTC ACAAAACCAT TTATGTTACC CCCTGTTGCA      300

GCCGGCGCGG CTCCGAAGGG ATCTGCAGGA ATCGTGTGAC TAATAATGTA AAAGACGTCA      360

CTAAATTGGT GGCAAATCTT CCAAAAGACT ACATGATAAC CCTCAAATAT GTCCCCGGGA      420

TGGATGTTTT GCCAAGTCAT TGTTGGATAA GCGAGATGGT AGTACAATTG TCAGACAGCT      480

TGACTGATCT TCTGGACAAG TTTTCA                                          506

(2) INFORMATION FOR SEQ ID NO:59:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:59:

ATTTCTGAAG GCTTGAGTAA TTATTCCATC ATAGACAAAC TTGTGAATAT AGTCGATGAC       60

CTTGTGGAGT GCGTCAAAGA AAACTCATCT AAGGATCTAA AAAATCATT CAAGAGCCCA       120

GAACCCAGGC TCTTTACTCC TGAAGAATTC TTTAGAATTT TTAATAGATC CATTGATGCC      180

TTCAAGGACT TTGTAGTGGC ATCTGAAACT AGTGATTGTG TGGTTTCTTC AACATTAAGT      240

CCTGAGAAAG ATTCCAGAGT CAGTGTCACA AAACCATTTA TGTTACCCCC TGTTGCAGCC      300

GGCGCGGCTC CGAAGGGATC TGCAGGAATC GTGTGACTAA TAATGTAAAA GACGTCACTA      360

AATTGGTGGC AAATCTTCCA AAAGACTACA TGATAACCCT CAAATATGTC CCCGGGATGG      420

ATGTTTTGCC AAGTCATTGT TGGATAAGCG AGATGGTAGT ACAATTGTCA GACAGCTTGA      480

CTGATCTTCT GGACAAGTTT TCAAAT                                          506

(2) INFORMATION FOR SEQ ID NO:60:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:60:

TCTGAAGGCT TGAGTAATTA TTCCATCATA GACAAACTTG TGAATATAGT CGATGACCTT       60

GTGGAGTGCG TCAAAGAAAA CTCATCTAAG GATCTAAAAA ATCATTCAA GAGCCCAGAA       120
```

```
CCCAGGCTCT TTACTCCTGA AGAATTCTTT AGAATTTTTA ATAGATCCAT TGATGCCTTC      180

AAGGACTTTG TAGTGGCATC TGAAACTAGT GATTGTGTGG TTTCTTCAAC ATTAAGTCCT      240

GAGAAAGATT CCAGAGTCAG TGTCACAAAA CCATTTATGT TACCCCCTGT TGCAGCCGGC      300

GCGGCTCCGA AGGGATCTGC AGGAATCGTG TGACTAATAA TGTAAAAGAC GTCACTAAAT      360

TGGTGGCAAA TCTTCCAAAA GACTACATGA TAACCCTCAA ATATGTCCCC GGGATGGATG      420

TTTTGCCAAG TCATTGTTGG ATAAGCGAGA TGGTAGTACA ATTGTCAGAC AGCTTGACTG      480

ATCTTCTGGA CAAGTTTTCA AATATT                                          506

(2) INFORMATION FOR SEQ ID NO:61:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:61:

GAAGGCTTGA GTAATTATTC CATCATAGAC AAACTTGTGA ATATAGTCGA TGACCTTGTG      60

GAGTGCGTCA AGAAAACTC ATCTAAGGAT CTAAAAAAAT CATTCAAGAG CCCAGAACCC      120

AGGCTCTTTA CTCCTGAAGA ATTCTTTAGA ATTTTTAATA GATCCATTGA TGCCTTCAAG      180

GACTTTGTAG TGGCATCTGA AACTAGTGAT TGTGTGGTTT CTTCAACATT AAGTCCTGAG      240

AAAGATTCCA GAGTCAGTGT CACAAAACCA TTTATGTTAC CCCTGTTGC AGCCGGCGCG      300

GCTCCGAAGG GATCTGCAGG AATCGTGTGA CTAATAATGT AAAAGACGTC ACTAAATTGG      360

TGGCAAATCT TCCAAAAGAC TACATGATAA CCCTCAAATA TGTCCCCGGG ATGGATGTTT      420

TGCCAAGTCA TTGTTGGATA AGCGAGATGG TAGTACAATT GTCAGACAGC TTGACTGATC      480

TTCTGGACAA GTTTTCAAAT ATTTCT                                          506

(2) INFORMATION FOR SEQ ID NO:62:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:62:

GGCTTGAGTA ATTATTCCAT CATAGACAAA CTTGTGAATA TAGTCGATGA CCTTGTGGAG      60

TGCGTCAAAG AAAACTCATC TAAGGATCTA AAAAAATCAT TCAAGAGCCC AGAACCCAGG      120

CTCTTTACTC CTGAAGAATT CTTTAGAATT TTTAATAGAT CCATTGATGC CTTCAAGGAC      180

TTTGTAGTGG CATCTGAAAC TAGTGATTGT GTGGTTTCTT CAACATTAAG TCCTGAGAAA      240

GATTCCAGAG TCAGTGTCAC AAAACCATTT ATGTTACCCC CTGTTGCAGC CGGCGCGGCT      300

CCGAAGGGAT CTGCAGGAAT CGTGTGACTA ATAATGTAAA AGACGTCACT AAATTGGTGG      360

CAAATCTTCC AAAAGACTAC ATGATAACCC TCAAATATGT CCCCGGGATG GATGTTTTGC      420

CAAGTCATTG TTGGATAAGC GAGATGGTAG TACAATTGTC AGACAGCTTG ACTGATCTTC      480

TGGACAAGTT TTCAAATATT TCTGAA                                          506

(2) INFORMATION FOR SEQ ID NO:63:

(i) SEQUENCE CHARACTERISTICS:
        (A) LENGTH: 506 base pairs
        (B) TYPE: nucleic acid
        (C) STRANDEDNESS: single
        (D) TOPOLOGY: linear
```

(xi) SEQUENCE DESCRIPTION: SEQ ID NO:63:

```
TTGAGTAATT ATTCCATCAT AGACAAACTT GTGAATATAG TCGATGACCT TGTGGAGTGC      60
GTCAAAGAAA ACTCATCTAA GGATCTAAAA AAATCATTCA AGAGCCCAGA ACCCAGGCTC     120
TTTACTCCTG AAGAATTCTT TAGAATTTTT AATAGATCCA TTGATGCCTT CAAGGACTTT     180
GTAGTGGCAT CTGAAACTAG TGATTGTGTG GTTTCTTCAA CATTAAGTCC TGAGAAAGAT     240
TCCAGAGTCA GTGTCACAAA ACCATTTATG TTACCCCCTG TTGCAGCCGG CGCGGCTCCG     300
AAGGGATCTG CAGGAATCGT GTGACTAATA ATGTAAAAGA CGTCACTAAA TTGGTGGCAA     360
ATCTTCCAAA AGACTACATG ATAACCCTCA AATATGTCCC CGGGATGGAT GTTTTGCCAA     420
GTCATTGTTG GATAAGCGAG ATGGTAGTAC AATTGTCAGA CAGCTTGACT GATCTTCTGG     480
ACAAGTTTTC AAATATTTCT GAAGGC                                          506
```

(2) INFORMATION FOR SEQ ID NO:64:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:64:

```
AGTAATTATT CCATCATAGA CAAACTTGTG AATATAGTCG ATGACCTTGT GGAGTGCGTC      60
AAAGAAAACT CATCTAAGGA TCTAAAAAAA TCATTCAAGA GCCCAGAACC CAGGCTCTTT     120
ACTCCTGAAG AATTCTTTAG AATTTTTAAT AGATCCATTG ATGCCTTCAA GGACTTTGTA     180
GTGGCATCTG AAACTAGTGA TTGTGTGGTT TCTTCAACAT TAAGTCCTGA GAAAGATTCC     240
AGAGTCAGTG TCACAAAACC ATTTATGTTA CCCCCTGTTG CAGCCGGCGC GGCTCCGAAG     300
GGATCTGCAG GAATCGTGTG ACTAATAATG TAAAAGACGT CACTAAATTG GTGGCAAATC     360
TTCCAAAAGA CTACATGATA ACCCTCAAAT ATGTCCCCGG GATGGATGTT TGCCAAGTC     420
ATTGTTGGAT AAGCGAGATG GTAGTACAAT TGTCAGACAG CTTGACTGAT CTTCTGGACA     480
AGTTTTCAAA TATTTCTGAA GGCTTG                                          506
```

(2) INFORMATION FOR SEQ ID NO:65:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:65:

```
GTCAAAGAAA ACTCATCTAA GGATCTAAAA AAATCATTCA AGAGCCCAGA ACCCAGGCTC      60
TTTACTCCTG AAGAATTCTT TAGAATTTTT AATAGATCCA TTGATGCCTT CAAGGACTTT     120
GTAGTGGCAT CTGAAACTAG TGATTGTGTG GTTTCTTCAA CATTAAGTCC TGAGAAAGAT     180
TCCAGAGTCA GTGTCACAAA ACCATTTATG TTACCCCCTG TTGCAGCCGG CGGCGGCTCC     240
GAAGGGATCT GCAGGAATCG TGTGACTAAT AATGTAAAGA CGTCACTAAA TTGGTGGCAA     300
ATCTTCCAAA AGACTACATG ATAACCCTCA AATATGTCCC CGGGATGGAT GTTTTGCCAA     360
GTCATTGTTG GATAAGCGAG ATGGTAGTAC AATTGTCAGA CAGCTTGACT GATCTTCTGG     420
ACAAGTTTTC AAATATTTCT GAAGGCTTGA GTAATTATTC CATCATAGAC AAACTTGTGA     480
ATATAGTCGA TGACCTTGTG GAGTGC                                          506
```

(2) INFORMATION FOR SEQ ID NO:66:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:66:

```
AAAGAAAACT CATCTAAGGA TCTAAAAAAA TCATTCAAGA GCCCAGAACC CAGGCTCTTT      60

ACTCCTGAAG AATTCTTTAG AATTTTTAAT AGATCCATTG ATGCCTTCAA GGACTTTGTA     120

GTGGCATCTG AAACTAGTGA TTGTGTGGTT TCTTCAACAT TAAGTCCTGA GAAAGATTCC     180

AGAGTCAGTG TCACAAAACC ATTTATGTTA CCCCCTGTTG CAGCCGGCGG CGGCTCCGAA     240

GGGATCTGCA GGAATCGTGT GACTAATAAT GTAAAGACGT CACTAAATTG GTGGCAAATC     300

TTCCAAAAGA CTACATGATA ACCCTCAAAT ATGTCCCCGG GATGGATGTT TTGCCAAGTC     360

ATTGTTGGAT AAGCGAGATG GTAGTACAAT TGTCAGACAG CTTGACTGAT CTTCTGGACA     420

AGTTTTCAAA TATTTCTGAA GGCTTGAGTA ATTATTCCAT CATAGACAAA CTTGTGAATA     480

TAGTCGATGA CCTTGTGGAG TGCGTC                                         506
```

(2) INFORMATION FOR SEQ ID NO:67:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:67:

```
GAAAACTCAT CTAAGGATCT AAAAAAATCA TTCAAGAGCC CAGAACCCAG GCTCTTTACT      60

CCTGAAGAAT TCTTTAGAAT TTTTAATAGA TCCATTGATG CCTTCAAGGA CTTTGTAGTG     120

GCATCTGAAA CTAGTGATTG TGTGGTTTCT TCAACATTAA GTCCTGAGAA AGATTCCAGA     180

GTCAGTGTCA CAAAACCATT TATGTTACCC CCTGTTGCAG CCGGCGGCGG CTCCGAAGGG     240

ATCTGCAGGA ATCGTGTGAC TAATAATGTA AAGACGTCAC TAAATTGGTG GCAAATCTTC     300

CAAAAGACTA CATGATAACC CTCAAATATG TCCCCGGGAT GGATGTTTTG CCAAGTCATT     360

GTTGGATAAG CGAGATGGTA GTACAATTGT CAGACAGCTT GACTGATCTT CTGGACAAGT     420

TTTCAAATAT TTCTGAAGGC TTGAGTAATT ATTCCATCAT AGACAAACTT GTGAATATAG     480

TCGATGACCT TGTGGAGTGC GTCAAA                                         506
```

(2) INFORMATION FOR SEQ ID NO:68:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:68:

```
AACTCATCTA AGGATCTAAA AAAATCATTC AAGAGCCCAG AACCCAGGCT CTTTACTCCT      60

GAAGAATTCT TTAGAATTTT TAATAGATCC ATTGATGCCT TCAAGGACTT TGTAGTGGCA     120

TCTGAAACTA GTGATTGTGT GGTTTCTTCA ACATTAAGTC CTGAGAAAGA TTCCAGAGTC     180

AGTGTCACAA AACCATTTAT GTTACCCCCT GTTGCAGCCG GCGGCGGCTC CGAAGGGATC     240

TGCAGGAATC GTGTGACTAA TAATGTAAAG ACGTCACTAA ATTGGTGGCA AATCTTCCAA     300

AAGACTACAT GATAACCCTC AAATATGTCC CCGGGATGGA TGTTTTGCCA AGTCATTGTT     360
```

```
GGATAAGCGA GATGGTAGTA CAATTGTCAG ACAGCTTGAC TGATCTTCTG GACAAGTTTT      420

CAAATATTTC TGAAGGCTTG AGTAATTATT CCATCATAGA CAAACTTGTG AATATAGTCG      480

ATGACCTTGT GGAGTGCGTC AAAGAA                                          506

(2) INFORMATION FOR SEQ ID NO:69:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:69:

TCATCTAAGG ATCTAAAAAA ATCATTCAAG AGCCCAGAAC CCAGGCTCTT TACTCCTGAA       60

GAATTCTTTA GAATTTTTAA TAGATCCATT GATGCCTTCA AGGACTTTGT AGTGGCATCT      120

GAAACTAGTG ATTGTGTGGT TCTTCAACA TTAAGTCCTG AGAAAGATTC CAGAGTCAGT       180

GTCACAAAAC CATTTATGTT ACCCCCTGTT GCAGCCGGCG GCGGCTCCGA AGGGATCTGC      240

AGGAATCGTG TGACTAATAA TGTAAAGACG TCACTAAATT GGTGGCAAAT CTTCCAAAAG      300

ACTACATGAT AACCCTCAAA TATGTCCCCG GATGGATGT TTTGCCAAGT CATTGTTGGA       360

TAAGCGAGAT GGTAGTACAA TTGTCAGACA GCTTGACTGA TCTTCTGGAC AAGTTTTCAA      420

ATATTTCTGA AGGCTTGAGT AATTATTCCA TCATAGACAA ACTTGTGAAT ATAGTCGATG      480

ACCTTGTGGA GTGCGTCAAA GAAAAC                                          506

(2) INFORMATION FOR SEQ ID NO:70:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:70:

TCTAAGGATC TAAAAAAATC ATTCAAGAGC CCAGAACCCA GGCTCTTTAC TCCTGAAGAA       60

TTCTTTAGAA TTTTTAATAG ATCCATTGAT GCCTTCAAGG ACTTTGTAGT GGCATCTGAA      120

ACTAGTGATT GTGTGGTTTC TTCAACATTA AGTCCTGAGA AAGATTCCAG AGTCAGTGTC      180

ACAAAACCAT TTATGTTACC CCCTGTTGCA GCCGGCGGCG GCTCCGAAGG GATCTGCAGG      240

AATCGTGTGA CTAATAATGT AAAGACGTCA CTAAATTGGT GGCAAATCTT CCAAAAGACT      300

ACATGATAAC CCTCAAATAT GTCCCCGGGA TGGATGTTTT GCCAAGTCAT TGTTGGATAA      360

GCGAGATGGT AGTACAATTG TCAGACAGCT TGACTGATCT TCTGGACAAG TTTTCAAATA      420

TTTCTGAAGG CTTGAGTAAT TATTCCATCA TAGACAAACT TGTGAATATA GTCGATGACC      480

TTGTGGAGTG CGTCAAAGAA AACTCA                                          506

(2) INFORMATION FOR SEQ ID NO:71:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:71:

AAGGATCTAA AAAATCATT CAAGAGCCCA GAACCCAGGC TCTTTACTCC TGAAGAATTC        60

TTTAGAATTT TTAATAGATC CATTGATGCC TTCAAGGACT TTGTAGTGGC ATCTGAAACT      120

AGTGATTGTG TGGTTTCTTC AACATTAAGT CCTGAGAAAG ATTCCAGAGT CAGTGTCACA      180
```

```
AAACCATTTA TGTTACCCCC TGTTGCAGCC GGCGGCGGCT CCGAAGGGAT CTGCAGGAAT    240

CGTGTGACTA ATAATGTAAA GACGTCACTA AATTGGTGGC AAATCTTCCA AAAGACTACA    300

TGATAACCCT CAAATATGTC CCCGGGATGG ATGTTTTGCC AAGTCATTGT TGGATAAGCG    360

AGATGGTAGT ACAATTGTCA GACAGCTTGA CTGATCTTCT GGACAAGTTT TCAAATATTT    420

CTGAAGGCTT GAGTAATTAT TCCATCATAG ACAAACTTGT GAATATAGTC GATGACCTTG    480

TGGAGTGCGT CAAAGAAAAC TCATCT                                        506

(2) INFORMATION FOR SEQ ID NO:72:

(i) SEQUENCE CHARACTERISTICS:
            (A) LENGTH: 506 base pairs
            (B) TYPE: nucleic acid
            (C) STRANDEDNESS: single
            (D) TOPOLOGY: linear (xi) SEQUENCE DESCRIPTION: SEQ ID NO:72:

GATCTAAAAA AATCATTCAA GAGCCCAGAA CCCAGGCTCT TTACTCCTGA AGAATTCTTT     60

AGAATTTTTA ATAGATCCAT TGATGCCTTC AAGGACTTTG TAGTGGCATC TGAAACTAGT    120

GATTGTGTGG TTTCTTCAAC ATTAAGTCCT GAGAAAGATT CCAGAGTCAG TGTCACAAAA    180

CCATTTATGT TACCCCCTGT TGCAGCCGGC GGCGGCTCCG AAGGGATCTG CAGGAATCGT    240

GTGACTAATA ATGTAAAGAC GTCACTAAAT TGGTGGCAAA TCTTCCAAAA GACTACATGA    300

TAACCCTCAA ATATGTCCCC GGGATGGATG TTTTGCCAAG TCATTGTTGG ATAAGCGAGA    360

TGGTAGTACA ATTGTCAGAC AGCTTGACTG ATCTTCTGGA CAAGTTTTCA AATATTTCTG    420

AAGGCTTGAG TAATTATTCC ATCATAGACA AACTTGTGAA TATAGTCGAT GACCTTGTGG    480

AGTGCGTCAA AGAAAACTCA TCTAAG                                        506

(2) INFORMATION FOR SEQ ID NO:73:

(i) SEQUENCE CHARACTERISTICS:
            (A) LENGTH: 506 base pairs
            (B) TYPE: nucleic acid
            (C) STRANDEDNESS: single
            (D) TOPOLOGY: linear (xi) SEQUENCE DESCRIPTION: SEQ ID NO:73:

CTAAAAAAAT CATTCAAGAG CCCAGAACCC AGGCTCTTTA CTCCTGAAGA ATTCTTTAGA     60

ATTTTTAATA GATCCATTGA TGCCTTCAAG GACTTTGTAG TGGCATCTGA AACTAGTGAT    120

TGTGTGGTTT CTTCAACATT AAGTCCTGAG AAAGATTCCA GAGTCAGTGT CACAAAACCA    180

TTTATGTTAC CCCCTGTTGC AGCCGGCGGC GGCTCCGAAG GGATCTGCAG GAATCGTGTG    240

ACTAATAATG TAAAGACGTC ACTAAATTGG TGGCAAATCT TCCAAAAGAC TACATGATAA    300

CCCTCAAATA TGTCCCCGGG ATGGATGTTT TGCCAAGTCA TTGTTGGATA AGCGAGATGG    360

TAGTACAATT GTCAGACAGC TTGACTGATC TTCTGGACAA GTTTTCAAAT ATTTCTGAAG    420

GCTTGAGTAA TTATTCCATC ATAGACAAAC TTGTGAATAT AGTCGATGAC CTTGTGGAGT    480

GCGTCAAAGA AAACTCATCT AAGGAT                                        506

(2) INFORMATION FOR SEQ ID NO:74:

(i) SEQUENCE CHARACTERISTICS:
            (A) LENGTH: 506 base pairs
            (B) TYPE: nucleic acid
            (C) STRANDEDNESS: single
            (D) TOPOLOGY: linear
```

(xi) SEQUENCE DESCRIPTION: SEQ ID NO:74:

```
AAAAAATCAT TCAAGAGCCC AGAACCCAGG CTCTTTACTC CTGAAGAATT CTTTAGAATT      60
TTTAATAGAT CCATTGATGC CTTCAAGGAC TTTGTAGTGG CATCTGAAAC TAGTGATTGT     120
GTGGTTTCTT CAACATTAAG TCCTGAGAAA GATTCCAGAG TCAGTGTCAC AAAACCATTT     180
ATGTTACCCC CTGTTGCAGC CGGCGGCGGC TCCGAAGGGA TCTGCAGGAA TCGTGTGACT     240
AATAATGTAA AGACGTCACT AAATTGGTGG CAAATCTTCC AAAAGACTAC ATGATAACCC     300
TCAAATATGT CCCCGGGATG GATGTTTTGC CAAGTCATTG TTGGATAAGC GAGATGGTAG     360
TACAATTGTC AGACAGCTTG ACTGATCTTC TGGACAAGTT TTCAAATATT TCTGAAGGCT     420
TGAGTAATTA TTCCATCATA GACAAACTTG TGAATATAGT CGATGACCTT GTGGAGTGCG     480
TCAAAGAAAA CTCATCTAAG GATCTA                                         506
```

(2) INFORMATION FOR SEQ ID NO:75:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:75:

```
AAATCATTCA AGAGCCCAGA ACCCAGGCTC TTTACTCCTG AAGAATTCTT TAGAATTTTT      60
AATAGATCCA TTGATGCCTT CAAGGACTTT GTAGTGGCAT CTGAAACTAG TGATTGTGTG     120
GTTTCTTCAA CATTAAGTCC TGAGAAAGAT TCCAGAGTCA GTGTCACAAA ACCATTTATG     180
TTACCCCCTG TTGCAGCCGG CGGCGGCTCC GAAGGGATCT GCAGGAATCG TGTGACTAAT     240
AATGTAAAGA CGTCACTAAA TTGGTGGCAA ATCTTCCAAA AGACTACATG ATAACCCTCA     300
AATATGTCCC CGGGATGGAT GTTTTGCCAA GTCATTGTTG GATAAGCGAG ATGGTAGTAC     360
AATTGTCAGA CAGCTTGACT GATCTTCTGG ACAAGTTTTC AAATATTTCT GAAGGCTTGA     420
GTAATTATTC CATCATAGAC AAACTTGTGA ATATAGTCGA TGACCTTGTG GAGTGCGTCA     480
AAGAAAACTC ATCTAAGGAT CTAAAA                                         506
```

(2) INFORMATION FOR SEQ ID NO:76:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:76:

```
TCATTCAAGA GCCCAGAACC CAGGCTCTTT ACTCCTGAAG AATTCTTTAG AATTTTTAAT      60
AGATCCATTG ATGCCTTCAA GGACTTTGTA GTGGCATCTG AAACTAGTGA TTGTGTGGTT     120
TCTTCAACAT TAAGTCCTGA GAAAGATTCC AGAGTCAGTG TCACAAAACC ATTTATGTTA     180
CCCCCTGTTG CAGCCGGCGG CGGCTCCGAA GGGATCTGCA GGAATCGTGT GACTAATAAT     240
GTAAAGACGT CACTAAATTG GTGGCAAATC TTCCAAAAGA CTACATGATA ACCCTCAAAT     300
ATGTCCCCGG GATGGATGTT TTGCCAAGTC ATTGTTGGAT AAGCGAGATG GTAGTACAAT     360
TGTCAGACAG CTTGACTGAT CTTCTGGACA AGTTTTCAAA TATTTCTGAA GGCTTGAGTA     420
ATTATTCCAT CATAGACAAA CTTGTGAATA TAGTCGATGA CCTTGTGGAG TGCGTCAAAG     480
AAAACTCATC TAAGGATCTA AAAAAA                                         506
```

(2) INFORMATION FOR SEQ ID NO:77:

(i) SEQUENCE CHARACTERISTICS:
    (A) LENGTH: 506 base pairs
    (B) TYPE: nucleic acid
    (C) STRANDEDNESS: single
    (D) TOPOLOGY: linear (xi) SEQUENCE DESCRIPTION: SEQ ID NO:77:

```
TTCAAGAGCC CAGAACCCAG GCTCTTTACT CCTGAAGAAT TCTTTAGAAT TTTTAATAGA      60

TCCATTGATG CCTTCAAGGA CTTTGTAGTG GCATCTGAAA CTAGTGATTG TGTGGTTTCT     120

TCAACATTAA GTCCTGAGAA AGATTCCAGA GTCAGTGTCA CAAAACCATT TATGTTACCC     180

CCTGTTGCAG CCGGCGGCGG CTCCGAAGGG ATCTGCAGGA ATCGTGTGAC TAATAATGTA     240

AAGACGTCAC TAAATTGGTG GCAAATCTTC CAAAAGACTA CATGATAACC CTCAAATATG     300

TCCCCGGGAT GGATGTTTTG CCAAGTCATT GTTGGATAAG CGAGATGGTA GTACAATTGT     360

CAGACAGCTT GACTGATCTT CTGGACAAGT TTTCAAATAT TTCTGAAGGC TTGAGTAATT     420

ATTCCATCAT AGACAAACTT GTGAATATAG TCGATGACCT TGTGGAGTGC GTCAAAGAAA     480

ACTCATCTAA GGATCTAAAA AAATCA                                          506
```

(2) INFORMATION FOR SEQ ID NO:78:

(i) SEQUENCE CHARACTERISTICS:
    (A) LENGTH: 506 base pairs
    (B) TYPE: nucleic acid
    (C) STRANDEDNESS: single
    (D) TOPOLOGY: linear (xi) SEQUENCE DESCRIPTION: SEQ ID NO:78:

```
AAGAGCCCAG AACCCAGGCT CTTTACTCCT GAAGAATTCT TTAGAATTTT TAATAGATCC      60

ATTGATGCCT TCAAGGACTT TGTAGTGGCA TCTGAAACTA GTGATTGTGT GGTTTCTTCA     120

ACATTAAGTC CTGAGAAAGA TTCCAGAGTC AGTGTCACAA AACCATTTAT GTTACCCCCT     180

GTTGCAGCCG GCGGCGGCTC CGAAGGGATC TGCAGGAATC GTGTGACTAA TAATGTAAAG     240

ACGTCACTAA ATTGGTGGCA AATCTTCCAA AAGACTACAT GATAACCCTC AAATATGTCC     300

CCGGGATGGA TGTTTTGCCA AGTCATTGTT GGATAAGCGA GATGGTAGTA CAATTGTCAG     360

ACAGCTTGAC TGATCTTCTG GACAAGTTTT CAAATATTTC TGAAGGCTTG AGTAATTATT     420

CCATCATAGA CAAACTTGTG AATATAGTCG ATGACCTTGT GGAGTGCGTC AAAGAAAACT     480

CATCTAAGGA TCTAAAAAAA TCATCC                                          506
```

(2) INFORMATION FOR SEQ ID NO:79:

(i) SEQUENCE CHARACTERISTICS:
    (A) LENGTH: 506 base pairs
    (B) TYPE: nucleic acid
    (C) STRANDEDNESS: single
    (D) TOPOLOGY: linear (xi) SEQUENCE DESCRIPTION: SEQ ID NO:79:

```
AGCCCAGAAC CCAGGCTCTT TACTCCTGAA GAATTCTTTA GAATTTTTAA TAGATCCATT      60

GATGCCTTCA AGGACTTTGT AGTGGCATCT GAAACTAGTG ATTGTGTGGT TCTTCAACA     120

TTAAGTCCTG AGAAAGATTC CAGAGTCAGT GTCACAAAAC CATTTATGTT ACCCCCTGTT     180

GCAGCCGGCG GCGGCTCCGA AGGGATCTGC AGGAATCGTG TGACTAATAA TGTAAAGACG     240

TCACTAAATT GGTGGCAAAT CTTCCAAAAG ACTACATGAT AACCCTCAAA TATGTCCCCG     300

GGATGGATGT TTTGCCAAGT CATTGTTGGA TAAGCGAGAT GGTAGTACAA TTGTCAGACA     360

GCTTGACTGA TCTTCTGGAC AAGTTTTCAA ATATTTCTGA AGGCTTGAGT AATTATTCCA     420
```

```
TCATAGACAA ACTTGTGAAT ATAGTCGATG ACCTTGTGGA GTGCGTCAAA GAAAACTCAT      480

CTAAGGATCT AAAAAAATCA TCCAAG                                          506
```

(2) INFORMATION FOR SEQ ID NO:80:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:80:

```
CCAGAACCCA GGCTCTTTAC TCCTGAAGAA TTCTTTAGAA TTTTTAATAG ATCCATTGAT       60

GCCTTCAAGG ACTTTGTAGT GGCATCTGAA ACTAGTGATT GTGTGGTTTC TTCAACATTA      120

AGTCCTGAGA AGATTCCAG AGTCAGTGTC ACAAAACCAT TTATGTTACC CCCTGTTGCA       180

GCCGGCGGCG GCTCCGAAGG GATCTGCAGG AATCGTGTGA CTAATAATGT AAAGACGTCA      240

CTAAATTGGT GGCAAATCTT CCAAAAGACT ACATGATAAC CCTCAAATAT GTCCCCGGGA      300

TGGATGTTTT GCCAAGTCAT TGTTGGATAA GCGAGATGGT AGTACAATTG TCAGACAGCT      360

TGACTGATCT TCTGGACAAG TTTTCAAATA TTTCTGAAGG CTTGAGTAAT TATTCCATCA      420

TAGACAAACT TGTGAATATA GTCGATGACC TTGTGGAGTG CGTCAAAGAA AACTCATCTA      480

AGGATCTAAA AAAATCATCC AAGAGC                                          506
```

(2) INFORMATION FOR SEQ ID NO:81:

(i) SEQUENCE CHARACTERISTICS:
        (A) LENGTH: 506 base pairs
        (B) TYPE: nucleic acid
        (C) STRANDEDNESS: single
        (D) TOPOLOGY: linear (xi) SEQUENCE DESCRIPTION: SEQ ID NO:81:

```
GAACCCAGGC TCTTTACTCC TGAAGAATTC TTTAGAATTT TTAATAGATC CATTGATGCC       60

TTCAAGGACT TTGTAGTGGC ATCTGAAACT AGTGATTGTG TGGTTTCTTC AACATTAAGT      120

CCTGAGAAAG ATTCCAGAGT CAGTGTCACA AAACCATTTA TGTTACCCCC TGTTGCAGCC      180

GGCGGCGGCT CCGAAGGGAT CTGCAGGAAT CGTGTGACTA ATAATGTAAA GACGTCACTA      240

AATTGGTGGC AAATCTTCCA AAAGACTACA TGATAACCCT CAAATATGTC CCGGGATGG       300

ATGTTTTGCC AAGTCATTGT TGGATAAGCG AGATGGTAGT ACAATTGTCA GACAGCTTGA      360

CTGATCTTCT GGACAAGTTT TCAAATATTT CTGAAGGCTT GAGTAATTAT TCCATCATAG      420

ACAAACTTGT GAATATAGTC GATGACCTTG TGGAGTGCGT CAAAGAAAAC TCATCTAAGG      480

ATCTAAAAAA ATCATCCAAG AGCCCA                                          506
```

(2) INFORMATION FOR SEQ ID NO:82:

(i) SEQUENCE CHARACTERISTICS:
        (A) LENGTH: 248 amino acids
        (B) TYPE: amino acid
        (C) STRANDEDNESS: single
        (D) TOPOLOGY: linear (xi) SEQUENCE DESCRIPTION: SEQ ID NO:82:

```
Glu Gly Ile Cys Arg Asn Arg Val Thr Asn Asn Val Lys Asp Val Thr
 1               5                  10                  15

Lys Leu Val Ala Asn Leu Pro Lys Asp Tyr Met Ile Thr Leu Lys Tyr
            20                  25                  30
```

```
Val Pro Gly Met Asp Val Leu Pro Ser His Cys Trp Ile Ser Glu Met
         35                  40                  45
Val Val Gln Leu Ser Asp Ser Leu Thr Asp Leu Leu Asp Lys Phe Ser
 50                  55                  60
Asn Ile Ser Glu Gly Leu Ser Asn Tyr Ser Ile Ile Asp Lys Leu Val
 65                  70                  75                  80
Asn Ile Val Asp Asp Leu Val Glu Cys Val Lys Glu Asn Ser Ser Lys
                 85                  90                  95
Asp Leu Lys Lys Ser Phe Lys Ser Pro Glu Pro Arg Leu Phe Thr Pro
            100                 105                 110
Glu Glu Phe Phe Arg Ile Phe Asn Arg Ser Ile Asp Ala Phe Lys Asp
            115                 120                 125
Phe Val Val Ala Ser Glu Thr Ser Asp Cys Val Val Ser Ser Thr Leu
130                 135                 140
Ser Pro Glu Lys Asp Ser Arg Val Ser Val Thr Lys Pro Phe Met Leu
145                 150                 155                 160
Pro Pro Val Ala Ala Ser Ser Leu Arg Asn Asp Ser Ser Ser Ser Asn
                165                 170                 175
Arg Lys Ala Lys Asn Pro Pro Gly Asp Ser Ser Leu His Trp Ala Ala
            180                 185                 190
Met Ala Leu Pro Ala Leu Phe Ser Leu Ile Ile Gly Phe Ala Phe Gly
        195                 200                 205
Ala Leu Tyr Trp Lys Lys Arg Gln Pro Ser Leu Thr Arg Ala Val Glu
210                 215                 220
Asn Ile Gln Ile Asn Glu Glu Asp Asn Glu Ile Ser Met Leu Gln Glu
225                 230                 235                 240
Lys Glu Arg Glu Phe Gln Glu Val
            245
```

(2) INFORMATION FOR SEQ ID NO:83:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:83:

GCGCGCCCAT GGACAACTCA TCTAAGGAT                                29

(2) INFORMATION FOR SEQ ID NO:84:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:84:

GGCTGCAACA GGGGG                                               15

(2) INFORMATION FOR SEQ ID NO:85:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:85:

GCGCGCAAGC TTATTATTTC TTTGACGCAC TCCACAAGGT CATC                44

(2) INFORMATION FOR SEQ ID NO:86:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:86:

GAAGGGATCT GCAGGAATCG T                           21